(12) United States Patent
Ter Meulen et al.

(10) Patent No.: US 11,365,230 B2
(45) Date of Patent: Jun. 21, 2022

(54) COMPOSITIONS COMPRISING LENTIVIRAL VECTORS EXPRESSING IL-12 AND METHODS OF USE THEREOF

(71) Applicant: IMMUNE DESIGN CORP., Seattle, WA (US)

(72) Inventors: Jan Henrik Ter Meulen, Seattle, WA (US); Peter Lars Aksel Berglund, Seattle, WA (US); Tinglan Tina Albershardt, Olympia, WA (US)

(73) Assignee: IMMUNE DESIGN CORP., Seattle, WA (US)

( * ) Notice: Subject to any disclaimer, the term of this patent is extended or adjusted under 35 U.S.C. 154(b) by 154 days.

(21) Appl. No.: 15/774,444

(22) PCT Filed: Nov. 8, 2016

(86) PCT No.: PCT/US2016/060968
§ 371 (c)(1),
(2) Date: May 8, 2018

(87) PCT Pub. No.: WO2017/083291
PCT Pub. Date: May 18, 2017

(65) Prior Publication Data
US 2019/0375811 A1 Dec. 12, 2019

Related U.S. Application Data

(60) Provisional application No. 62/261,655, filed on Dec. 1, 2015, provisional application No. 62/252,877, filed on Nov. 9, 2015.

(51) Int. Cl.
| | |
|---|---|
| *A61K 39/12* | (2006.01) |
| *C12N 15/86* | (2006.01) |
| *A61K 31/675* | (2006.01) |
| *A61P 35/00* | (2006.01) |
| *C07K 14/54* | (2006.01) |
| *A61K 39/00* | (2006.01) |

(52) U.S. Cl.
CPC ...... *C07K 14/5434* (2013.01); *A61K 39/0011* (2013.01); *A61K 39/12* (2013.01); *C12N 15/86* (2013.01); *A61K 31/675* (2013.01); *C12N 2740/15034* (2013.01); *C12N 2740/15044* (2013.01)

(58) Field of Classification Search
CPC ............ C07K 14/5434; A61K 39/0011; A61K 39/12; C12N 15/86
USPC ....................................................... 514/19.2
See application file for complete search history.

(56) References Cited

U.S. PATENT DOCUMENTS

| | | |
|---|---|---|
| 4,569,794 A | 2/1986 | Smith et al. |
| 4,703,004 A | 10/1987 | Hopp et al. |
| 4,886,499 A | 12/1989 | Cirelli et al. |
| 4,937,190 A | 6/1990 | Palmenberg et al. |
| 5,057,540 A | 10/1991 | Kensil et al. |
| 5,168,062 A | 12/1992 | Stinski |
| 5,279,552 A | 1/1994 | Magnet |
| 5,328,483 A | 7/1994 | Jacoby |
| 5,385,839 A | 1/1995 | Stinski |
| 5,510,474 A | 4/1996 | Quail et al. |
| 5,848,991 A | 12/1998 | Gross et al. |
| 5,994,104 A | 11/1999 | Anderson et al. |
| 5,997,501 A | 12/1999 | Gross et al. |
| 6,045,802 A | 4/2000 | Schlom et al. |
| 6,218,181 B1 | 4/2001 | Verma et al. |
| 6,482,405 B1 | 11/2002 | Tahara et al. |
| 6,494,865 B1 | 12/2002 | Alchas |
| 6,569,143 B2 | 5/2003 | Alchas et al. |
| 6,670,349 B1 | 12/2003 | Nyce |
| 6,689,118 B2 | 2/2004 | Alchas et al. |
| 6,776,776 B2 | 8/2004 | Alchas et al. |
| 6,780,171 B2 | 8/2004 | Gabel et al. |
| 6,808,506 B2 | 10/2004 | Lastovich et al. |
| 6,971,999 B2 | 12/2005 | Py et al. |
| 7,047,070 B2 | 5/2006 | Wilkinson et al. |
| 7,083,592 B2 | 8/2006 | Lastovich et al. |
| 7,083,599 B2 | 8/2006 | Alchas et al. |
| 7,108,679 B2 | 9/2006 | Alchas |
| 7,115,108 B2 | 10/2006 | Wilkinson et al. |
| 7,141,550 B2 | 11/2006 | Moelling et al. |
| 7,241,275 B2 | 7/2007 | Alchas et al. |
| 8,158,413 B2 | 4/2012 | Charneau et al. |
| 8,187,872 B2 | 5/2012 | Allen et al. |
| 8,323,662 B1 | 12/2012 | Nicolai et al. |
| 8,551,773 B2 | 10/2013 | Trono et al. |
| 8,765,462 B2 | 7/2014 | Medin et al. |

(Continued)

FOREIGN PATENT DOCUMENTS

| | | |
|---|---|---|
| CN | 101291688 A | 10/2008 |
| EP | 0784483 A2 | 7/1997 |

(Continued)

OTHER PUBLICATIONS

Zufferey et al., Self-inactivating lentivirus vector for safe and efficient in vivo gene delivery, J. Virol., 72:9873-80 (1998).
Zufferey et al., Woodchuck hepatitis virus posttranscriptional regulatory element enhances expression of transgenes delivered by retroviral vectors, J. Virol., 73:2886-2892 (1999).
Adra et al., Cloning and expression of the mouse pgk-1 gene and the nucleotide sequence of its promoter, Gene., 60:65-74 (1987).

(Continued)

*Primary Examiner* — Yan Xiao
(74) *Attorney, Agent, or Firm* — Andrew W. Custer; Anna L. Cocuzzo

(57) ABSTRACT

This patent application relates generally to the treatment of cancer, and more particularly to the use of a pseudotyped lentivirus expressing IL-12 for the treatment of cancer.

11 Claims, 31 Drawing Sheets

Specification includes a Sequence Listing.

(56) References Cited

U.S. PATENT DOCUMENTS

| | | | |
|---|---|---|---|
| 9,175,057 | B2 | 11/2015 | Schlom et al. |
| 2008/0131466 | A1 | 6/2008 | Reed et al. |
| 2012/0071859 | A1* | 3/2012 | Morgan .................. A61P 35/00 |
| | | | 604/522 |
| 2014/0170109 | A1 | 6/2014 | Wulhfard |
| 2014/0370039 | A1 | 12/2014 | Medin et al. |
| 2015/0017121 | A1 | 1/2015 | Becher et al. |
| 2016/0130317 | A1 | 5/2016 | Medin et al. |

FOREIGN PATENT DOCUMENTS

| | | |
|---|---|---|
| EP | 1062340 A2 | 12/2000 |
| EP | 1113821 A1 | 7/2001 |
| EP | 1248654 A2 | 10/2002 |
| EP | 0815245 B1 | 4/2008 |
| EP | 2591796 A1 | 5/2013 |
| EP | 2766035 A1 | 8/2014 |
| GB | 2220211 A | 1/1990 |
| WO | 90/14837 A1 | 12/1990 |
| WO | 96/10419 A2 | 4/1996 |
| WO | 98/32869 A1 | 7/1998 |
| WO | 99/46385 A2 | 9/1999 |
| WO | 00/15264 A1 | 3/2000 |
| WO | 01/52874 A2 | 7/2001 |
| WO | 2004044147 A2 | 5/2004 |
| WO | 2005111221 A1 | 11/2004 |
| WO | 2009/035528 A2 | 3/2009 |
| WO | 2009/076524 A2 | 6/2009 |
| WO | 2010/051820 A1 | 5/2010 |
| WO | 2011/011584 A1 | 1/2011 |
| WO | 2013/053775 A1 | 4/2013 |
| WO | 2013/149167 A1 | 10/2013 |
| WO | 2015/066715 A1 | 5/2015 |
| WO | 2015/095249 A1 | 6/2015 |
| WO | 2016/048903 A1 | 3/2016 |

OTHER PUBLICATIONS

Apolonia, Thesis submitted to University College London, 82-97 (2009).

Atkins et al., Phase I evaluation of intravenous recombinant human interleukin 12 in patients with advanced malignancies, Clin. Cancer. Res., 3:409-417 (1997).

Banchereau et al., Dendritic cells as vectors for therapy, Cell., 106:271-274 (2001).

Bear et al., Heparin-binding and patterns of virulence for two recombinant strains of Sindbis virus, Virology, 347:183-190 (2006).

Berg et al., Intratumoral IL-12 combined with CTLA-4 blockade elicits T cell-mediated glioma rejection, J. Exp. Med., 210:2803-11 (2013).

Bernard et al., Mutations in the E2 glycoprotein of Venezuelan equine encephalitis virus confer heparan sulfate interaction, low morbidity, and rapid clearance from blood of mice, Virology, 276:93-103 (2000).

Boon et al., Tumor antigens recognized by T lymphocytes, Annual Review of Immunology, 12:337-365 (1994).

Boshart et al., A very strong enhancer is located upstream of an immediate early gene of human cytomegalovirus, Cell, 41:521-30 (1985).

Brown et al., Structure-based mutagenesis of the human immunodeficiency virus type 1 DNA attachment site: effects on integration and cDNA synthesis, J. Virol., 73:9011-20 (1999).

Cavrois et al., A sensitive and specific enzyme-based assay detecting HIV-1 virion fusion in primary T lymphocytes, Nat. Biotechnol., 20:1151-1154 (2002).

Cha et al., Plasmid IL-12 electroporation in melanoma, Human Vaccines & Immunotherapeutics, 8:1734-1738 (2012).

Chang et al., Adjuvant activity of incomplete Freund's adjuvant, Advanced Drug Delivery Reviews, 32:173-186 (1998).

Chen et a., Induction of ErbB-2/neu-specific protective and therapeutic antitumor immunity using genetically modified dendritic cells: enhanced efficacy by cotransduction of gene encoding IL-12, Gene. Ther., 8:316-23 (2001).

Chen et al., Alteration of T cell immunity by lentiviral transduction of human monocyte-derived dendritic cells, Retrovirology, 1:37 (2004).

Chen et al., Fusion protein linkers: property, design and functionality, Adv. Drug. Deliv. Rev., 65:1357-69 (2013).

Chen et al., Oncology meets immunology: the cancer-immunity cycle, Immunity, 39:1-10 (2013).

Dahlberg, Micromanagement during the innate immune response, Sci. STKE., 387:pe25 (2007).

Deglon et al., Self-inactivating lentiviral vectors with enhanced transgene expression as potential gene transfer system in Parkinson's disease, Hum. Gene. Ther., 11:179-190 (2000).

Dobson et al., Conservation of high ef?ciency promoter sequences in *Saccharomyces cerevisiae*, Nucleic Acids Res., 10:2635-2637 (1982).

Dohnal et al., Phase I study of tumor Ag-loaded IL-12 secreting semi-mature DC for the treatment of pediatric cancer, Cytotherapy, 9:755-770 (2007).

Drose et al., Bafilomycins and concanamycins as inhibitors of V-ATPases and P-ATPases, J. Exp. Biol., 200:1-8 (1997).

Dunussi-Joannopoulos et al., Vaccines with interleukin-12-transduced acute myeloid leukemia cells elicit very potent therapeutic and long-lasting protective immunity, Blood, 94:4263-4273 (1999).

Engelman et al., Multiple effects of mutations in human immunodeficiency virus type 1 integrase on viral replication, J. Virol., 69:2729 (1995).

Fang et al., Stable antibody expression at therapeutic levels using the 2A peptide, Nat. Biotech., 23:584-590 (2005).

Felipe et al., Targeting of proteins derived from self-processing polyproteins containing multiple signal sequences, Traffic, 5:616-626 (2004).

Fire et al., Potent and specific genetic interference by double-stranded RNA in Caenorhabditis elegans, Nature, 391:806-11 (1998).

Gambotto et al., Induction of antitumor immunity by direct intratumoral injection of a recombinant adenovirus vector expressing interleukin-12, Cancer Gene Ther., 6:45-53 (1999).

Gardner et al., Infection of human dendritic cells by a sindbis virus replicon vector is determined by a single amino acid substitution in the E2 glycoprotein, J. Virol., 74:11849-57 (2000).

Geijtenbeek et al., Self- and nonself-recognition by C-type lectins on dendritic cells, Annu. Rev. Immunol., 22:33-54 (2004).

Goyvaerts et al., The transduction pattern of IL-12-encoding lentiviral vectors shapes the immunological outcome, Eur. J. Immunol., 45:3351-61 (2015).

Graham et al., A new technique for the assay of infectivity of human adenovirus 5 DNA, Virol., 52:456-67 (1973).

Griffin et al., Binding of Sindbis virus to cell surface heparan sulfate, J. Virol., 72:7349-56 (1998).

Gunning et al., A human beta-actin expression vector system directs high-level accumulation of antisense transcripts, Proc. Natl. Acad. Sci. USA, 84:4831-4835 (1989).

Harada et al., IL-12 gene therapy is an effective therapeutic strategy for hepatocellular carcinoma in immunosuppressed mice, J. Immunol., 173:6635-44 (2004).

He et al., Immunization with lentiviral vector-transduced dendritic cells induces strong and long-lasting T cell responses and therapeutic immunity, J. Immunol., 174:3808-3817 (2005).

Herberman et al., Local and systemic anti-tumor immunity is induced by rheoswitch regulated IL-12 production after intratumoral injection of adenovirus vector as well as vector-transduced dendritic cells, Ziopharm Oncology, Poster, 899:1 (2011).

Hli et al., Antitumor activity of lentivirus-mediated Interleukin-12 gene modified dendritic cells in human lung cancer in vitro, Asian Pacific Journal of Cancer Prevention, 15:611-616 (2014).

International Preliminary Report on Patentability received for PCT Patent Application No. PCT/US16/60968, dated May 24, 2018, 10 pages.

International Search Report and Written Opinion received for PCT Patent Application No. PCT/US16/60968, dated Mar. 24, 2017, 15 pages.

Iwakuma et al., Self-Inactivating Lentiviral Vectors with U3 and U5 Modifications, Virology, 261:120-132 (1999).

(56) References Cited

OTHER PUBLICATIONS

Jiang et al., Construction of a single-chain interleukin-12-expressing retroviral vector and its application in cytokine gene therapy against experimental coccidioidomycosis, Infection and Immunity, 67:2996-3001 (1999).
Kang et al., Interleukin 12 gene therapy of cancer by peritumoral injection of transduced autologous fibroblasts: outcome of a phase I study, Hum. Gene. Therapy, 12:671-684 (2001).
Kilinc et al., Reversing tumor immune suppression with intratumoral IL-12: activation of tumor-associated T effector/memory cells, induction of T suppressor apoptosis, and infiltration of CD8+ T Effectors , J. Immunol., 177:6962-6973 (2006).
Klimstra et al., Adaptation of Sindbis virus to BHK cells selects for use of heparan sulfate as an attachment receptor, J. Virol., 72:7357-7366 (1998).
Klimstra et al., DC-SIGN and L-SIGN can act as attachment receptors for alphaviruses and distinguish between mosquito cell- and mammalian cell-derived viruses, J. Virol., 77:12022-32 (2003).
Kung et al., A murine leukemia virus (MuLV) long terminal repeat derived from rhesus macaques in the context of a lentivirus vector and MuLV gag sequence results in high-level gene expression in human T lymphocytes, J. Virol., 74:3668-3681 (2000).
Lasek et al., Interleukin 12: still a promising candidate for tumor immunotherapy?, Cancer Immunol. Immunother., 63:419-435 (2014).
Leonard et al., Effects of single-dose interleukin-12 exposure on interleukin-12-associated toxicity and interferon-gamma production, Blood, 90:2541-2548 (1997).
Li et al., Efficient Treg depletion induces T-cell infiltration and rejection of large tumors, Eur. J. Immunol., 40:3325-3335 (2010).
Lieberman et al., Recognition of a small number of diverse epitopes dominates the cytotoxic T lymphocytes response to HIV type 1 in an infected individual, AIDS Res. Hum. Retroviruses, 13:383-392 (1997).
Linette et al., A phase I open-label study of Ad-RTS-hIL-12, an adenoviral vector engineered to express hIL-12, in combination with an oral activator ligand in subjects with unresectable Stage III/IV melanoma, Ziopharm Oncology, 1 (2013).
Liu et al., In situ adenoviral interleukin 12 gene transfer confers potent and long-lasting cytotoxic immunity in glioma, Cancer Gene. Therapy, 9:9-15 (2002).
Livingston et al., The hepatitis B virus-specific CTL responses induced in humans by lipopeptide vaccination are comparable to those elicited by acute viral infection, Immunol., 159:1383-1392 (1997).
Maszialerz et al., Mechanisms of macrophage cytotoxicity in IL-2 and IL-12 mediated tumour regression, Cancer Immunol. Immunother., 52:235-242 (2003).
Mazzolini et al., Intratumoral injection of dendritic cells engineered to secrete interleukin-12 by recombinant adenovirus in patients with metastatic gastrointestinal carcinomas, Journal of Clinical Oncology, 23:999-1010 (2005).
Mcwilliams et al., Mutations in the 5' end of the human immunodeficiency virus type 1 polypurine tract affect RNase H cleavage specificity and virus titer, J. Virol., 77:11150-7 (2003).
Meissner et al., Development of an inducible pol III transcription system essentially requiring a mutated form of the TATA-binding protein, Nucleic Acids Research, 29:1672-1682 (2001).
Mendiratta et al., Intratumoral delivery of IL-12 gene by polyvinyl polymeric vector system to murine renal and colon carcinoma results in potent antitumor immunity, Gene Therapy, 6:833-839 (1999).
Menendez-Arias et al., Cytotoxic T-lymphocyte responses to HIV-1 reverse transcriptase (review), Virol. Lmmunol., 11:167-181 (1998).
Miyoshi et al., Development of a self-inactivating lentivirus vector, J. Virol., 72:8150-7 (1998).
Mukhopadhyay et al., A structural perspective of the flavivirus life cycle, Nature Rev. Microbio., 3:13-22 (2005).
Murugesan et al., Rheoswitch (Registered)-mediated regulation of IL-12 protein delivered using an adenoviral vector results in anti-tumor effects across a spectrum of tumor types, Ziopharm Oncology, Poster, 883:1 (2011).
Nastala et al., Recombinant IL-12 administration induces tumor regression in association with IFN-gamma production, J. Immunol., 153:1697-1706 (1994).
Navaratnarajah et al., Functional characterization of the Sindbis virus E2 glycoprotein by transposon linker-insertion mutagenesis, J. Virol., 363:124-147 (2007).
Nightingale et al., Transient gene expression by nonintegrating lentiviral vectors, Mol. Therapy, 13:1121-32 (2006).
Ohkawa et al., Control of the functional activity of an antisense RNA by a tetracycline-responsive derivative of the human U6 snRNA promoter, Hum. Gene. Therapy, 11:577-585 (2000).
Paule et al., Survey and summary: transcription by RNA polymerases I and III, Nucleic Acids Research, 28:1283-1298 (2000).
Pavlin et al., IL-12 based gene therapy in veterinary medicine, Journal of Translational Medicine, 10:234 (2012).
Pfeifer et al., Gene therapy: promises and problems, Annu. Rev. Genomics Hum. Genet., 2:177-211 (2001).
Philpott et al., Use of nonintegrating lentiviral vectors for gene therapy, Human Gene Therapy, 18:483-9 (2007).
Portielje et al., IL-12: a promising adjuvant for cancer vaccination, Cancer Immunol. Lmmunother., 52:133-144 (2003).
Portielje et al., Repeated administrations of interleukin (IL)-12 are associated with persistently elevated plasma levels of IL-10 and declining IFN-gamma, tumor necrosis factor-alpha, IL-6, and IL-8 responses, Clin. Cancer Res., 9:76-83 (2003).
Powell et al., Sequence and structural determinants required for priming of plus-strand DNA synthesis by the human immunodeficiency virus type 1 polypurine tract, J. Virol., 70:5288-96 (1996).
Promoters used to regulate gene expression, on Patent Lens web site, accessed (May 18, 2009).
Radkevich-Brown et al., Intratumoral DNA electroporation induces anti-tumor immunity and tumor regression, Cancer Immunol Immunother., 59:409-417 (2010).
Renkvist et al., A listing of human tumor antigens recognized by T cells, Cancer Immunology Immunotherapy, 50:3-15 (2001).
Sacco et al., Protective effect of a single interleukin-12 (IL-12) predose against the toxicity of subsequent chronic IL-12 in mice: role of cytokines and glucocorticoids, Blood, 90:4473-4479 (1997).
Sambrook et al., supra, 16.17-16.22.
Sasiain et al., Interferon-gamma (IFN-gamma) and tumour necrosis factor-alpha (TNF-alpha) are necessary in the early stages of induction of CD4 and CD8 cytotoxic T cells by *Mycobacterium leprae* heat shock protein (hsp) 65 kD., Clin. Exp. Immunol., 114:196-203 (1998).
Schatzlein AG., Non-viral vectors in cancer gene therapy: principles and progress, Anticancer Drugs, 12:275-304 (2001).
Singer-Sam et al., Sequence of the promoter region of the gene for human X-linked 3-phosphoglycerate kinase, Gene, 32:409-417 (1984).
Stoute et al., A preliminary evaluation of a recombinant circumsporozoite protein vaccine against Plasmodium falciparum malaria. RTS,S Malaria Vaccine Evaluation Group, N. Engl. J. Med., 336:86-91 (1997).
Strauss et al., The alphaviruses: gene expression, replication, and evolution, Microbial. Rev., 58:491-562:499-509 (1994).
Szymczak et al., Correction of multi-gene deficiency in vivo using a single 'self-cleaving' 2A peptide-based retroviral vector, Nat. Biotechnol., 22:589-594 (2004).
Taganov et al., MicroRNAs and immunity: tiny players in a big field, Immunity, 26:133-137 (2007).
Tahara et al., Effective eradication of established murine tumors with IL-12 gene therapy using a polycistronic retroviral vector, J. Immunol., 154:6466-6474 (1995).
Tatsumi et al., Administration of interleukin-12 enhances the therapeutic efficacy of dendritic cell-based tumor vaccines in mouse hepatocellular carcinoma, Cancer research 61:7563-7567 (2001).
Tatsumi et al., Intratumoral delivery of dendritic cells engineered to secrete both interleukin (IL)-12 and IL-18 effectively treats local and distant disease in association with broadly reactive Tc1-type immunity, Cancer Res., 63:6378-86 (2003).

(56) References Cited

OTHER PUBLICATIONS

Thomsen et al., Promoter-regulatory region of the major immediate early gene of human cytomegalovirus, PNAS., 81:659-63 (1984).
Tiemann et al., RNAi-based therapeutics-current status, challenges and prospects, EMBO. Mol. Med. 1:142-51 (2009).
Till et al., Depletion of Tregs for adoptive T-cell therapy using CD44 and CD137 as selection markers, Immunotherapy, 4:483-485 (2012).
Trang et al., The RNA Interference Resource of Applied Biosystems, Oncogene. Suppl., 2:S52 (2008).
Wang et al., High-affinity laminin receptor is a receptor for Sindbis virus in mammalian cells, J. Virol., 66:4992-5001 (1992).
Wei et al., Localized interleukin-12 delivery for immunotherapy of solid tumours, J. Cell. Mol. Med., 17:1465-1474 (2013).
West et al., Mutations in the endodomain of Sindbis virus glycoprotein E2 define sequences critical for virus assembly, J. Virol., 80:4458-4468, (2006).
Wigler et al., DNA-mediated transfer of the adenine phosphoribosyltransferase locus into mammalian cells, Proc. Natl. Acad. Sci., USA, 76:1373-76 (1979).
Written Opinion received for SG Patent Application No. 11201803546W, dated Aug. 5, 2019, 7 pages.
You et al., AAV2/IL-12 gene delivery into dendritic cells (DC) enhances CTL stimulation above other IL-12 applications, OncoImmunology, 1:847-855 (2012).
Zagozdzon et al., Effective chemo-immunotherapy of L1210 leukemia in vivo using interleukin-12 combined with doxorubicin but not with cyclophosphamide, paclitaxel or cisplatin, Int. J. Cancer, 77:720-727 (1998).
Apostolopoulos, Vasso et al., Targeting antigens to dendritic cell receptors for vaccine development, Journal of Drug Delivery, 2013, 1-22, ID 869718.
De Andrade Pereira, Bruna et al., Novel immunotherapeutic approaches in targeting dendritic cells with virus vectors. Discovery Medicine, 2015, 111-119, 20(109).
Lode, H.N. et al., Gene therapy with a single chain interleukin 12 fusion protein induces T celldependent protective immunity in a syngeneic model of murine neuroblastoma, Proc. Natl. Acad. Sci. USA, 1998, 2475-2480, 95(5).
Xiao, L. et al., A TLR4 agonist synergizes with dendritic cell-directed lentiviral vectors for inducing antigen-specific immune responses, Vaccine, 2012, 2570-2581, 30(15).
Zhou, S. et al., Depletion of CD4+ CD25+ Regulatory T Cells Promotes CCL2I-Mediated Antitumor Immunity, PLOS ONE, 2013, 1-13, 8(9) e73952.

\* cited by examiner

A

B

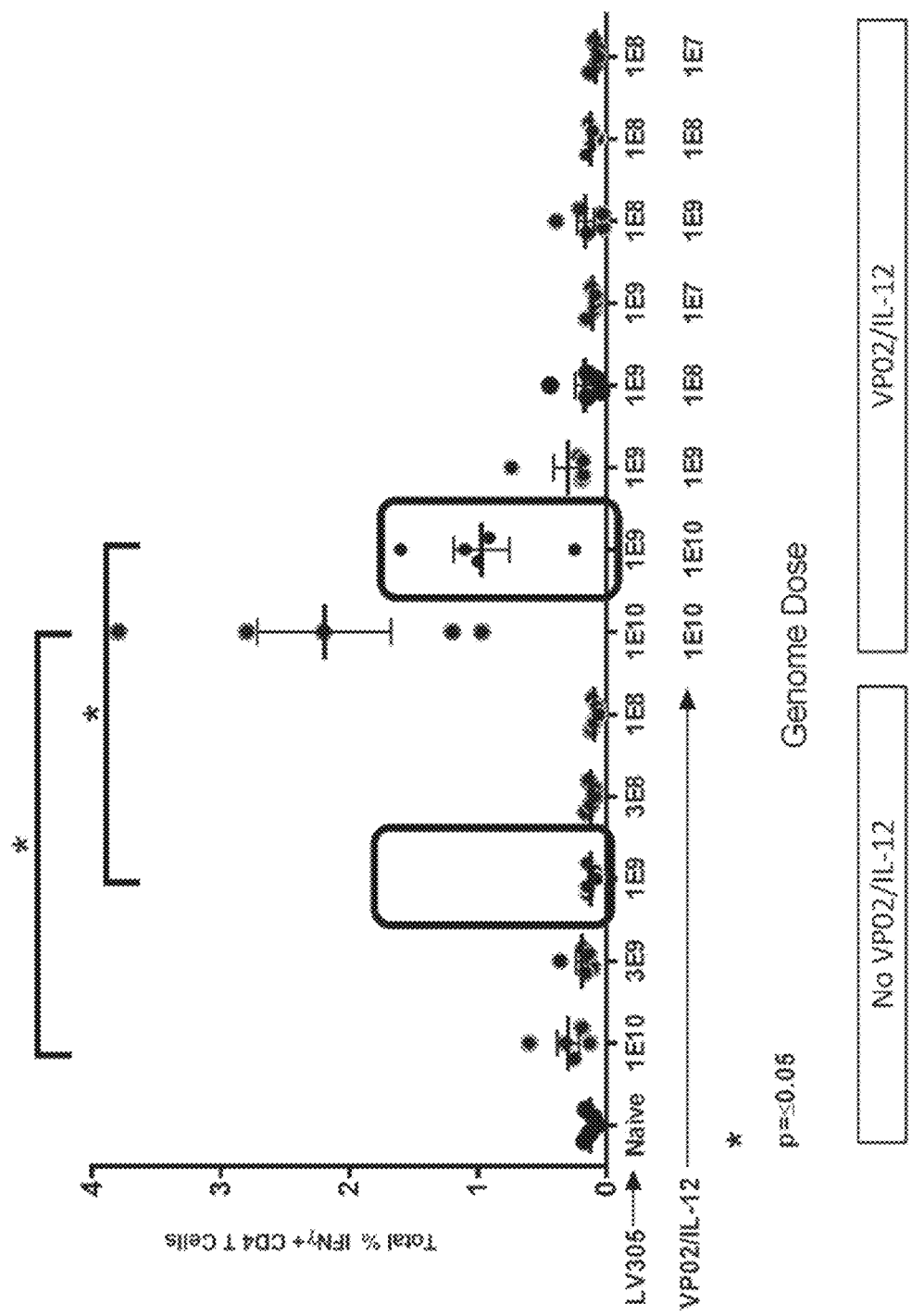

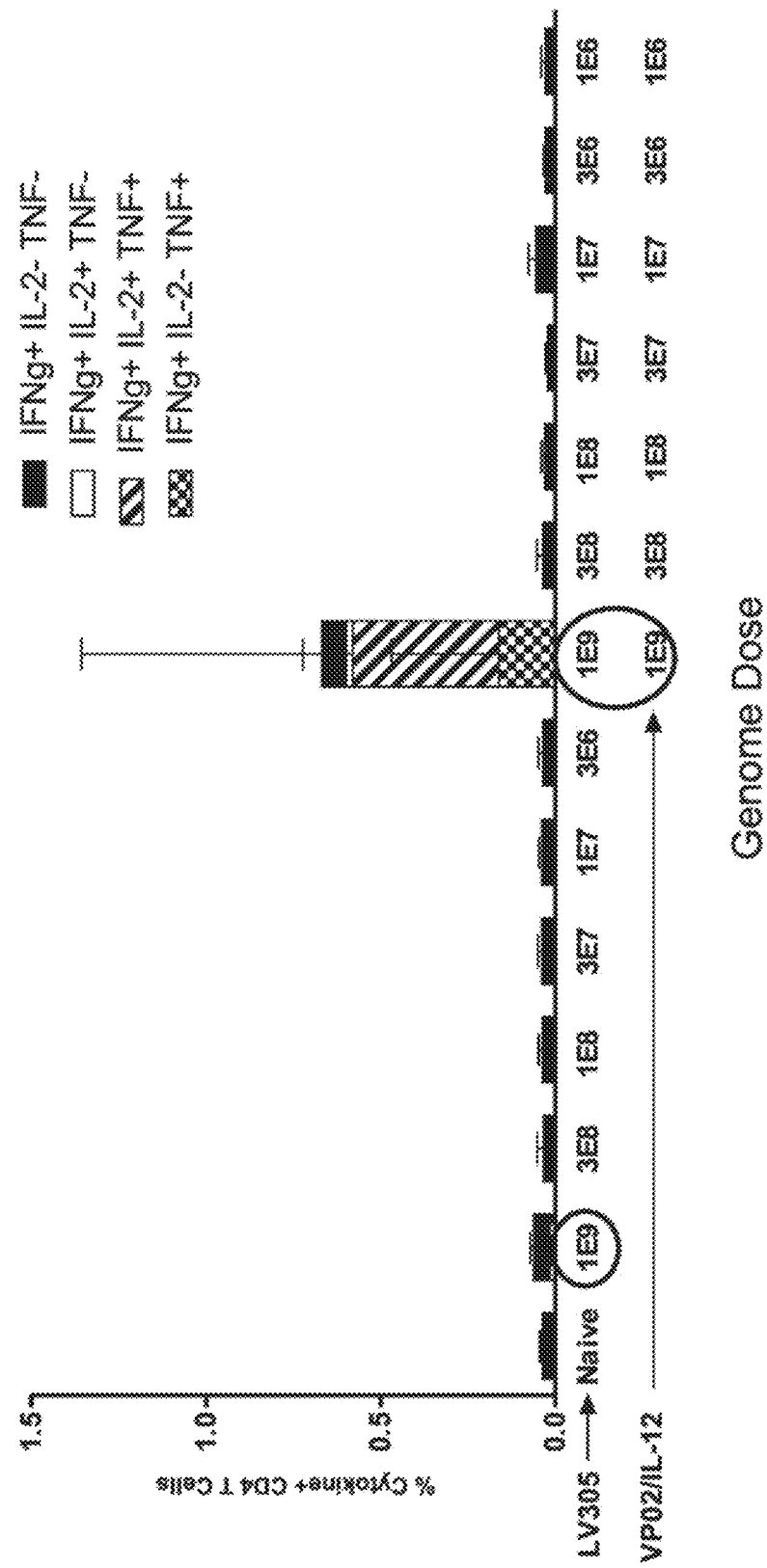

SEQUENCE LISTING

```
<160> NUMBER OF SEQ ID NOS: 28

<210> SEQ ID NO 1
<211> LENGTH: 423
<212> TYPE: PRT
<213> ORGANISM: Sindbis virus
<220> FEATURE:
<221> NAME/KEY: misc_feature
<222> LOCATION: (160)..(160)
<223> OTHER INFORMATION: Xaa can be any naturally occurring amino acid

<400> SEQUENCE: 1

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Lys Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
        115                 120                 125

Lys Ile Lys Pro Lys Phe Val Gly Arg Glu Lys Tyr Asp Leu Pro Pro
    130                 135                 140

Val His Gly Lys Lys Ile Pro Cys Thr Val Tyr Asp Arg Leu Lys Xaa
145                 150                 155                 160

Thr Thr Ala Gly Tyr Ile Thr Met His Arg Pro Arg Pro His Ala Tyr
                165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
    210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
            260                 265                 270

Ala Pro Asn Val Ile His Gly Phe Lys His Ile Ser Leu Gln Leu Asp
        275                 280                 285

Thr Asp His Leu Thr Leu Leu Thr Thr Arg Arg Leu Gly Ala Asn Pro
    290                 295                 300
```

-continued

```
Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
            325                 330                 335

Arg Val Tyr Ala Gln Glu Ser Ala Pro Gly Asp Pro His Gly Trp Pro
            340                 345                 350

His Glu Ile Val Gln His Tyr Tyr His Arg His Pro Val Tyr Thr Ile
            355                 360                 365

Leu Ala Val Ala Ser Ala Thr Val Ala Met Met Ile Gly Val Thr Val
            370                 375                 380

Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
            405                 410                 415

Cys Val Arg Ser Ala Asn Ala
            420

<210> SEQ ID NO 2
<211> LENGTH: 986
<212> TYPE: PRT
<213> ORGANISM: Sindbis virus

<400> SEQUENCE: 2

Met Ser Ala Ala Pro Leu Val Thr Ala Met

```
Tyr Ala Lys Pro Pro Ser Gly Lys Asn Ile Thr Tyr Glu Cys Lys Cys
            260                 265                 270

Gly Asp Tyr Lys Thr Gly Thr Val Ser Thr Arg Thr Glu Ile Thr Gly
            275                 280                 285

Cys Thr Ala Ile Lys Gln Cys Val Ala Tyr Lys Ser Asp Gln Thr Lys
290                 295                 300

Trp Val Phe Asn Ser Pro Asp Leu Ile Arg His Asp His Thr Ala
305                 310                 315                 320

Gln Gly Lys Leu His Leu Pro Phe Lys Leu Ile Pro Ser Thr Cys Met
                325                 330                 335

Val Pro Val Ala His Ala Pro Asn Val Ile His Gly Phe Lys His Ile
                340                 345                 350

Ser Leu Gln Leu Asp Thr Asp His Leu Thr Leu Leu Thr Arg Arg
            355                 360                 365

Leu Gly Ala Asn Pro Glu Pro Thr Thr Glu Trp Ile Val Gly Lys Thr
370                 375                 380

Val Arg Asn Phe Thr Val Asp Arg Asp Gly Leu Glu Tyr Ile Trp Gly
385                 390                 395                 400

Asn His Glu Pro Val Arg Val Tyr Ala Gln Glu Ser Ala Pro Gly Asp
                405                 410                 415

Pro His Gly Trp Pro His Glu Ile Val Gln His Tyr Tyr His Arg His
                420                 425                 430

Pro Val Tyr Thr Ile Leu Ala Val Ala Ser Ala Thr Val Ala Met Met
            435                 440                 445

Ile Gly Val Thr Val Ala Val Leu Cys Ala Cys Lys Ala Arg Arg Glu
            450                 455                 460

Cys Leu Thr Pro Tyr Ala Leu Ala Pro Asn Ala Val Ile Pro Thr Ser
465                 470                 475                 480

Leu Ala Leu Leu Cys Cys Val Arg Ser Ala Asn Ala Glu Thr Phe Thr
                485                 490                 495

Glu Thr Met Ser Tyr Leu Trp Ser Asn Ser Gln Pro Phe Phe Trp Val
            500                 505                 510

Gln Leu Cys Ile Pro Leu Ala Ala Phe Ile Val Leu Met Arg Cys Cys
            515                 520                 525

Ser Cys Cys Leu Pro Phe Leu Val Val Ala Gly Ala Tyr Leu Ala Lys
            530                 535                 540

Val Asp Ala Tyr Glu His Ala Thr Thr Val Pro Asn Val Pro Gln Ile
545                 550                 555                 560

Pro Tyr Lys Ala Leu Val Glu Arg Ala Gly Tyr Ala Pro Leu Asn Leu
                565                 570                 575

Glu Ile Thr Val Met Ser Ser Glu Val Leu Pro Ser Thr Asn Gln Glu
            580                 585                 590

Tyr Ile Thr Cys Lys Phe Thr Thr Val Val Pro Ser Pro Lys Ile Lys
            595                 600                 605

Cys Cys Gly Ser Leu Glu Cys Gln Pro Ala Ala His Ala Gly Tyr Thr
610                 615                 620

Cys Lys Val Phe Gly Gly Val Tyr Pro Phe Met Trp Gly Gly Ala Gln
625                 630                 635                 640

Cys Phe Cys Asp Ser Glu Asn Ser Gln Met Ser Glu Ala Tyr Val Glu
                645                 650                 655

Leu Ser Ala Asp Cys Ala Ser Asp His Ala Gln Ala Ile Lys Val His
            660                 665                 670
```

```
Thr Ala Ala Met Lys Val Gly Leu Arg Ile Val Tyr Gly Asn Thr Thr
            675                 680                 685
Ser Phe Leu Asp Val Tyr Val Asn Gly Val Thr Pro Gly Thr Ser Lys
        690                 695                 700
Asp Leu Lys Val Ile Ala Gly Pro Ile Ser Ala Ser Phe Thr Pro Phe
705                 710                 715                 720
Asp His Lys Val Val Ile His Arg Gly Leu Val Tyr Asn Tyr Asp Phe
                725                 730                 735
Pro Glu Tyr Gly Ala Met Lys Pro Gly Ala Phe Gly Asp Ile Gln Ala
            740                 745                 750
Thr Ser Leu Thr Ser Lys Asp Leu Ile Ala Ser Thr Asp Ile Arg Leu
        755                 760                 765
Leu Lys Pro Ser Ala Lys Asn Val His Val Pro Tyr Thr Gln Ala Ser
770                 775                 780
Ser Gly Phe Glu Met Trp Lys Asn Asn Ser Gly Arg Pro Leu Gln Glu
785                 790                 795                 800
Thr Ala Pro Phe Gly Cys Lys Ile Ala Val Asn Pro Leu Arg Ala Val
            805                 810                 815
Asp Cys Ser Tyr Gly Asn Ile Pro Ile Ser Ile Asp Ile Pro Asn Ala
        820                 825                 830
Ala Phe Ile Arg Thr Ser Asp Ala Pro Leu Val Ser Thr Val Lys Cys
            835                 840                 845
Glu Val Ser Glu Cys Thr Tyr Ser Ala Asp Phe Gly Gly Met Ala Thr
        850                 855                 860
Leu Gln Tyr Val Ser Asp Arg Glu Gly Gln Cys Pro Val His Ser His
865                 870                 875                 880
Ser Ser Thr Ala Thr Leu Gln Glu Ser Thr Val His Val Leu Glu Lys
            885                 890                 895
Gly Ala Val Thr Val His Phe Ser Thr Ala Ser Pro Gln Ala Asn Phe
        900                 905                 910
Ile Val Ser Leu Cys Gly Lys Lys Thr Thr Cys Asn Ala Glu Cys Lys
        915                 920                 925
Pro Pro Ala Asp His Ile Val Ser Thr Pro His Lys Asn Asp Gln Glu
930                 935                 940
Phe Gln Ala Ala Ile Ser Lys Thr Ser Trp Ser Trp Leu Phe Ala Leu
945                 950                 955                 960
Phe Gly Gly Ala Ser Ser Leu Leu Ile Ile Gly Leu Met Ile Phe Ala
                965                 970                 975
Cys Ser Met Met Leu Thr Ser Thr Arg Arg
            980                 985

<210> SEQ ID NO 3
<211> LENGTH: 982
<212> TYPE: PRT
<213> ORGANISM: Sindbis virus

<400> SEQUENCE: 3

Met Ser Ala Ala Pro Leu Val Thr Ala Met Cys Leu Leu Gly Asn Val
1               5                   10                  15
Ser Phe Pro Cys Asp Arg Pro Pro Thr Cys Tyr Thr Arg Glu Pro Ser
            20                  25                  30
Arg Ala Leu Asp Ile Leu Glu Glu Asn Val Asn His Glu Ala Tyr Asp
        35                  40                  45
Thr Leu Leu Asn Ala Ile Leu Arg Cys Gly Ser Ser Gly Arg Ser Lys
    50                  55                  60
```

```
Arg Ser Val Ile Asp Asp Phe Thr Leu Thr Ser Pro Tyr Leu Gly Thr
 65                  70                  75                  80

Cys Ser Tyr Cys His Thr Val Pro Cys Phe Ser Pro Val Lys Ile
                 85                  90                  95

Glu Gln Val Trp Asp Glu Ala Asp Asn Thr Ile Arg Ile Gln Thr
            100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Lys Glu Gly Thr
            130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Glu
210                 215                 220

Gly Thr Thr Ala Gly Tyr Ile Thr Met His Arg Pro Arg Pro His Ala
225                 230                 235                 240

Tyr Thr Ser Tyr Leu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
            275                 280                 285

Lys Gln Cys Val Ala Tyr Lys Ser Asp Gln Thr Lys Trp Val Phe Asn
            290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
            355                 360                 365

Pro Glu Pro Thr Thr Glu Trp Ile Val Gly Lys Thr Val Arg Asn Phe
            370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
            435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480
```

-continued

```
Cys Cys Val Arg Ser Ala Asn Ala Glu Thr Phe Thr Glu Thr Met Ser
            485                 490                 495

Tyr Leu Trp Ser Asn Ser Gln Pro Phe Phe Trp Val Gln Leu Cys Ile
        500                 505                 510

Pro Leu Ala Ala Phe Ile Val Leu Met Arg Cys Cys Ser Cys Cys Leu
    515                 520                 525

Pro Phe Leu Val Val Ala Gly Ala Tyr Leu Ala Lys Val Asp Ala Tyr
530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
        595                 600                 605

Leu Glu Cys Gln Pro Ala Ala His Ala Asp Tyr Thr Cys Lys Val Phe
    610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
        675                 680                 685

Val Tyr Val Asn Gly Val Thr Pro Gly Thr Ser Lys Asp Leu Lys Val
    690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
    770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895
```

```
Val His Phe Ser Thr Ala Ser Pro Gln Ala Asn Phe Ile Val Ser Leu
                900                 905                 910

Cys Gly Lys Lys Thr Thr Cys Asn Ala Glu Cys Lys Pro Ala Asp
                915                 920                 925

His Ile Val Ser Thr Pro His Lys Asn Asp Gln Glu Phe Gln Ala Ala
                930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
                980

<210> SEQ ID NO 4
<211> LENGTH: 982
<212> TYPE: PRT
<213> ORGANISM: Sindbis virus

<400> SEQUENCE: 4

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
                35                  40                  45

Thr Leu Leu Asn Ala Ile Leu Arg Cys Gly Ser Ser Gly Arg Ser Lys
            50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Glu Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
                180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Glu
210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
                260                 265                 270
```

-continued

```
Thr Gly Thr Val Ser Thr Arg Thr Glu Ile Thr Gly Cys Thr Ala Ile
    275                 280                 285
Lys Gln Cys Val Ala Tyr Lys Ser Asp Gln Thr Lys Trp Val Phe Asn
    290                 295                 300
Ser Pro Asp Leu Ile Arg His Asp His Thr Ala Gln Gly Lys Leu
305                 310                 315                 320
His Leu Pro Phe Lys Leu Ile Pro Ser Thr Cys Met Val Pro Val Ala
                325                 330                 335
His Ala Pro Asn Val Ile His Gly Phe Lys His Ile Ser Leu Gln Leu
            340                 345                 350
Asp Thr Asp His Leu Thr Leu Leu Thr Thr Arg Arg Leu Gly Ala Asn
            355                 360                 365
Pro Glu Pro Thr Thr Glu Trp Ile Val Gly Lys Thr Val Arg Asn Phe
    370                 375                 380
Thr Val Asp Arg Asp Gly Leu Glu Tyr Ile Trp Gly Asn His Glu Pro
385                 390                 395                 400
Val Arg Val Tyr Ala Gln Glu Ser Ala Pro Gly Asp Pro His Gly Trp
                405                 410                 415
Pro His Glu Ile Val Gln His Tyr Tyr His Arg His Pro Val Tyr Thr
            420                 425                 430
Ile Leu Ala Val Ala Ser Ala Thr Val Ala Met Met Ile Gly Val Thr
            435                 440                 445
Val Ala Val Leu Cys Ala Cys Lys Ala Arg Arg Glu Cys Leu Thr Pro
    450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala Glu Thr Phe Thr Glu Thr Met Ser
                485                 490                 495
Tyr Leu Trp Ser Asn Ser Gln Pro Phe Phe Trp Val Gln Leu Cys Ile
            500                 505                 510
Pro Leu Ala Ala Phe Ile Val Leu Met Arg Cys Cys Ser Cys Cys Leu
            515                 520                 525
Pro Phe Leu Val Val Ala Gly Ala Tyr Leu Ala Lys Val Asp Ala Tyr
    530                 535                 540
Glu His Ala Thr Thr Val Pro Asn Val Pro Gln Ile Pro Tyr Lys Ala
545                 550                 555                 560
Leu Val Glu Arg Ala Gly Tyr Ala Pro Leu Asn Leu Glu Ile Thr Val
                565                 570                 575
Met Ser Ser Glu Val Leu Pro Ser Thr Asn Gln Glu Tyr Ile Thr Cys
            580                 585                 590
Lys Phe Thr Thr Val Val Pro Ser Pro Lys Ile Lys Cys Cys Gly Ser
            595                 600                 605
Leu Glu Cys Gln Pro Ala Ala His Ala Asp Tyr Thr Cys Lys Val Phe
    610                 615                 620
Gly Gly Val Tyr Pro Phe Met Trp Gly Gly Ala Gln Cys Phe Cys Asp
625                 630                 635                 640
Ser Glu Asn Ser Gln Met Ser Glu Ala Tyr Val Glu Leu Ser Ala Asp
                645                 650                 655
Cys Ala Ser Asp His Ala Gln Ala Ile Lys Val His Thr Ala Ala Met
            660                 665                 670
Lys Val Gly Leu Arg Ile Val Tyr Gly Asn Thr Thr Ser Phe Leu Asp
            675                 680                 685
```

```
Val Tyr Val Asn Gly Val Thr Pro Gly Thr Ser Lys Asp Leu Lys Val
    690             695                 700

Ile Ala Gly Pro Ile Ser Ala Ser Phe Thr Pro Phe Asp His Lys Val
705             710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
        915                 920                 925

His Ile Val Ser Thr Pro His Lys Asn Asp Gln Glu Phe Gln Ala Ala
    930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980

<210> SEQ ID NO 5
<211> LENGTH: 980
<212> TYPE: PRT
<213> ORGANISM: Sindbis virus

<400> SEQUENCE: 5

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80
```

-continued

```
Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Lys Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Thr
    210                 215                 220

Thr Ala Gly Tyr Ile Thr Met His Arg Pro Arg Pro His Ala Tyr Thr
225                 230                 235                 240

Ser Tyr Leu Glu Glu Ser Ser Gly Lys Val Tyr Ala Lys Pro Pro Ser
                245                 250                 255

Gly Lys Asn Ile Thr Tyr Glu Cys Lys Cys Gly Asp Tyr Lys Thr Gly
            260                 265                 270

Thr Val Ser Thr Arg Thr Glu Ile Thr Gly Cys Thr Ala Ile Lys Gln
        275                 280                 285

Cys Val Ala Tyr Lys Ser Asp Gln Thr Lys Trp Val Phe Asn Ser Pro
    290                 295                 300

Asp Leu Ile Arg His Asp Asp His Thr Ala Gln Gly Lys Leu His Leu
305                 310                 315                 320

Pro Phe Lys Leu Ile Pro Ser Thr Cys Met Val Pro Val Ala His Ala
                325                 330                 335

Pro Asn Val Ile His Gly Phe Lys His Ile Ser Leu Gln Leu Asp Thr
            340                 345                 350

Asp His Leu Thr Leu Leu Thr Thr Arg Arg Leu Gly Ala Asn Pro Glu
        355                 360                 365

Pro Thr Thr Glu Trp Ile Val Gly Lys Thr Val Arg Asn Phe Thr Val
    370                 375                 380

Asp Arg Asp Gly Leu Glu Tyr Ile Trp Gly Asn His Glu Pro Val Arg
385                 390                 395                 400

Val Tyr Ala Gln Glu Ser Ala Pro Gly Asp Pro His Gly Trp Pro His
                405                 410                 415

Glu Ile Val Gln His Tyr Tyr His Arg His Pro Val Tyr Thr Ile Leu
            420                 425                 430

Ala Val Ala Ser Ala Thr Val Ala Met Met Ile Gly Val Thr Val Ala
        435                 440                 445

Val Leu Cys Ala Cys Lys Ala Arg Arg Glu Cys Leu Thr Pro Tyr Ala
    450                 455                 460

Leu Ala Pro Asn Ala Val Ile Pro Thr Ser Leu Ala Leu Leu Cys Cys
465                 470                 475                 480

Val Arg Ser Ala Asn Ala Glu Thr Phe Thr Glu Thr Met Ser Tyr Leu
                485                 490                 495
```

```
Trp Ser Asn Ser Gln Pro Phe Phe Trp Val Gln Leu Cys Ile Pro Leu
            500                 505                 510

Ala Ala Phe Ile Val Leu Met Arg Cys Cys Ser Cys Cys Leu Pro Phe
            515                 520                 525

Leu Val Val Ala Gly Ala Tyr Leu Ala Lys Val Asp Ala Tyr Glu His
            530                 535                 540

Ala Thr Thr Val Pro Asn Val Pro Gln Ile Pro Tyr Lys Ala Leu Val
545                 550                 555                 560

Glu Arg Ala Gly Tyr Ala Pro Leu Asn Leu Glu Ile Thr Val Met Ser
                565                 570                 575

Ser Glu Val Leu Pro Ser Thr Asn Gln Glu Tyr Ile Thr Cys Lys Phe
            580                 585                 590

Thr Thr Val Val Pro Ser Pro Lys Ile Lys Cys Cys Gly Ser Leu Glu
            595                 600                 605

Cys Gln Pro Ala Ala His Ala Asp Tyr Thr Cys Lys Val Phe Gly Gly
            610                 615                 620

Val Tyr Pro Phe Met Trp Gly Ala Gln Cys Phe Cys Asp Ser Glu
625                 630                 635                 640

Asn Ser Gln Met Ser Glu Ala Tyr Val Glu Leu Ser Ala Asp Cys Ala
                645                 650                 655

Ser Asp His Ala Gln Ala Ile Lys Val His Thr Ala Ala Met Lys Val
            660                 665                 670

Gly Leu Arg Ile Val Tyr Gly Asn Thr Thr Ser Phe Leu Asp Val Tyr
            675                 680                 685

Val Asn Gly Val Thr Pro Gly Thr Ser Lys Asp Leu Lys Val Ile Ala
690                 695                 700

Gly Pro Ile Ser Ala Ser Phe Thr Pro Phe Asp His Lys Val Val Ile
705                 710                 715                 720

His Arg Gly Leu Val Tyr Asn Tyr Asp Phe Pro Glu Tyr Gly Ala Met
                725                 730                 735

Lys Pro Gly Ala Phe Gly Asp Ile Gln Ala Thr Ser Leu Thr Ser Lys
            740                 745                 750

Asp Leu Ile Ala Ser Thr Asp Ile Arg Leu Leu Lys Pro Ser Ala Lys
            755                 760                 765

Asn Val His Val Pro Tyr Thr Gln Ala Ser Ser Gly Phe Glu Met Trp
            770                 775                 780

Lys Asn Asn Ser Gly Arg Pro Leu Gln Glu Thr Ala Pro Phe Gly Cys
785                 790                 795                 800

Lys Ile Ala Val Asn Pro Leu Arg Ala Val Asp Cys Ser Tyr Gly Asn
                805                 810                 815

Ile Pro Ile Ser Ile Asp Ile Pro Asn Ala Ala Phe Ile Arg Thr Ser
            820                 825                 830

Asp Ala Pro Leu Val Ser Thr Val Lys Cys Glu Val Ser Glu Cys Thr
            835                 840                 845

Tyr Ser Ala Asp Phe Gly Gly Met Ala Thr Leu Gln Tyr Val Ser Asp
850                 855                 860

Arg Glu Gly Gln Cys Pro Val His Ser His Ser Ser Thr Ala Thr Leu
865                 870                 875                 880

Gln Glu Ser Thr Val His Val Leu Glu Lys Gly Ala Val Thr Val His
                885                 890                 895

Phe Ser Thr Ala Ser Pro Gln Ala Asn Phe Ile Val Ser Leu Cys Gly
            900                 905                 910
```

```
Lys Lys Thr Thr Cys Asn Ala Glu Cys Lys Pro Pro Ala Asp His Ile
        915                 920                 925

Val Ser Thr Pro His Lys Asn Asp Gln Glu Phe Gln Ala Ala Ile Ser
        930                 935                 940

Lys Thr Ser Trp Ser Trp Leu Phe Ala Leu Phe Gly Gly Ala Ser Ser
945                 950                 955                 960

Leu Leu Ile Ile Gly Leu Met Ile Phe Ala Cys Ser Met Met Leu Thr
            965                 970                 975

Ser Thr Arg Arg
            980

<210> SEQ ID NO 6
<211> LENGTH: 981
<212> TYPE: PRT
<213> ORGANISM: Sindbis virus

<400> SEQUENCE: 6

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Glu Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
    210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285
```

```
Gln Cys Val Ala Tyr Lys Ser Asp Gln Thr Lys Trp Val Phe Asn Ser
    290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
                340                 345                 350

Thr Asp His Leu Thr Leu Leu Thr Thr Arg Arg Leu Gly Ala Asn Pro
        355                 360                 365

Glu Pro Thr Thr Glu Trp Ile Val Gly Lys Thr Val Arg Asn Phe Thr
    370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr His Arg His Pro Val Tyr Thr Ile
                420                 425                 430

Leu Ala Val Ala Ser Ala Thr Val Ala Met Met Ile Gly Val Thr Val
                435                 440                 445

Ala Val Leu Cys Ala Cys Lys Ala Arg Arg Glu Cys Leu Thr Pro Tyr
450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
                500                 505                 510

Leu Ala Ala Phe Ile Val Leu Met Arg Cys Cys Ser Cys Cys Leu Pro
                515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
                580                 585                 590

Phe Thr Thr Val Val Pro Ser Pro Lys Ile Lys Cys Cys Gly Ser Leu
            595                 600                 605

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
                660                 665                 670

Val Gly Leu Arg Ile Val Tyr Gly Asn Thr Thr Ser Phe Leu Asp Val
                675                 680                 685

Tyr Val Asn Gly Val Thr Pro Gly Thr Ser Lys Asp Leu Lys Val Ile
    690                 695                 700
```

```
Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
            725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
        755                 760                 765

Lys Asn Val His Val Pro Tyr Thr Gln Ala Ser Ser Gly Phe Glu Met
    770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
    850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile
    930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 7
<211> LENGTH: 982
<212> TYPE: PRT
<213> ORGANISM: Sindbis virus

<400> SEQUENCE: 7

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95
```

```
Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Lys Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Glu
            210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
            275                 280                 285

Lys Gln Cys Val Ala Tyr Lys Ser Asp Gln Thr Lys Trp Val Phe Asn
            290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
            355                 360                 365

Pro Glu Pro Thr Thr Glu Trp Ile Val Gly Lys Thr Val Arg Asn Phe
370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
            435                 440                 445

Val Ala Val Leu Cys Ala Cys Lys Ala Arg Arg Glu Cys Leu Thr Pro
            450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510
```

```
Pro Leu Ala Ala Phe Ile Val Leu Met Arg Cys Cys Ser Cys Cys Leu
            515                 520                 525
Pro Phe Leu Val Val Ala Gly Ala Tyr Leu Ala Lys Val Asp Ala Tyr
        530                 535                 540
Glu His Ala Thr Thr Val Pro Asn Val Pro Gln Ile Pro Tyr Lys Ala
545                 550                 555                 560
Leu Val Glu Arg Ala Gly Tyr Ala Pro Leu Asn Leu Glu Ile Thr Val
                565                 570                 575
Met Ser Ser Glu Val Leu Pro Ser Thr Asn Gln Glu Tyr Ile Thr Cys
            580                 585                 590
Lys Phe Thr Thr Val Val Pro Ser Pro Lys Ile Lys Cys Cys Gly Ser
        595                 600                 605
Leu Glu Cys Gln Pro Ala Ala His Ala Asp Tyr Thr Cys Lys Val Phe
610                 615                 620
Gly Gly Val Tyr Pro Phe Met Trp Gly Gly Ala Gln Cys Phe Cys Asp
625                 630                 635                 640
Ser Glu Asn Ser Gln Met Ser Glu Ala Tyr Val Glu Leu Ser Ala Asp
                645                 650                 655
Cys Ala Ser Asp His Ala Gln Ala Ile Lys Val His Thr Ala Ala Met
            660                 665                 670
Lys Val Gly Leu Arg Ile Val Tyr Gly Asn Thr Thr Ser Phe Leu Asp
        675                 680                 685
Val Tyr Val Asn Gly Val Thr Pro Gly Thr Ser Lys Asp Leu Lys Val
690                 695                 700
Ile Ala Gly Pro Ile Ser Ala Ser Phe Thr Pro Phe Asp His Lys Val
705                 710                 715                 720
Val Ile His Arg Gly Leu Val Tyr Asn Tyr Asp Phe Pro Glu Tyr Gly
                725                 730                 735
Ala Met Lys Pro Gly Ala Phe Gly Asp Ile Gln Ala Thr Ser Leu Thr
            740                 745                 750
Ser Lys Asp Leu Ile Ala Ser Thr Asp Ile Arg Leu Leu Lys Pro Ser
        755                 760                 765
Ala Lys Asn Val His Val Pro Tyr Thr Gln Ala Ser Ser Gly Phe Glu
770                 775                 780
Met Trp Lys Asn Asn Ser Gly Arg Pro Leu Gln Glu Thr Ala Pro Phe
785                 790                 795                 800
Gly Cys Lys Ile Ala Val Asn Pro Leu Arg Ala Val Asp Cys Ser Tyr
                805                 810                 815
Gly Asn Ile Pro Ile Ser Ile Asp Ile Pro Asn Ala Ala Phe Ile Arg
            820                 825                 830
Thr Ser Asp Ala Pro Leu Val Ser Thr Val Lys Cys Glu Val Ser Glu
        835                 840                 845
Cys Thr Tyr Ser Ala Asp Phe Gly Gly Met Ala Thr Leu Gln Tyr Val
850                 855                 860
Ser Asp Arg Glu Gly Gln Cys Pro Val His Ser His Ser Ser Thr Ala
865                 870                 875                 880
Thr Leu Gln Glu Ser Thr Val His Val Leu Glu Lys Gly Ala Val Thr
                885                 890                 895
Val His Phe Ser Thr Ala Ser Pro Gln Ala Asn Phe Ile Val Ser Leu
            900                 905                 910
Cys Gly Lys Lys Thr Thr Cys Asn Ala Glu Cys Lys Pro Pro Ala Asp
        915                 920                 925
```

```
His Ile Val Ser Thr Pro His Lys Asn Asp Gln Glu Phe Gln Ala Ala
        930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
            965                 970                 975

Leu Thr Ser Thr Arg Arg
            980

<210> SEQ ID NO 8
<211> LENGTH: 981
<212> TYPE: PRT
<213> ORGANISM: Sindbis virus

<400> SEQUENCE: 8

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Lys Gln Asp His Thr Val Lys Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
290                 295                 300
```

-continued

```
Pro Asp Leu Ile Arg His Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

Thr Asp His Leu Thr Leu Leu Thr Thr Arg Arg Leu Gly Ala Asn Pro
        355                 360                 365

Glu Pro Thr Thr Glu Trp Ile Val Gly Lys Thr Val Arg Asn Phe Thr
    370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
        435                 440                 445

Ala Val Leu Cys Ala Cys Lys Ala Arg Arg Glu Cys Leu Thr Pro Tyr
450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
        515                 520                 525

Phe Leu Val Val Ala Gly Ala Tyr Leu Ala Lys Val Asp Ala Tyr Glu
    530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
        595                 600                 605

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
        675                 680                 685

Tyr Val Asn Gly Val Thr Pro Gly Thr Ser Lys Asp Leu Lys Val Ile
    690                 695                 700

Ala Gly Pro Ile Ser Ala Ser Phe Thr Pro Phe Asp His Lys Val Val
705                 710                 715                 720
```

```
Ile His Arg Gly Leu Val Tyr Asn Tyr Asp Phe Pro Glu Tyr Gly Ala
            725                 730                 735

Met Lys Pro Gly Ala Phe Gly Asp Ile Gln Ala Thr Ser Leu Thr Ser
        740                 745                 750

Lys Asp Leu Ile Ala Ser Thr Asp Ile Arg Leu Leu Lys Pro Ser Ala
            755                 760                 765

Lys Asn Val His Val Pro Tyr Thr Gln Ala Ser Ser Gly Phe Glu Met
770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
            805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
        850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile
            930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
            965                 970                 975

Thr Ser Thr Arg Arg
            980

<210> SEQ ID NO 9
<211> LENGTH: 982
<212> TYPE: PRT
<213> ORGANISM: Sindbis virus

<400> SEQUENCE: 9

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110
```

```
Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Glu Glu Gly Thr
        130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
        515                 520                 525
```

```
Pro Phe Leu Val Val Ala Gly Ala Tyr Leu Ala Lys Val Asp Ala Tyr
530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
            565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
        595                 600                 605

Leu Glu Cys Gln Pro Ala Ala His Ala Asp Tyr Thr Cys Lys Val Phe
    610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
                660                 665                 670

Lys Val Gly Leu Arg Ile Val Tyr Gly Asn Thr Thr Ser Phe Leu Asp
            675                 680                 685

Val Tyr Val Asn Gly Val Thr Pro Gly Thr Ser Lys Asp Leu Lys Val
690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
            725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
    770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
                820                 825                 830

Thr Ser Asp Ala Pro Leu Val Ser Thr Val Lys Cys Glu Val Ser Glu
            835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
                900                 905                 910

Cys Gly Lys Lys Thr Thr Cys Asn Ala Glu Cys Lys Pro Pro Ala Asp
            915                 920                 925

His Ile Val Ser Thr Pro His Lys Asn Asp Gln Glu Phe Gln Ala Ala
            930                 935                 940
```

```
Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980

<210> SEQ ID NO 10
<211> LENGTH: 981
<212> TYPE: PRT
<213> ORGANISM: Sindbis virus

<400> SEQUENCE: 10

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Glu Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
195                 200                 205

Pro Val His Gly Lys Lys Ile Pro Cys Thr Val Tyr Asp Arg Leu Glu
210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
                260                 265                 270

Gly Thr Val Ser Thr Arg Thr Glu Ile Thr Gly Cys Thr Ala Ile Lys
            275                 280                 285

Gln Cys Val Ala Tyr Lys Ser Asp Gln Thr Lys Trp Val Phe Asn Ser
        290                 295                 300

Pro Asp Leu Ile Arg His Asp Asp His Thr Ala Gln Gly Lys Leu His
305                 310                 315                 320
```

```
Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

Thr Asp His Leu Thr Leu Leu Thr Arg Arg Leu Gly Ala Asn Asn Pro
        355                 360                 365

Glu Pro Thr Thr Glu Trp Ile Val Gly Lys Thr Val Arg Asn Phe Thr
    370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
        435                 440                 445

Ala Val Leu Cys Ala Cys Lys Ala Arg Arg Glu Cys Leu Thr Pro Tyr
    450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
        515                 520                 525

Phe Leu Val Val Ala Gly Ala Tyr Leu Ala Lys Val Asp Ala Tyr Glu
    530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
        595                 600                 605

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
        675                 680                 685

Tyr Val Asn Gly Val Thr Pro Gly Thr Ser Lys Asp Leu Lys Val Ile
    690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735
```

```
Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
        755                 760                 765

Lys Asn Val His Val Pro Tyr Thr Gln Ala Ser Ser Gly Phe Glu Met
        770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
        850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile
        930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 11
<211> LENGTH: 982
<212> TYPE: PRT
<213> ORGANISM: Sindbis virus

<400> SEQUENCE: 11

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125
```

```
Tyr Arg Tyr Met Ser Leu Lys Gln Asp His Thr Val Glu Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
                180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Lys
210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
            275                 280                 285

Lys Gln Cys Val Ala Tyr Lys Ser Asp Gln Thr Lys Trp Val Phe Asn
290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
            355                 360                 365

Pro Glu Pro Thr Thr Glu Trp Ile Val Gly Lys Thr Val Arg Asn Phe
370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
            435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
            515                 520                 525

Pro Phe Leu Val Val Ala Gly Ala Tyr Leu Ala Lys Val Asp Ala Tyr
530                 535                 540
```

```
Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
        595                 600                 605

Leu Glu Cys Gln Pro Ala Ala His Ala Asp Tyr Thr Cys Lys Val Phe
    610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
        675                 680                 685

Val Tyr Val Asn Gly Val Thr Pro Gly Thr Ser Lys Asp Leu Lys Val
    690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
    770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
        915                 920                 925

His Ile Val Ser Thr Pro His Lys Asn Asp Gln Glu Phe Gln Ala Ala
    930                 935                 940

Ile Ser Lys Thr Ser Trp Ser Trp Leu Phe Ala Leu Phe Gly Gly Ala
945                 950                 955                 960
```

```
Ser Ser Leu Leu Ile Ile Gly Leu Met Ile Phe Ala Cys Ser Met Met
            965                 970                 975

Leu Thr Ser Thr Arg Arg
            980

<210> SEQ ID NO 12
<211> LENGTH: 981
<212> TYPE: PRT
<213> ORGANISM: Sindbis virus

<400> SEQUENCE: 12

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
        50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Glu Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
    290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335
```

```
Ala Pro Asn Val Ile His Gly Phe Lys His Ile Ser Leu Gln Leu Asp
            340                 345                 350

Thr Asp His Leu Thr Leu Leu Thr Arg Arg Leu Gly Ala Asn Pro
            355                 360                 365

Glu Pro Thr Thr Glu Trp Ile Val Gly Lys Thr Val Arg Asn Phe Thr
370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
            405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
            435                 440                 445

Ala Val Leu Cys Ala Cys Lys Ala Arg Arg Glu Cys Leu Thr Pro Tyr
            450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
            485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
            515                 520                 525

Phe Leu Val Val Ala Gly Ala Tyr Leu Ala Lys Val Asp Ala Tyr Glu
            530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
            565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
            595                 600                 605

Glu Cys Gln Pro Ala Ala His Ala Asp Tyr Thr Cys Lys Val Phe Gly
610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
            645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
            675                 680                 685

Tyr Val Asn Gly Val Thr Pro Gly Thr Ser Lys Asp Leu Lys Val Ile
            690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
            725                 730                 735

Met Lys Pro Gly Ala Phe Gly Asp Ile Gln Ala Thr Ser Leu Thr Ser
            740                 745                 750
```

```
Lys Asp Leu Ile Ala Ser Thr Asp Ile Arg Leu Leu Lys Pro Ser Ala
            755                 760                 765

Lys Asn Val His Val Pro Tyr Thr Gln Ala Ser Ser Gly Phe Glu Met
770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
            835                 840                 845

Thr Tyr Ser Ala Asp Phe Gly Gly Met Ala Thr Leu Gln Tyr Val Ser
            850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
                900                 905                 910

Gly Lys Lys Thr Thr Cys Asn Ala Glu Cys Lys Pro Pro Ala Asp His
            915                 920                 925

Ile Val Ser Thr Pro His Lys Asn Asp Gln Glu Phe Gln Ala Ala Ile
            930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 13
<211> LENGTH: 982
<212> TYPE: PRT
<213> ORGANISM: Sindbis virus

<400> SEQUENCE: 13

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
        50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Lys Glu Gly Thr
        130                 135                 140
```

-continued

```
Met Asp Asp Ile Lys Ile Ser Thr Ser Gly Pro Cys Arg Arg Leu Ser
145                 150                 155                 160

Tyr Lys Gly Tyr Phe Leu Ala Lys Cys Pro Pro Gly Asp Ser Val
            165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Lys
            210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
            245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
            275                 280                 285

Lys Gln Cys Val Ala Tyr Lys Ser Asp Gln Thr Lys Trp Val Phe Asn
290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
            325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
            355                 360                 365

Pro Glu Pro Thr Thr Glu Trp Ile Val Gly Lys Thr Val Arg Asn Phe
370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
            405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
            435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
            485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
            515                 520                 525

Pro Phe Leu Val Val Ala Gly Ala Tyr Leu Ala Lys Val Asp Ala Tyr
            530                 535                 540

Glu His Ala Thr Thr Val Pro Asn Val Pro Gln Ile Pro Tyr Lys Ala
545                 550                 555                 560
```

```
Leu Val Glu Arg Ala Gly Tyr Ala Pro Leu Asn Leu Glu Ile Thr Val
            565                 570                 575

Met Ser Ser Glu Val Leu Pro Ser Thr Asn Gln Glu Tyr Ile Thr Cys
        580                 585                 590

Lys Phe Thr Thr Val Val Pro Ser Pro Lys Ile Lys Cys Cys Gly Ser
            595                 600                 605

Leu Glu Cys Gln Pro Ala Ala His Ala Asp Tyr Thr Cys Lys Val Phe
        610                 615                 620

Gly Gly Val Tyr Pro Phe Met Trp Gly Ala Gln Cys Phe Cys Asp
625                 630                 635                 640

Ser Glu Asn Ser Gln Met Ser Glu Ala Tyr Val Glu Leu Ser Ala Asp
            645                 650                 655

Cys Ala Ser Asp His Ala Gln Ala Ile Lys Val His Thr Ala Ala Met
        660                 665                 670

Lys Val Gly Leu Arg Ile Val Tyr Gly Asn Thr Thr Ser Phe Leu Asp
            675                 680                 685

Val Tyr Val Asn Gly Val Thr Pro Gly Thr Ser Lys Asp Leu Lys Val
        690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
            725                 730                 735

Ala Met Lys Pro Gly Ala Phe Gly Asp Ile Gln Ala Ser Ser Leu Thr
        740                 745                 750

Ser Lys Asp Leu Ile Ala Ser Thr Asp Ile Arg Leu Leu Lys Pro Ser
            755                 760                 765

Ala Lys Asn Val His Val Pro Tyr Thr Gln Ala Ser Ser Gly Phe Glu
        770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
            805                 810                 815

Gly Asn Ile Pro Ile Ser Ile Asp Ile Pro Asn Ala Ala Phe Ile Arg
        820                 825                 830

Thr Ser Asp Ala Pro Leu Val Ser Thr Val Lys Cys Glu Val Ser Glu
            835                 840                 845

Cys Thr Tyr Ser Ala Asp Phe Gly Gly Met Ala Thr Leu Gln Tyr Val
        850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
            885                 890                 895

Val His Phe Ser Thr Ala Ser Pro Gln Ala Asn Phe Ile Val Ser Leu
        900                 905                 910

Cys Gly Lys Lys Thr Thr Cys Asn Ala Glu Cys Lys Pro Pro Ala Asp
            915                 920                 925

His Ile Val Ser Thr Pro His Lys Asn Asp Gln Glu Phe Gln Ala Ala
        930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
            965                 970                 975
```

Leu Thr Ser Thr Arg Arg
            980

<210> SEQ ID NO 14
<211> LENGTH: 981
<212> TYPE: PRT
<213> ORGANISM: Sindbis virus

<400> SEQUENCE: 14

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Lys Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
    290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

-continued

Thr Asp His Leu Thr Leu Leu Thr Thr Arg Arg Leu Gly Ala Asn Pro
       355                 360                 365

Glu Pro Thr Thr Glu Trp Ile Val Gly Lys Thr Val Arg Asn Phe Thr
370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
                420                 425                 430

Leu Ala Val Ala Ser Ala Thr Val Ala Met Met Ile Gly Val Thr Val
                435                 440                 445

Ala Val Leu Cys Ala Cys Lys Ala Arg Arg Glu Cys Leu Thr Pro Tyr
       450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
                500                 505                 510

Leu Ala Ala Phe Ile Val Leu Met Arg Cys Cys Ser Cys Cys Leu Pro
                515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
                580                 585                 590

Phe Thr Thr Val Val Pro Ser Pro Lys Ile Lys Cys Cys Gly Ser Leu
                595                 600                 605

Glu Cys Gln Pro Ala Ala His Ala Asp Tyr Thr Cys Lys Val Phe Gly
       610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
                660                 665                 670

Val Gly Leu Arg Ile Val Tyr Gly Asn Thr Thr Ser Phe Leu Asp Val
                675                 680                 685

Tyr Val Asn Gly Val Thr Pro Gly Thr Ser Lys Asp Leu Lys Val Ile
690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
                740                 745                 750

Lys Asp Leu Ile Ala Ser Thr Asp Ile Arg Leu Leu Lys Pro Ser Ala
                755                 760                 765

-continued

Lys Asn Val His Val Pro Tyr Thr Gln Ala Ser Ser Gly Phe Glu Met
770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
            805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
            835                 840                 845

Thr Tyr Ser Ala Asp Phe Gly Gly Met Ala Thr Leu Gln Tyr Val Ser
850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
            885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
            915                 920                 925

Ile Val Ser Thr Pro His Lys Asn Asp Gln Glu Phe Gln Ala Ala Ile
930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
            965                 970                 975

Thr Ser Thr Arg Arg
            980

<210> SEQ ID NO 15
<211> LENGTH: 982
<212> TYPE: PRT
<213> ORGANISM: Sindbis virus

<400> SEQUENCE: 15

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
            85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Glu Glu Gly Thr
            130                 135                 140

Met Asp Asp Ile Lys Ile Ser Thr Ser Gly Pro Cys Arg Arg Leu Ser
145                 150                 155                 160

```
Tyr Lys Gly Tyr Phe Leu Leu Ala Lys Cys Pro Gly Asp Ser Val
            165                 170                 175

Thr Val Ser Ile Val Ser Ser Asn Ser Ala Thr Ser Cys Thr Leu Ala
                180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Lys
            210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
            245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
            275                 280                 285

Lys Gln Cys Val Ala Tyr Lys Ser Asp Gln Thr Lys Trp Val Phe Asn
290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
            325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
            355                 360                 365

Pro Glu Pro Thr Thr Glu Trp Ile Val Gly Lys Thr Val Arg Asn Phe
            370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
            405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
            435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
            485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
            515                 520                 525

Pro Phe Leu Val Val Ala Gly Ala Tyr Leu Ala Lys Val Asp Ala Tyr
            530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
            565                 570                 575
```

```
Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
        595                 600                 605

Leu Glu Cys Gln Pro Ala Ala His Ala Asp Tyr Thr Cys Lys Val Phe
        610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
        675                 680                 685

Val Tyr Val Asn Gly Val Thr Pro Gly Thr Ser Lys Asp Leu Lys Val
        690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
        770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
        850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
        915                 920                 925

His Ile Val Ser Thr Pro His Lys Asn Asp Gln Glu Phe Gln Ala Ala
        930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980
```

-continued

```
<210> SEQ ID NO 16
<211> LENGTH: 981
<212> TYPE: PRT
<213> ORGANISM: Sindbis virus

<400> SEQUENCE: 16
```

| | | | | | | | | | | | | | | | |
|---|---|---|---|---|---|---|---|---|---|---|---|---|---|---|---|
| Met | Ser | Ala | Ala | Pro | Leu | Val | Thr | Ala | Met | Cys | Leu | Leu | Gly | Asn | Val |
| 1 | | | | 5 | | | | | 10 | | | | | 15 | |
| Ser | Phe | Pro | Cys | Asp | Arg | Pro | Pro | Thr | Cys | Tyr | Thr | Arg | Glu | Pro | Ser |
| | | | 20 | | | | | 25 | | | | | 30 | | |
| Arg | Ala | Leu | Asp | Ile | Leu | Glu | Glu | Asn | Val | Asn | His | Glu | Ala | Tyr | Asp |
| | | | 35 | | | | 40 | | | | | 45 | | | |
| Thr | Leu | Leu | Asn | Ala | Ile | Leu | Arg | Cys | Gly | Ser | Ser | Gly | Arg | Ser | Lys |
| | 50 | | | | | 55 | | | | | 60 | | | | |
| Arg | Ser | Val | Ile | Asp | Asp | Phe | Thr | Leu | Thr | Ser | Pro | Tyr | Leu | Gly | Thr |
| 65 | | | | | 70 | | | | | 75 | | | | | 80 |
| Cys | Ser | Tyr | Cys | His | His | Thr | Val | Pro | Cys | Phe | Ser | Pro | Val | Lys | Ile |
| | | | | 85 | | | | | 90 | | | | | 95 | |
| Glu | Gln | Val | Trp | Asp | Glu | Ala | Asp | Asp | Asn | Thr | Ile | Arg | Ile | Gln | Thr |
| | | | 100 | | | | | 105 | | | | | 110 | | |
| Ser | Ala | Gln | Phe | Gly | Tyr | Asp | Gln | Ser | Gly | Ala | Ala | Ser | Ala | Asn | Lys |
| | | | 115 | | | | | 120 | | | | | 125 | | |
| Tyr | Arg | Tyr | Met | Ser | Leu | Glu | Gln | Asp | His | Thr | Val | Glu | Glu | Gly | Thr |
| | 130 | | | | | 135 | | | | | 140 | | | | |
| Met | Asp | Asp | Ile | Lys | Ile | Ser | Thr | Ser | Gly | Pro | Cys | Arg | Arg | Leu | Ser |
| 145 | | | | | 150 | | | | | 155 | | | | | 160 |
| Tyr | Lys | Gly | Tyr | Phe | Leu | Leu | Ala | Lys | Cys | Pro | Pro | Gly | Asp | Ser | Val |
| | | | | 165 | | | | | 170 | | | | | 175 | |
| Thr | Val | Ser | Ile | Val | Ser | Ser | Asn | Ser | Ala | Thr | Ser | Cys | Thr | Leu | Ala |
| | | | 180 | | | | | 185 | | | | | 190 | | |
| Arg | Lys | Ile | Lys | Pro | Lys | Phe | Val | Gly | Arg | Glu | Lys | Tyr | Asp | Leu | Pro |
| | | | 195 | | | | | 200 | | | | | 205 | | |
| Pro | Val | His | Gly | Lys | Lys | Ile | Pro | Cys | Thr | Val | Tyr | Asp | Arg | Leu | Lys |
| | 210 | | | | | 215 | | | | | 220 | | | | |
| Thr | Thr | Ala | Gly | Tyr | Ile | Thr | Met | His | Arg | Pro | Arg | Pro | His | Ala | Tyr |
| 225 | | | | | 230 | | | | | 235 | | | | | 240 |
| Thr | Ser | Tyr | Leu | Glu | Glu | Ser | Ser | Gly | Lys | Val | Tyr | Ala | Lys | Pro | Pro |
| | | | | 245 | | | | | 250 | | | | | 255 | |
| Ser | Gly | Lys | Asn | Ile | Thr | Tyr | Glu | Cys | Lys | Cys | Gly | Asp | Tyr | Lys | Thr |
| | | | 260 | | | | | 265 | | | | | 270 | | |
| Gly | Thr | Val | Ser | Thr | Arg | Thr | Glu | Ile | Thr | Gly | Cys | Thr | Ala | Ile | Lys |
| | | | 275 | | | | | 280 | | | | | 285 | | |
| Gln | Cys | Val | Ala | Tyr | Lys | Ser | Asp | Gln | Thr | Lys | Trp | Val | Phe | Asn | Ser |
| | 290 | | | | | 295 | | | | | 300 | | | | |
| Pro | Asp | Leu | Ile | Arg | His | Asp | Asp | His | Thr | Ala | Gln | Gly | Lys | Leu | His |
| 305 | | | | | 310 | | | | | 315 | | | | | 320 |
| Leu | Pro | Phe | Lys | Leu | Ile | Pro | Ser | Thr | Cys | Met | Val | Pro | Val | Ala | His |
| | | | | 325 | | | | | 330 | | | | | 335 | |
| Ala | Pro | Asn | Val | Ile | His | Gly | Phe | Lys | His | Ile | Ser | Leu | Gln | Leu | Asp |
| | | | 340 | | | | | 345 | | | | | 350 | | |
| Thr | Asp | His | Leu | Thr | Leu | Leu | Thr | Thr | Arg | Arg | Leu | Gly | Ala | Asn | Pro |
| | | | 355 | | | | | 360 | | | | | 365 | | |
| Glu | Pro | Thr | Thr | Glu | Trp | Ile | Val | Gly | Lys | Thr | Val | Arg | Asn | Phe | Thr |
| | 370 | | | | | 375 | | | | | 380 | | | | |

```
Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
            405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
            435                 440                 445

Ala Val Leu Cys Ala Cys Lys Ala Arg Arg Glu Cys Leu Thr Pro Tyr
450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
            485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
            515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
            565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
            595                 600                 605

Glu Cys Gln Pro Ala Ala His Ala Asp Tyr Thr Cys Lys Val Phe Gly
            610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
            645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
            675                 680                 685

Tyr Val Asn Gly Val Thr Pro Gly Thr Ser Lys Asp Leu Lys Val Ile
690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
            725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
            755                 760                 765

Lys Asn Val His Val Pro Tyr Thr Gln Ala Ser Ser Gly Phe Glu Met
            770                 775                 780

Trp Lys Asn Asn Ser Gly Arg Pro Leu Gln Glu Thr Ala Pro Phe Gly
785                 790                 795                 800
```

```
Cys Lys Ile Ala Val Asn Pro Leu Arg Ala Val Asp Cys Ser Tyr Gly
            805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
            835                 840                 845

Thr Tyr Ser Ala Asp Phe Gly Gly Met Ala Thr Leu Gln Tyr Val Ser
            850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
            885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
            915                 920                 925

Ile Val Ser Thr Pro His Lys Asn Asp Gln Glu Phe Gln Ala Ala Ile
            930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
            965                 970                 975

Thr Ser Thr Arg Arg
            980

<210> SEQ ID NO 17
<211> LENGTH: 982
<212> TYPE: PRT
<213> ORGANISM: Sindbis virus

<400> SEQUENCE: 17

Met Ser Ala Ala Pro Leu Val

```
Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Lys
210                 215                 220

Glu Thr Thr Ala Gly Tyr Ile Thr Met His Arg Pro Arg Pro His Ala
225                 230                 235                 240

Tyr Thr Ser Tyr Leu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
            275                 280                 285

Lys Gln Cys Val Ala Tyr Lys Ser Asp Gln Thr Lys Trp Val Phe Asn
            290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
            355                 360                 365

Pro Glu Pro Thr Thr Glu Trp Ile Val Gly Lys Thr Val Arg Asn Phe
            370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
            435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
            515                 520                 525

Pro Phe Leu Val Val Ala Gly Ala Tyr Leu Ala Lys Val Asp Ala Tyr
            530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590
```

-continued

```
Lys Phe Thr Thr Val Val Pro Ser Pro Lys Ile Lys Cys Cys Gly Ser
            595                 600                 605

Leu Glu Cys Gln Pro Ala Ala His Ala Asp Tyr Thr Cys Lys Val Phe
        610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
        675                 680                 685

Val Tyr Val Asn Gly Val Thr Pro Gly Thr Ser Lys Asp Leu Lys Val
    690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
    770                 775                 780

Met Trp Lys Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
        915                 920                 925

His Ile Val Ser Thr Pro His Lys Asn Asp Gln Glu Phe Gln Ala Ala
    930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980
```

<210> SEQ ID NO 18
<211> LENGTH: 423
<212> TYPE: PRT

<213> ORGANISM: Sindbis virus

<400> SEQUENCE: 18

```
Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Lys Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
        115                 120                 125

Lys Ile Lys Pro Lys Phe Val Gly Arg Glu Lys Tyr Asp Leu Pro Pro
    130                 135                 140

Val His Gly Lys Lys Ile Pro Cys Thr Val Tyr Asp Arg Leu Lys Glu
145                 150                 155                 160

Thr Thr Ala Gly Tyr Ile Thr Met His Arg Pro Arg Pro His Ala Tyr
                165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
    210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
            260                 265                 270

Ala Pro Asn Val Ile His Gly Phe Lys His Ile Ser Leu Gln Leu Asp
        275                 280                 285

Thr Asp His Leu Thr Leu Leu Thr Thr Arg Arg Leu Gly Ala Asn Pro
    290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
            340                 345                 350

His Glu Ile Val Gln His Tyr Tyr His Arg His Pro Val Tyr Thr Ile
        355                 360                 365

Leu Ala Val Ala Ser Ala Thr Val Ala Met Met Ile Gly Val Thr Val
    370                 375                 380

Ala Val Leu Cys Ala Cys Lys Ala Arg Arg Glu Cys Leu Thr Pro Tyr
385                 390                 395                 400

```
Ala Leu Ala Pro Asn Ala Val Ile Pro Thr Ser Leu Ala Leu Leu Cys
                405                 410                 415
Cys Val Arg Ser Ala Asn Ala
            420

<210> SEQ ID NO 19
<211> LENGTH: 65
<212> TYPE: PRT
<213> ORGANISM: Sindbis virus

<400> SEQUENCE: 19

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg
65

<210> SEQ ID NO 20
<211> LENGTH: 488
<212> TYPE: PRT
<213> ORGANISM: Sindbis virus

<400> SEQUENCE: 20

Met Ser Ala Ala Pro Leu Val Thr Ala Met Cys Leu Leu Gly Asn Val
1               5                   10                  15

Ser Phe Pro Cys Asp Arg Pro Pro Thr

-continued

```
Glu Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
            245                 250                 255

Pro Ser Gly Lys Asn Ile Thr Tyr Glu Cys Lys Cys Gly Asp Tyr Lys
        260                 265                 270

Thr Gly Thr Val Ser Thr Arg Thr Glu Ile Thr Gly Cys Thr Ala Ile
    275                 280                 285

Lys Gln Cys Val Ala Tyr Lys Ser Asp Gln Thr Lys Trp Val Phe Asn
290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala
                485
```

<210> SEQ ID NO 21
<211> LENGTH: 683
<212> TYPE: DNA
<213> ORGANISM: Human immunodeficiency virus type 1

<400> SEQUENCE: 21

```
cctagaaaaa catggagcaa tcacaagtag caatacagca gctaccaatg ctgattgtgc      60
ctggctagaa gcacaagagg aggaggaggt gggttttcca gtcacacctc aggtaccttt     120
aagaccaatg acttacaagg cagctgtaga tcttagccac ttttaaaag aaaaggggg      180
actggaaggg ctaattcact cccaacgaag acaagatatc cttgatctgt ggatctacca     240
cacacaaggc tacttccctg attggcagaa ctacacacca gggccaggga tcagatatcc     300
actgaccttt ggatggtgct acaagctagt accagttgag caagagaagg tagaagaagc     360
caatgaagga gagaacaccc gcttgttaca ccctgtgagc ctgcatggga tggatgaccc     420
ggagagagaa gtattagagt ggaggtttga cagccgccta gcatttcatc acatggcccg     480
agagctgcat ccggactgta ctgggtctct ctggttagac cagatctgag cctgggagct     540
ctctggctaa ctagggaacc cactgcttaa gcctcaataa agcttgcctt gagtgcttca     600
```

```
agtagtgtgt gcccgtctgt tgtgtgactc tggtaactag agatccctca gacccttta      660 gtcagtgtgg aaaatctcta gca                                             683
```

<210> SEQ ID NO 22
<211> LENGTH: 416
<212> TYPE: DNA
<213> ORGANISM: Human immunodeficiency virus type 1

<400> SEQUENCE: 22

```
cctagaaaaa catggagcaa tcacaagtag caatacagca gctaccaatg ctgattgtgc      60
ctggctagaa gcacaagagg aggaggaggt gggttttcca gtcacacctc aggtaccttt     120
aagaccaatg acttacaagg cagctgtaga tcttagccac ttttaaaag aaaaggggg       180
actggaaggg ctaattcact cccaacgaag acaagatctg cttttgcct gtactgggtc      240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagca         416
```

<210> SEQ ID NO 23
<211> LENGTH: 401
<212> TYPE: DNA
<213> ORGANISM: Human immunodeficiency virus type 1

<400> SEQUENCE: 23

```
cctagaaaaa catggagcaa tcacaagtag caatacagca gctaccaatg ctgattgtgc      60
ctggctagaa gcacaagagg aggaggaggt gggttttcca gtcacacctc aggtaccttt     120
aagaccaatg acttacaagg cagctgtaga tcttagccac tttttactgg aagggctaat    180
tcactcccaa cgaagacaag atctgctttt tgcctgtact gggtctctct ggttagacca    240
gatctgagcc tgggagctct ctggctaact agggaaccca ctgcttaagc ctcaataaag    300
cttgccttga gtgcttcaag tagtgtgtgc ccgtctgttg tgtgactctg gtaactagag    360
atccctcaga cccttttagt cagtgtggaa aatctctagc a                        401
```

<210> SEQ ID NO 24
<211> LENGTH: 8
<212> TYPE: PRT
<213> ORGANISM: Gallus gallus

<400> SEQUENCE: 24

Ser Ile Ile Asn Phe Glu Lys Leu
1               5

<210> SEQ ID NO 25
<211> LENGTH: 9
<212> TYPE: PRT
<213> ORGANISM: Mus musculus

<400> SEQUENCE: 25

Ser Pro Ser Tyr Ala Tyr His Gln Phe
1               5

<210> SEQ ID NO 26
<211> LENGTH: 5
<212> TYPE: PRT
<213> ORGANISM: Sindbis virus

```
<400> SEQUENCE: 26

Arg Ser Lys Arg Ser
1               5

<210> SEQ ID NO 27
<211> LENGTH: 4
<212> TYPE: PRT
<213> ORGANISM: Sindbis virus

<400> SEQUENCE: 27

Arg Ser Lys Arg
1

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide

<400> SEQUENCE: 28

Asp Tyr Lys Asp Asp Asp Asp Lys
1               5
```

COMPOSITIONS COMPRISING LENTIVIRAL VECTORS EXPRESSING IL-12 AND METHODS OF USE THEREOF

CROSS-REFERENCE TO RELATED APPLICATIONS

This application is a national phase of International Application No. PCT/US16/60968, which claims the benefit of U.S. Provisional Application No. 62/261,655 filed on Dec. 1, 2015, and U.S. Provisional Application No. 62/252,877 filed on Nov. 9, 2015. The entire contents of these applications are incorporated herein by reference in their entirety.

TECHNICAL FIELD

This patent application relates generally to the treatment of cancer, and more particularly to the use of a pseudotyped lentivirus expressing IL-12 for the treatment of cancer.

BACKGROUND

Cancer cells express antigens. Despite the presence of such antigens, tumors are generally not readily recognized and eliminated by the host, as evidenced by the development of disease. The inability of the immune system to protect against tumors may be due to mechanisms of evasion, active suppression, or sub-optimal activation of the response.

Cytokines are integral to both the innate and acquired immune systems. They can alter the balance of cellular and humoral responses, alter class switching of B lymphocytes and modify innate responses.

Interleukin-12 is a heterodimeric cytokine with multiple biological effects on the immune system. It is composed of two subunits, p35 and p40, both of which are required for the secretion of the active form of IL-12, p70. Interleukin-12 acts on dendritic cells (DC), leading to increased maturation and antigen presentation, which can allow for the initiation of a T cell response to tumor specific antigens. It also drives the secretion of IL-12 by DCs, creating a positive feedback mechanism to amplify the response. Once a response is initiated, IL-12 plays a fundamental role in directing the immune system towards a Th1 cytokine profile, inducing CD4+ T cells to secrete interferon-gamma (IFN-.gamma.) and leading to a CD8+ cytotoxic T cell response (see e.g., Cancer Immunol Immunother (2014) 63:419-435). However, IL-12 is also a strong pro-inflammatory cytokine that leads to the secretion of other cytokines including tumor necrosis factor-alpha (TNF-.alpha.) which, combined with IFN-.gamma., is a prerequisite for the development of CD4+ cytotoxic T lymphocytes (CTL) (Sasiain, M. C., et al. (1998) Clinical and experimental immunology 114: 196-203). Furthermore, IL-12 can promote the activation of innate immune cells such as macrophages and eosinophils through its induction of IFNγ and other cytokines. This activation then leads to IL-12 secretion by these cells and further amplification of both the innate and acquired responses (Portielje, J. E., et al., (2003) Cancer Immunol Immunother 52: 133-144.). However, high levels of IL-12, and consequently IFNγ, have also been associated with induction of antagonistic molecules such as IL-10 and the depletion of signalling molecules downstream of IL-12, such as STAT4 (Portielje, J. E., et al. (2003) Clin Cancer Res 9: 76-83; Sacco, S., et al. (1997) Blood 90: 4473-4479; Leonard, J. P., et al. (1997) Blood 90: 2541-2548.).

Direct injection of recombinant IL-12 has been shown in some mouse models of leukemia (Masztalerz, A., et al., (2003) Cancer Immunol Immunother 52: 235-242; Zagozdzon, R., et al. (1998) Int J Cancer 77: 720-727; Tatsumi, T., et al. (2001) Cancer research 61: 7563-7567; Nastala, C. L., et al. (1994) J Immunol 153: 1697-1706; Dunussi-Joannopoulos, K., et al., (1999) Blood 94: 4263-4273.). While initial human trials employing this approach were less promising (Atkins, M. B., et al. (1997) Clin Cancer Res 3: 409-417; Kang, W. K., et al. (2001) Human gene therapy 12: 671-684; Mazzolini, G., et al. (2005) J Clin Oncol 23: 999-1010; Dohnal, A. M., et al., (2007) Cytotherapy 9: 755-770.). Innovative gene therapy strategies may accelerate the development of prophylactic immunotherapy against cancer.

SUMMARY OF THE INVENTION

One aspect of the present invention provides a lentiviral vector particle comprising: a) an envelope comprising a Sindbis virus E2 glycoprotein of SEQ ID NO: 1 in which 160X is absent or is an amino acid other than glutamic acid, or a variant of SEQ ID NO: 1 thereof having at least 80% identity to SEQ ID NO: 1 and in which 160X is absent or is an amino acid other than glutamic acid, capable of infecting dendritic cells; wherein E2 is not part of a fusion protein with Sindbis virus E3; and b) a lentiviral vector genome comprising a sequence encoding IL-12. In certain embodiments of the lentiviral vector particles described herein, the IL-12 is a single chain IL-12 (scIL-12). In certain embodiments of the lentiviral vectors described herein, scIL-12 comprises p35-L-p40. In certain embodiments of the lentiviral vector particles described herein, the scIL-12 comprises p40-L-p35. In other embodiments of the lentiviral vector particles described herein, the lentiviral vector genome further comprises a sequence encoding an antigen. In this regard, the antigen is a tumor associated antigen, a viral antigen, a bacterial antigen or a fungal antigen. In certain embodiments, the tumor associated antigen is selected from the group consisting of prostatic acid phosphatase, prostate specific antigen, NKX3.1, prostate specific membrane antigen, PRAME; BAGE; RAGE, NY-ESO-1, SAGE, HAGE, GAGE, Plu-1, HASH-1, HasH-2, Cripto, Criptin, MART-1/Melan-A, gp100, gp75, mda-7, tyrosinase, tyrosinase-related protein, p53, Ras, c-Myc, A-Raf, B-Raf, and C-Raf, MAGE-A1, MAGE-A2, MAGE-A3, MAGE-A4, MAGE-A6, MAGE-A10, MAGE-A12, MART-1, BAGE, DAM-6, -10, GAGE-1, GAGE-2, GAGE-8, GAGE-3, GAGE-4, GAGE-5, GAGE-6, GAGE-7B, NA88-A, MART-1, MC1R, Gp100, PSM, TRP-1, TRP-2, ART-4, CAMEL, CEA, Cyp-B, hTERT, hTRT, iCE, MUC1, MUC2, PRAME, P15, RU1, RU2, SART-1, SART-3, Wilms' tumor antigen (WT1), AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, Epidermal Growth Factor receptor (EGFR and EGFRvIII), platelet derived growth factor receptor (PDGFR), vascular endothelial growth factor receptor (VEGFR), integrin-linked kinase (ILK), STAT3, STAT5, STAT6, HIF-1, HIF-2, Nuclear Factor-Kappa B (NF-κB), Notch1-4, c-Met, mammalian targets of rapamycin (mTOR), WNT, PMSA, PR-3, MDM2, Mesothelin, renal cell carcinoma—5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGs5, SART3, STn, PAX5, OY-TES1, sperm protein 17, LCK, HMWMAA, AKAP-4, SSX2, XAGE 1, B7H3, legumain, TIE2, Page4, MAD-CT-1, FAP, MAD-CT-2, and fos related antigen 1.

Another aspect of the present invention provides a method of treating cancer in a subject, comprising administering to the subject an effective amount of a composition comprising a lentiviral vector described herein, such as the lentiviral vector particle comprising: a) an envelope comprising a Sindbis virus E2 glycoprotein of SEQ ID NO: 1 in which 160X is absent or is an amino acid other than glutamic acid, or a variant of SEQ ID NO: 1 thereof having at least 80% identity to SEQ ID NO: 1 and in which 160X is absent or is an amino acid other than glutamic acid, capable of infecting dendritic cells; wherein E2 is not part of a fusion protein with Sindbis virus E3; and b) a lentiviral vector genome comprising a sequence encoding IL-12. In certain embodiments, the methods further comprise administering to the subject an effective amount of a composition comprising a second lentiviral vector encoding a tumor antigen. In certain embodiments, the lentiviral vector particle expressing IL-12 and the $2^{nd}$ lentiviral vector are administered concurrently. In another embodiment, the lentiviral vector particle expressing IL-12 and the second lentiviral vector are administered sequentially at different times. In other embodiments, the lentiviral vector particle expressing IL-12 as described herein and the second lentiviral vector are administered by different routes. In another embodiment, the lentiviral vector particle expressing IL-12 as described herein and the $2^{nd}$ lentiviral vector are administered at different sites. In other embodiments, the lentiviral vector particle expressing IL-12 as described herein and the $2^{nd}$ lentiviral vector are administered at different sites, by the same route. In another embodiment, the lentiviral vector particles as described herein expressing IL-12 is administered intratumorally. In one embodiment, a TLR4 agonist is administered intratumorally in conjunction with the lentiviral vector particles described herein. In certain embodiments the TLR4 agonist is administered intratumorally in the same composition as the lentiviral vector particles expressing IL-12. In other embodiments, the TLR4 agonist is administered intratumorally at the same time as the lentiviral vector particles expressing IL-12 but is administered in a separate composition. In those embodiments where a TLR4 agonist is administered, the TLR4 agonist may be glucopyranosyl lipid A either in an aqueous or an oil in water emulsion formulation. In certain embodiments the lentiviral vector particles described herein expressing IL-12 is administered intratumorally and the second lentiviral vector is administered concurrently at a different site and by a different route.

Another aspect of the present invention provides a method of treating cancer in a subject, comprising administering to the subject an effective amount of a composition comprising a lentiviral vector particle as described herein expressing IL-12 and wherein the lentiviral vector genome further comprises a sequence encoding an antigen. In certain embodiments, the lentiviral vector particle is administered intratumorally. In particular embodiments, the lentiviral vector particle is administered in a single dose. In another embodiment, the lentiviral vector particle produces a low-level of IL-12. In this regard, the low-level of IL-12 is between about 0.1 µg and 1 µg/1E10 vector genomes produced during the first 48 hours as measured in an in vitro transduction assay.

Other aspects of the present invention include a lentiviral vector particle expressing IL-12 as described herein for use in a method of treatment of a human or animal subject.

Another aspect of the invention provides a composition comprising: a) an envelope comprising a Sindbis virus E2 glycoprotein of SEQ ID NO: 1 in which 160X is absent or is an amino acid other than glutamic acid, or a variant of SEQ ID NO: 1 thereof having at least 80% identity to SEQ ID NO: 1 and in which 160X is absent or is an amino acid other than glutamic acid, capable of infecting dendritic cells; wherein E2 is not part of a fusion protein with Sindbis virus E3; and b) a lentiviral vector genome comprising a sequence encoding IL-12; in combination with a second lentiviral vector particle encoding a tumor antigen.

Another aspect of the invention provides a product comprising: a) a first composition comprising a lentiviral vector particular wherein the particle comprises: 1) an envelope comprising a Sindbis virus E2 glycoprotein of SEQ ID NO: 1 in which 160X is absent or is an amino acid other than glutamic acid, or a variant of SEQ ID NO: 1 thereof having at least 80% identity to SEQ ID NO: 1 and in which 160X is absent or is an amino acid other than glutamic acid, capable of infecting dendritic cells; wherein E2 is not part of a fusion protein with Sindbis virus E3; and 2) a lentiviral vector genome comprising a sequence encoding IL-12; and b) a second composition comprising a second lentiviral vector particle encoding a tumor antigen; for use in a method of treating cancer in a subject by intratumoral administration of the first composition and administration of the second composition by a different route. In one embodiment, the second composition is administered intradermally, subcutaneously or intramuscularly. In another embodiment, the first composition and the second composition are administered concurrently. In a further embodiment, the first composition and the second composition are administered sequentially.

Another aspect of the invention provides a therapeutic or prophylactic vaccine comprising a pharmaceutically acceptable excipient and a lentiviral vector particle comprising: a) an envelope comprising a Sindbis virus E2 glycoprotein of SEQ ID NO: 1 in which 160X is absent or is an amino acid other than glutamic acid, or a variant of SEQ ID NO: 1 thereof having at least 80% identity to SEQ ID NO: 1 and in which 160X is absent or is an amino acid other than glutamic acid, capable of infecting dendritic cells; wherein E2 is not part of a fusion protein with Sindbis virus E3; and b) a lentiviral vector genome comprising a sequence encoding IL-12; and wherein the lentiviral vector genome further comprises a sequence encoding an antigen.

Another aspect of the invention provides a method of treating cancer in a subject, comprising administering to the subject an effective amount of a composition comprising a lentiviral vector particle comprising a lentiviral vector genome comprising a sequence encoding IL-12; wherein the composition comprising the lentiviral vector particle is administered intratumorally; and wherein the lentiviral vector particle produces a low-level of IL-12 of between about 0.1 µg and 1 µg/1E10 vector genomes during the first 48 hours as measured in an in vitro transduction assay. In certain embodiments, the treatment further comprises regulatory T cell depletion. In this regard, the regulatory T cell depletion may comprise systemic administration of cyclophosphamide or treatment with an agent such as an antibody, that depletes regulatory T cells. An exemplary such antibody is an anti-CD25 antibody. In certain embodiments, the systemic administration of cyclophosphamide or an anti-CD25 antibody is prior to the intratumoral injection of the composition comprising the lentiviral vector.

Any of the methods of treatment of cancer described herein may be combined with regulatory T cell depletion such as systemic administration of cyclophosphamide or an agent, such as an antibody, that depletes regulatory T cells (e.g., anti-CD25 antibodies).

Still another aspect of the present invention provides a lentiviral vector particle comprising: a) an envelope comprising a Sindbis virus E2 glycoprotein of SEQ ID NO: 1 in which 160X is absent or is an amino acid other than glutamic acid, or a variant of SEQ ID NO: 1 thereof having at least 80% identity to SEQ ID NO: 1 and in which 160X is absent or is an amino acid other than glutamic acid, capable of infecting dendritic cells; wherein E2 is not part of a fusion protein with Sindbis virus E3; and b) a lentiviral vector genome comprising a sequence encoding IL-23.

BRIEF DESCRIPTION OF THE DRAWINGS

FIG. 9A shows tumor growth curves and FIG. 9B shows survival curves of both an integrating (LV703) and integration deficient (LV704, also referred to as VP02) lentiviral vector.

FIG. 10A shows tumor growth curves and FIG. 10B shows survival curves of both an integrating (LV703) and integration deficient (LV704, also referred to as VP02) lentiviral vector.

FIG. 11A shows tumor growth curves and FIG. 11B shows survival curves of both an integrating (LV703) and integration deficient (LV704, also referred to as VP02) lentiviral vector.

FIG. 12A shows tumor growth curves and FIG. 12B shows survival curves of both an integrating (LV703) and integration deficient (LV704, also referred to as VP02) lentiviral vector.

FIG. 13A shows tumor growth curves and FIG. 13B shows survival curves of both an integrating (LV703) and integration deficient (LV704, also referred to as VP02) lentiviral vector.

FIG. 14A shows tumor growth curves and FIG. 14B shows survival curves of both an integrating (LV703) and integration deficient (LV704, also referred to as VP02) lentiviral vector.

FIG. 15A shows the percent cytokine positive CD4 T cells and FIG. 15B shows the percent total IFNγ CD4 positive T cells.

FIG.

Figure 21:
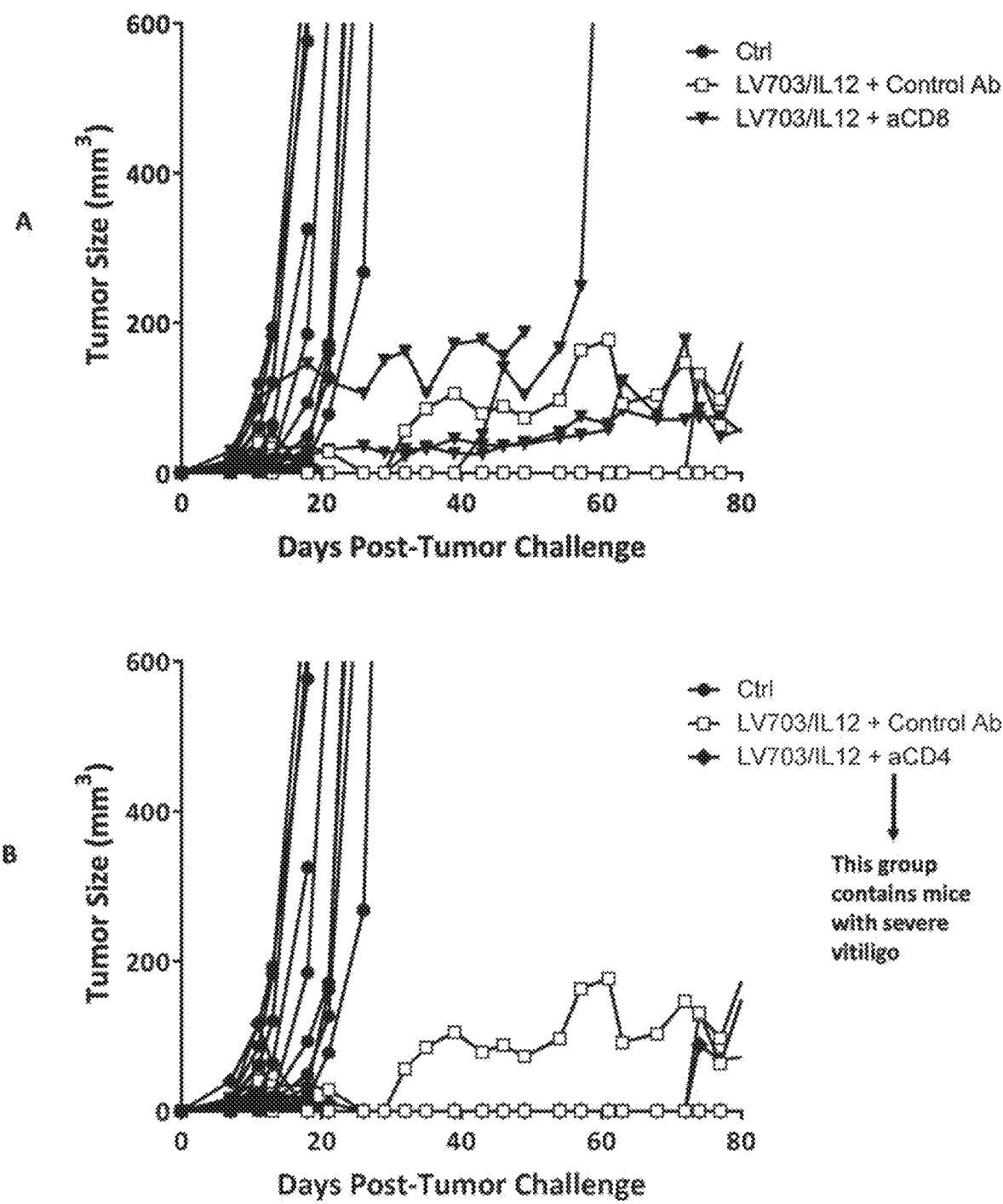
Figure 21:
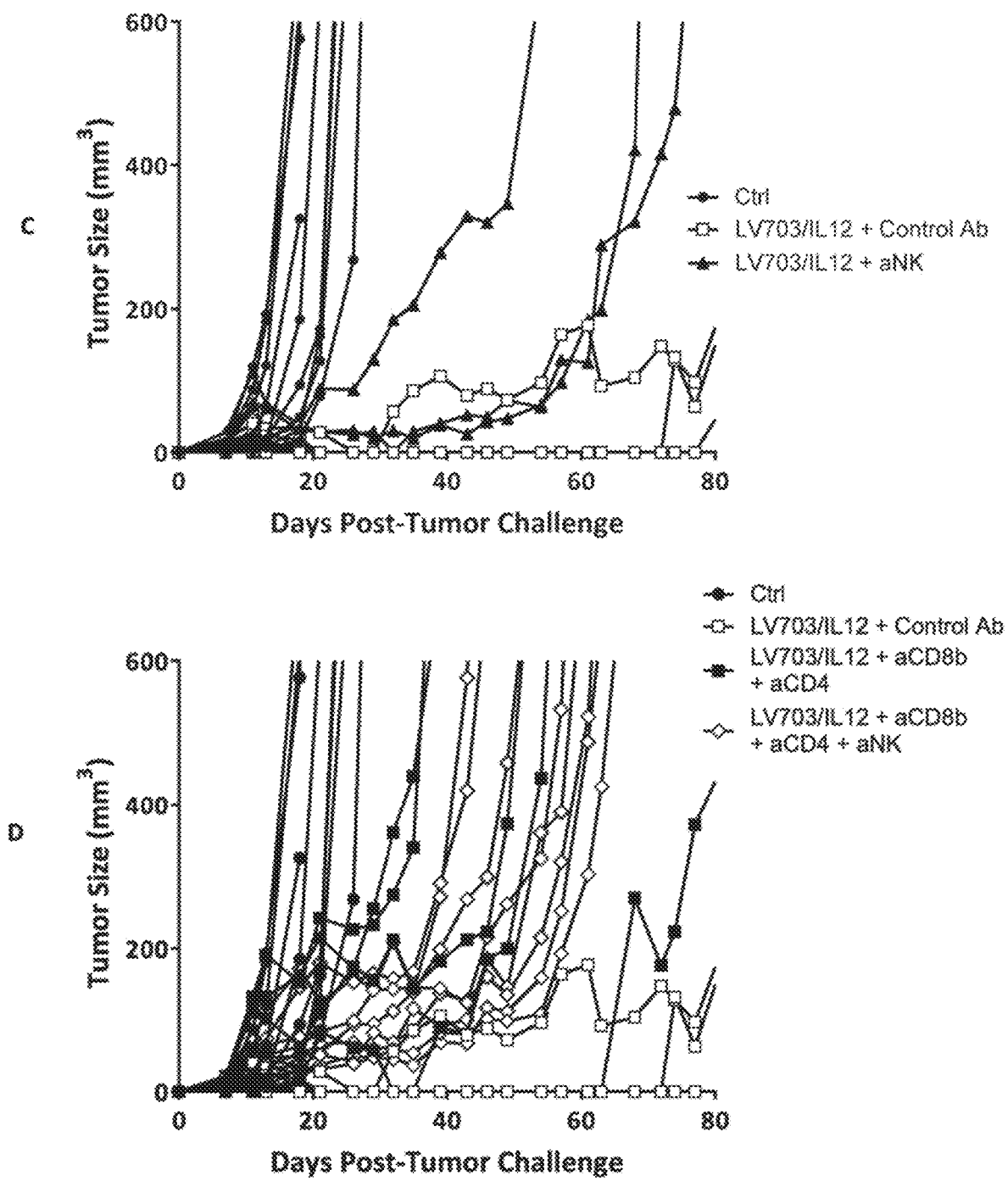
Figure 21:
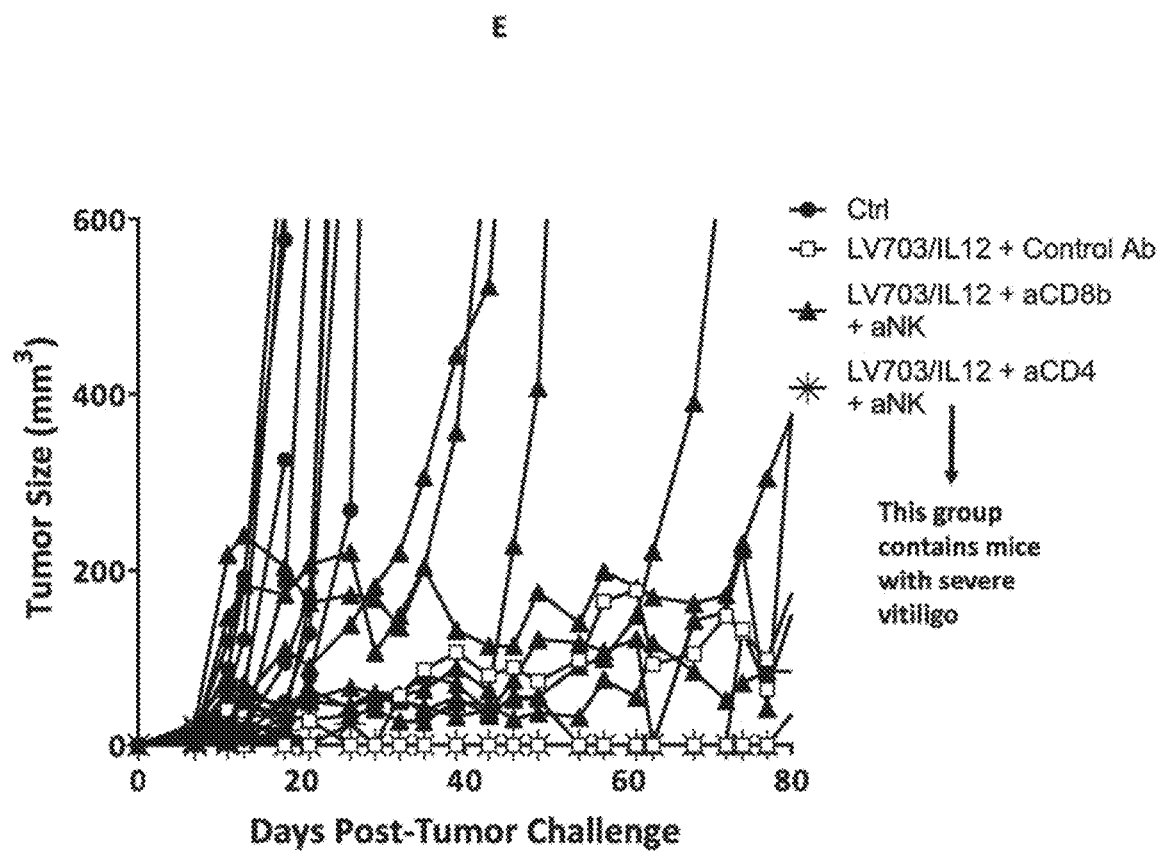

FIG. 21 graphs the individual tumor size (B16F10 flank model) in mice treated i.t. with LV703/IL-12 and depletion of different cell types: (21A): CD8 T cell depletion; (21B): CD4 T cell depletion; (21C): NK cell depletion; (21D): CD8+ CD4 depletion and CD8, CD4+NK depletion; (21E): CD8+NK and CD4+NK depletion.

DETAILED DESCRIPTION

The present disclosure provides methods and compositions for treating cancer by administering lentiviral vectors encoding IL-12. In certain embodiments, the lentiviral vectors are dendritic cell (DC) targeted lentiviral vectors expressing IL-12. In particular embodiments, the lentiviral vector particles comprise an envelope glycoprotein variant derived from Sindbis virus E2, and a genome that comprises the sequence encoding IL-12, and optionally other components. The glycoprotein variant exhibits reduced binding to heparan sulfate compared to HR, a reference Sindbis virus strain. The envelope glycoprotein facilitates infection of dendritic cells by the lentiviral vector particles. "Facilitates" infection, as used herein, is the same as facilitates transduction and refers to the role of the envelope glycoprotein, acting alone or in concert with other molecules, in promoting or enhancing receptor-mediated entry of a pseudotyped retrovirus or lentivirus particle into a target cell.

In general, the lentiviral vector particles are produced by a cell line that contains one or more plasmid vectors and/or integrated elements that together encode the components necessary to generate functional vector particles. These lentiviral vector particles are typically not replication-competent, i.e., they are only capable of a single round of infection. Most often, multiple plasmid vectors or individual expression cassettes integrated stably into the producer cell chromosome are utilized to separate the various genetic components that generate the lentiviral vector particles, however, a single plasmid vector having all of the lentiviral components can be used. In one exemplification, the packaging cell line is transfected with one or more plasmids containing the viral vector genome, including LTRs, a cis-acting packaging sequence, and the sequence(s) of interest, at least one plasmid encoding the virus enzymatic and structural components (e.g., gag and pol), and at least one plasmid encoding an envelope glycoprotein. In certain embodiments, the envelope protein is an Arbovirus envelope glycoprotein. In other embodiments, the envelope protein is derived from a virus heterologous to the virus used for the genome (e.g. the envelope glycoprotein is derived from a virus other than a lentiviral vector). Viral particles bud through the cell membrane and comprise a core that includes typically two RNA genomes paid containing the sequence of interest and an envelope glycoprotein, such as an Arbovirus envelope that targets dendritic cells. When the Arbovirus glycoprotein is a Sindbis virus E2 glycoprotein, the glycoprotein is engineered to have reduced binding to heparan sulfate compared to the reference strain HR. This usually involves at least one amino acid change compared to the HR E2 glycoprotein sequence.

Without wishing to be bound by theory, it is believed that the binding of the viral particle to a cell surface induces endocytosis, bringing the virus into an endosome, triggering membrane fusion, and allowing the virus core to enter the cytosol. For certain embodiments, which utilize integrating lentiviral vector particles, following reverse transcription and migration of the product to the nucleus, the genome of the virus integrates into the target cell genome, incorporating the sequence(s) of interest into the genome of the target cell. To reduce the chance of insertional mutagenesis and to promote transient expression of a designate antigen(s), however, other embodiments utilize integration deficient lentiviral vector particles, which do not integrate into the target cell genome, but instead express the sequence(s) of interest from an episome. Either way, the infected cell then expresses the sequence(s) of interest, e.g., IL-12 and optionally an antigen and/or a stimulatory molecule. When included, the antigen can then be processed by dendritic cells and presented to T and B cells, generating an antigen-specific immune response. The specific pathway described above is not required so long as the dendritic cell is able to stimulate an antigen-specific immune response.

The viral particles can be administered to a subject in order to provide a prophylactic or therapeutic effect. The product of the sequence of interest is typically single chain IL-12 (scIL-12) or other form of IL-12 and can also include an antigen of a disease-causing agent or a diseased cell (e.g., tumor cell), and or additional immunomodulatory molecules, such as cytokines. Following infection of dendritic cells and expression of the product, IL-12 is expressed and, in those embodiments where antigen is expressed from the vector in addition to IL-12, an immune response is generated to the antigen and boosted by the expressed IL-12 product. The immune response may be humoral or cellular or both.

A. Viral Vector Envelope

The viral vectors described herein are generally pseudotyped with an envelope protein from a heterologous virus. In certain embodiments, the viral vectors are pseudotyped with VSVg envelope glycoprotein. In other embodiments, the viral vectors may be pseudotyped with an envelope glycoprotein derived from a heterologous HIV (e.g., HIV-2) or other heterologous retrovirus such as feline immunodeficiency virus (FIV), equine infectious anemia virus, Simian Immunodeficiency Virus (SIV) or maedi/visna virus.

In particular embodiments, the viral vectors described herein are pseudotyped with an envelope glycoprotein derived from an Arbovirus. Arthropod-borne viruses (Arboviruses) are viruses that are transmitted to a host, such as humans, horses, or birds by an infected arthropod vector such as a mosquito. Arboviruses are further divided into sub-families of viruses including alphaviruses and flaviviruses, which have a single-stranded RNA genome of positive polarity and a glycoprotein-containing envelope. For example, dengue fever virus, yellow fever virus and West Nile virus belong to the flavivirus family, and Sindbis virus, Semliki Forest virus and Venezuelan Equine Encephalitis virus, are members of the alphavirus family (Wang et al. J. Virol. 66, 4992 (1992)). The envelope of Sindbis virus includes two transmembrane glycoproteins (Mukhopadhyay et al. Nature Rev. Microbio. 3, 13 (2005)): E1, believed to be responsible for fusion, and E2, believed to be responsible for cell binding. Sindbis virus envelope glycoproteins are known to pseudotype other retroviruses, including oncoretroviruses and lentiviruses.

As discussed above, an arbovirus envelope glycoprotein can be used to pseudotype a lentiviral-based vector genome. A "pseudotyped" lentivirus is a lentiviral particle having one or more envelope glycoproteins that are encoded by a virus that is distinct from the lentiviral genome. The envelope glycoprotein may be modified, mutated or engineered as described herein.

The envelope of Sindbis virus and other alphaviruses incorporates into the lipid bilayer of the viral particle membrane, and typically includes multiple copies of two glycoproteins, E1 and E2. Each glycoprotein has membrane-spanning regions; E2 has an about 33 residue cytoplasmic domain whereas the cytoplasmic tail of E1 is very short (about 2 residues). Both E1 and E2 have palmitic acids attached in or near the membrane-spanning regions. E2 is initially synthesized as a precursor protein that is cleaved by furin or other Ca2+-dependent serine proteinase into E2 and a small glycoprotein called E3. Located between sequences encoding E2 and E1 is a sequence encoding a protein called 6K. E3 and 6K are signal sequences which serve to translocate the E2 and E1 glycoproteins, respectively, into the membrane. In the Sindbis virus genome, the coding region for Sindbis envelope proteins includes sequence encoding E3, E2, 6K, and E1. As used herein, "envelope" of an arbovirus virus includes at least E2, and may also include E1, 6K and E3. An exemplary sequence of envelope glycoproteins of Sindbis virus, strain HR, is presented as SEQ ID No. 17 of WO 2011/011584. Sequences of envelope glycoproteins for other arboviruses can be found in e.g., GenBank. For example, sequence encoding Dengue virus glycoproteins can be found in Accession GQ252677 (among others in GenBank) and in the virus variation database at NCBI (GenBank accessions and virus variation database are incorporated by reference for envelope glycoprotein sequences) and sequence encoding Venezuelan equine encephalitis virus envelope glycoproteins in Accession NP 040824 (incorporated by reference for sequences of envelope glycoproteins).

Although the cellular receptor(s) on dendritic cells for alphaviruses, and Sindbis virus in particular, have not been definitively identified to date, one receptor appears to be DC-SIGN (Klimstra et al., J Virol 77: 12022, 2003). The use of the terms "attachment", "binding", "targeting" and the like are used interchangeably and are not meant to indicate a mechanism of the interaction between Sindbis virus envelope glycoprotein and a cellular component. DC-SIGN (Dendritic Cell Specific ICAM-3 (Intracellular Adhesion Molecules 3)-Grabbing Nonintegrin; also known as CD209) is a C-type lectin-like receptor capable of rapid binding and endocytosis of materials (Geijtenbeek, T. B., et al. Annu. Rev. Immunol. 22: 33-54, 2004). E2 appears to target virus to dendritic cells through DC-SIGN. As shown herein, cells expressing DC-SIGN are transduced by viral vector particles pseudotyped with Sindbis virus E2 better (at least 2-fold, at least 3-fold, at least 4-fold, at least 5-fold, at least 6-fold, at least 7-fold, at least 8-fold, at least 9-fold, or at least 10-fold better) than isogenic cells that don't express DC-SIGN. The mechanism of how E2 glycoprotein facilitates viral infection appears to involve DC-SIGN, possibly through direct binding to DC-SIGN or causing a change in conformation or some other mechanism. Regardless of the actual mechanism, the targeting by E2 is preferential for cells expressing DC-SIGN, namely dendritic cells.

Sindbis virus also appears to bind to cells via heparan sulfate (Klimstra et al., J Virol 72: 7357, 1998; Burmes and Griffin, J Virol 72: 7349, 1998). Because heparan sulfate and other cell surface glycosaminoglycans are found on the surface of most cell types, it is desirable to reduce interaction between heparan sulfate and Sindbis envelope glycoproteins. This can be accomplished by diminishing the binding of Sindbis virus envelope to heparan sulfate or increasing the binding, e.g., increasing avidity, of Sindbis virus envelope to dendritic cells or both. As a result, non-specific binding to other molecules, which may be expressed by other cell types and which may occur even if the envelope is specific for DC-SIGN, is reduced, and the improved specificity may serve to avoid undesired side effects, such as side effects that may reduce the desired immune response, or side effects associated with off-target transduction of other cell types. Alternatively or in addition to the advantages of relatively specific transduction of cells expressing DC-SIGN, viral particles pseudo-typed with Sindbis virus envelope E2 glycoprotein may offer other advantages over viral particles pseudo-typed with glycoproteins such as VSVG. Examples of such advantages include reduced complement-mediated lysis and/or reduced neuronal cell targeting, both of which are believed to associate with administration of VSV-G pseudo-typed viral particles.

In various exemplifications, the lentiviral vector particles specifically bind to cells expressing DC-SIGN and have reduced or abrogated binding to heparan sulfate. That is, a Sindbis virus envelope E2 glycoprotein may be modified to preferentially direct the virus to dendritic cells that express DC-SIGN relative to other cell types. Based on information obtained from structural studies and molecular modeling among other studies, variant sequences of envelope proteins, especially E2 and E1 glycoproteins, are designed and generated such that the glycoproteins maintain their functions as envelope proteins, but have the desired binding specificity, avidity, or level of binding. Candidate variant sequences may be created for each glycoprotein and assayed using the methods described below, or other methods known in the art, to identify envelope glycoproteins with the most desirable characteristics.

Certain variant sequences of Sindbis E2 have at least one amino acid alteration at residue 160 as compared to SEQ ID NO: 1. Residue 160 is deleted or changed to an amino acid other than glutamic acid. An alteration is most commonly a substitution of at least one amino acid, but alternatively can be an addition or deletion of one or more amino acids. Preferably, any additional amino acids are few in number and do not comprise an antigenic epitope (e.g., hemagglutinin tag sequence), which may compromise safety. When there are two or more alterations, they can both be of the same type (e.g., substitution) or differing types (e.g., a substitution and a deletion). Multiple alterations can be scattered or located contiguously in the protein sequence. Illustrative variants of E2 glycoproteins for use in the present invention are described in WO2011011584 and include any of SEQ ID NOs: 3-15 of the sequence listing provided herein and the variants thereof described herein.

In the first instance, variant sequences comprise at least one amino acid alteration in the region of about residue 50 to about residue 180. Within this region are amino acids that are involved with binding to heparan sulfate. By reducing the net positive charge of E2, electrostatic interaction with heparan sulfate can be reduced, resulting in decreased binding to heparan sulfate. Candidate positively charged amino acids in this region include lysines at residues 63, 70, 76, 84, 97, 104, 129, 131, 133, 139, 148, 149, 159 and arginine at residues 65, 92, 128, 137, 157, 170, 172 (Bear et al., Virology 347: 183-190, 2006). At least several of these amino acids are directly implicated in E2 binding to heparan sulfate. Net positive charge can be reduced by deletion of lysine or arginine or substitution of lysine or arginine with a neutral or negatively charged amino acid. For example, one or more of these lysines and arginines may be replaced with glutamic or aspartic acid. Certain embodiments have at least one substitution of lysine 70, 76 or 159. In cases where E2 is expressed as a polyprotein with E3, the lysine located adjacent to the natural E3/E2 cleavage site is maintained— that is, the recognition sequence and cleavage site is unaltered. Alternatively, the native endopeptidase cleavage site sequence is replaced with a recognition sequence for a different endopeptidase.

Certain variants of E2 are also modified in a way that positively impacts binding to dendritic cells. Alteration of the glutamic acid found at residue 160 in the reference HR sequence can improve binding to dendritic cells (see Gardner et al., J Virol 74, 11849, 2000). Alterations, such as a deletion of residue 160 or substitution of residue 160 are found in certain variants. In particular variants, a non-charged amino acid is substituted for Glu, in other variants, a non-acidic amino acid is substituted for Glu. Typically, Glu160 is replaced with one of the small or aliphatic amino acids, including glycine, alanine, valine, leucine or isoleucine.

Other variants comprise two or more amino acid alterations. Typically in these variants one of the alterations is Glu160 and the remaining alteration(s) are changes of one or more of the lysines and arginines in the region spanning residue about 50 to about 180. Certain of the variants comprise an alteration of Glu160 to a non-acidic residue or deletion and one or more alterations of lysine 70, lysine 76, or lysine 159 with a non-basic amino acid. Some specific variants comprise a Glu160 to Gly, Lys 70 to Glu, and Lys 159 to Glu; a Glu 160 to Gly, Lys 70, 76 and 159 to Glu; a deletion of Glu 160 and Lys 70 and 159 to Glu; and a deletion of Glu 160 and Lys 70, 76, and 159 to Glu.

In certain cases, E2 protein is first expressed as a polyprotein in fusion with at least E3 or in fusion with a leader sequence. Regardless of whether the leader sequence is E3 or another sequence, E2 in the viral envelope should be free of the E3 or other leader sequence. In other words, E2 is preferably not an E3/E2 fusion protein (e.g., the E3/E2 fusion protein called SVGmu). In certain embodiments, E2 is expressed as part of E3-E2-6K-E1 polyprotein. Sindbis virus naturally expresses E2 as part of a polyprotein and the junction regions for E3/E2, E2/6K, and 6K/E1 have sequences recognized and cleaved by endopeptidases. Normally, the E3/E2 junction is cleaved by furin or a furin-like serine endopeptidase between residues 65 and 66. Furin has specificity for paired arginine residues that are separated by two amino acids. To maintain E3/E2 cleavage by furin, residues 62-66 (RSKRS; SEQ ID NO: 26) should maintain the two arginine residues with two amino acid separation and the serine residue. Alternatively, a different cleavage sequence can be used in place of the E3/E2 furin cleavage sequence or any of the other cleavage sequences. Recognition and cleavage sites can be incorporated for endopeptidases, including, without limitation, aspartic endopeptidases (e.g., cathepsin D, chymosin, HIV protease), cysteine endopeptidases (bromelains, papain, calpain), metalloendopeptidases, (e.g., collagenase, thermolysin), serine endopeptidases (e.g., chymotrypsin, factor IXa, factor X, thrombin, trypsin), streptokinases. The recognition and cleavage site sequences for these enzymes are well known.

Amino acids in E2, other than those already mentioned, may also be altered. Generally, a variant E2 sequence will have at least 80% sequence amino acid identity to the reference E2 sequence, or it may have at least 82%, at least 85%, at least 87%, at least 90%, at least 92%, at least 95%, or at least 98% sequence identity. The variant glycoprotein should exhibit biological function, such as the ability to facilitate infection of dendritic cells by a viral particle having an envelope comprising E2. Experiments have identified regions of envelope glycoproteins that appear to have an important role in various aspects of viral assembly, attachment to cell surface, and infection. When making variants, the following information can be used as guidelines. The cytoplasmic tail of E2—approximately residues 408 to 415—is important for virus assembly (West et al. J Virol 80: 4458-4468, 2006; 8). Other regions are involved in forming secondary structure (approximately residues 33-53); and involved in transport and protein stability (approximately residues 86-119) (Navaratmarajah et al., J Virol 363: 124-147, 2007). The variant may retain hydrophobic character of a region that spans the membrane, approximately residues 370-380. The variant may retain one or both N-linked glycosylation sites residues NIT (residues 196-198) and NFT (residues 318-320) and may retain one or more of the sites that are palmitoylated (C-396, C416 and C417) (Strauss and Strauss Microbiol Rev 58, 491-562, 1994; pp. 499-509). On the other hand, many regions of E2 may be altered without deleterious event. For example, insertions of transposons at many different locations in E2 still resulted in viable virus (Navaratmarajah, ibid).

In certain embodiments, a tag peptide may be incorporated into E3, 6K, or E1 proteins. For some purposes, a tag may be incorporated into E2, but a tag is not desirable for use in a product for administration to human patients. A tag peptide, which is a short sequence (e.g., 5-30 amino acids), can be used to facilitate detection of envelope expression and its presence in viral particles. For detection purposes, a tag sequence will typically be detectable by antibodies or chemicals. Another use for a tag is to facilitate purification of viral particles A substrate containing a binding partner for the tag can be used to absorb virus. Elution of the virus can be accomplished by treatment with a moiety that displaces the tag from the binding partner or when the tag sequence is in linkage with a cleavable sequence, treatment with the appropriate endopeptidase will conveniently allow release of virus. (See, for example, Qiagen catalog, Factor Xa Protease System). Removal of the tag peptide is generally desirable for safety purposes of the virus particles use in animal subjects. If the tag is not removed, an immune response to the tag may occur.

Suitable tags include, without limitation, FLAG (DYKDDDDK) (SEQ ID NO: 28) (U.S. Pat. No. 4,703,004), for which antibodies are commercially available, chitin binding protein, maltose binding protein, glutathione-S-transferase, poly(His) (U.S. Pat. No. 4,569,794), thioredoxin, HA (hemagglutinin)-tag, among others. Poly (His) can be adsorbed onto affinity media containing bound metal ions, e.g., nickel or cobalt, and eluted with a low pH medium.

The viral particles may be evaluated to determine the specificity of the envelope glycoprotein incorporated into the virus that targets dendritic cells. For example, a mixed population of bone marrow cells can be obtained from a subject and cultured in vitro. Alternatively, isogenic cells lines that express or don't express DC-SIGN can be obtained and used. The recombinant virus can be administered to the mixed population of bone marrow cells or isogenic cell lines, and expression of a reporter gene incorporated into the virus can be assayed in the cultured cells. Certain embodiments may employ a limiting dilution analysis, in which the mixed population of cells is split into separate parts, which are then separately incubated with decreasing amounts of virus (e.g., 2-fold, 5-fold, 10-fold less virus in each part). In some embodiments, at least about 50%, more preferably at least about 60%, 70%, 80% or 90%, still more preferably at least about 95% of infected cells in the mixed cell population are dendritic cells that express DC-SIGN. In certain embodiments, the ratio of infected dendritic cells to infected non-dendritic cells (or non DC-SIGN expressing cells) is at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 40:1, at least about 50:1, at least about 100:1, at least about 200:1, at least about 500:1, at least about 1000:1, at least about 5000:1, at least about 10,000:1, or more. For limiting dilution, greater selectivity is typically seen at higher dilutions (i.e., lower amounts of input virus.

Activity of pseudotyped viral particles can be determined by any of a variety of techniques. For example, a preferred method to measure infectivity efficiency (IU, infectious units) is by administering viral particles to cells and measuring expression of a product encoded in the vector genome. Any product that can be assayed may be used. One convenient type of product is a fluorescent protein, such as green fluorescent protein (GFP). GFP and assay is exemplified in the Examples. Other products that can be used include proteins expressed on a cell surface (e.g., detection by antibody binding), enzymes, and the like. For the detection of IL-12, an IL-12 detection assays (e.g. ELISA) or biological function assays (see e.g. Example 1) can be used. Where the product includes an antigen and cells are dendritic cells, infectivity/activity can be assessed by determining an antigen specific immune response. Furthermore, it is possible to ascertain side effects in a mammal. The ability to specifically target dendritic cells can also be tested directly, for example, in cell culture as described below.

Viral particles can also be prepared and tested for their selectivity and/or their ability to facilitate penetration of the target cell membrane. Viral particles that have an envelope with unmodified glycoproteins can be used as controls for comparison. Briefly, cells expressing a receptor for an envelope glycoprotein are infected by the virus using a standard infection assay. After a specified time, for example 48 hours post-infection, cells can be collected and the percentage of cells infected by the virus can be determined by flow cytometry, for example. Selectivity can be scored by calculating the percentage of cells infected by virus. Similarly, the effect of a variant envelope glycoprotein on viral titer can be quantified by dividing the percentage of cells infected by virus comprising a variant envelope by the percentage of cells infected by virus comprising the corresponding wild type (unmodified) envelope glycoprotein. A particularly suitable variant will have the best combination of selectivity and infectious titer. Once a variant is selected, viral concentration assays may be performed to confirm that these viruses can be concentrated without compromising activity. Viral supernatants are collected and concentrated by ultracentrifugation. The titers of viruses can be determined by limited dilution of viral stock solution and infection of cells expressing the receptor for the envelope glycoprotein, measuring the expression of a product expressed by the viruses as described above.

The entry of a lentiviral vector particle into a target cell is another type of evaluation of activity. BlaM-Vpr (beta-lactamase Vpr) fusion protein has been utilized to evaluate HIV-1 viral penetration; a fusion of BlaM and a Sindbis virus envelope glycoprotein, such as E1 or an E2/E1 fusion protein can be used to assess the efficacy of an envelope protein in facilitating fusion and penetration into a target cell. Viral particles may be prepared, for example, by transient transfection of packaging cells with one or more vectors comprising the viral elements, BlaM-Vpr, and the variant envelope of interest (and an affinity molecule if appropriate). The resulting viruses can be used to infect cells expressing a molecule the targeting molecule (or affinity molecule) specifically binds in the absence or presence of the free inhibitor of binding (such as an antibody). Cells can then be washed with $CO_2$-independent medium and loaded with CCF2 dye (Aurora Bioscience). After incubation at room temperature to allow completion of the cleavage reaction, the cells can be fixed by paraformaldehyde and analyzed by flow cytometry and microscopy. The presence of blue cells indicates the penetration of viruses into the cytoplasm; fewer blue cells would be expected when blocking antibody is added (Cavrois et al. Nat Biotechnol 20: 1151-1154, 2002).

To investigate whether penetration is dependent upon a low pH, and to identify envelope glycoproteins with the desired pH dependence, $NH_4Cl$ or other compound that alters pH can be added at the infection step ($NH_4Cl$ will neutralize the acidic compartments of endosomes). In the case of $NH_4Cl$, the disappearance of blue cells will indicate that penetration of viruses is low pH-dependent. In addition, to confirm that the activity is pH-dependent, lysosomotropic agents, such as ammonium chloride, chloroquine, concanamycin, bafilomycin Al, monensin, nigericin, etc., may be added into the incubation buffer. These agents elevate the pH within the endosomal compartments (e.g., Drose and Altendorf, J. Exp. Biol. 200, 1-8, 1997). The inhibitory effect of these agents will reveal the role of pH for viral fusion and entry. The different entry kinetics between viruses displaying different fusogenic molecules may be compared and the most suitable selected for a particular application.

PCR-based entry assays can be utilized to monitor reverse transcription and measure kinetics of viral DNA synthesis as an indication of the kinetics of viral entry. For example, viral particles comprising a particular envelope protein molecule are incubated with target cells, such as 293T cells, DCs, or any other cells that have been engineered to express, or which naturally express, the appropriate binding partner (receptor) for the envelope protein molecule. Either immediately, or after a time increment (to allow infection to occur), unbound viruses are removed and aliquots of the cells are analyzed for viral nucleic acids. DNA is extracted from these aliquots and subjected to amplification analysis, generally in a semi-quantitative assay, primed with LTR-specific primers. The appearance of LTR-specific DNA products indicates the success of viral entry.

B. Lentiviral Vector Genome

The viral vector particle comprises a genome, which comprises the sequence encoding IL-12, such as scIL-12, and optionally one or more other sequences of interest. Other sequences may be included, such as sequences that allow the genome to be packaged into the virus particle and sequences that promote expression of the sequence(s) of interest following transduction of the target cell. The genome can be derived from any of a large number of suitable, available lentiviral genome based vectors, including those identified for human gene therapy applications, such as those described by Pfeifer and Verma (Annu. Rev. Genomics Hum. Genet. 2:177-211, 2001). For the sake of simplicity, the genome is also referred to as "viral vector genome" or "vector genome".

1. Backbone

Suitable lentiviral vector genomes include those based on Human Immunodeficiency Virus (HIV-1), HIV-2, feline immunodeficiency virus (FIV), equine infectious anemia virus, Simian Immunodeficiency Virus (SIV) and maedi/visna virus. A desirable characteristic of lentiviruses is that they are able to infect both dividing and non-dividing cells, it is not necessary for target cells to be dividing (or to stimulate the target cells to divide). Generally, the genome and envelope glycoproteins will be based on different viruses, such that the resulting viral vector particle is pseudotyped. Safety features of the vector genome are desirably incorporated. Safety features include self-inactivating LTR and a integration deficient genome/particle. Exemplary vectors are described in WO 2011/011584 and such vectors may be used in embodiments of the invention for expression of sequences of interest, including IL-12, other immunostimulatory molecules, cytokines and antigens of interest.

In some exemplary embodiments, the viral vector genome comprises sequences from a lentivirus genome, such as the HIV-1 genome or the SIV genome. The viral genome construct may comprise sequences from the 5' and 3' LTRs of a lentivirus, and in particular may comprise the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Typically, the LTR sequences are HIV LTR sequences.

The vector genome may comprise an inactivated or self-inactivating 3' LTR (Zufferey et al. J Virol 72: 9873, 1998; Miyoshi et al., J Virol 72:8150, 1998). A self-inactivating vector generally has a deletion of the enhancer and promoter sequences from the 3' long terminal repeat (LTR), which is copied over into the 5' LTR during vector integration. In one instance, the U3 element of the 3' LTR contains a deletion of its enhancer sequence, the TATA box, Sp1 and NF-kappa B sites. As a result of the self-inactivating 3' LTR, the provirus that is generated following entry and reverse transcription will comprise an inactivated 5' LTR. The rationale is to improve safety by reducing the risk of mobilization of the vector genome and the influence of the LTR on nearby cellular promoters. The self-inactivating 3' LTR may be constructed by any method known in the art.

Optionally, the U3 sequence from the lentiviral 5' LTR may be replaced with a promoter sequence in the viral construct, such as a heterologous promoter sequence. This can increase the titer of virus recovered from the packaging cell line. An enhancer sequence may also be included. Any enhancer/promoter combination that increases expression of the viral RNA genome in the packaging cell line may be used. In one example, the CMV enhancer/promoter sequence is used (U.S. Pat. Nos. 5,385,839 and 5,168,062).

In certain embodiments, the risk of insertional mutagenesis is minimized by constructing the lentiviral vector genome to be integration defective. A variety of approaches can be pursued to produce a non-integrating/integration deficient vector genome. These approaches entail engineering a mutation(s) into the integrase enzyme component of the pol gene, such that it encodes a protein with an inactive integrase. The vector genome itself can be modified to prevent integration by, for example, mutating or deleting one or both attachment sites, or making the 3' LTR-proximal polypurine tract (PPT) non-functional through deletion or modification. In addition, non-genetic approaches are available; these include pharmacological agents that inhibit one or more functions of integrase. The approaches are not mutually exclusive, that is, more than one of them can be used at a time. For example, both the integrase and attachment sites can be non-functional, or the integrase and PPT site can be non-functional, or the attachment sites and PPT site can be non-functional, or all of them can be non-functional.

As stated above, one approach is to make and use a non-functional integrase. Integrase is involved in cleavage of viral double-stranded blunt-ended DNA and joining the ends to 5'-phosphates in the two strands of a chromosomal target site. Integrase has three functional domains: N-terminal domain, which contains a zinc-binding motif (HHCC), the central domain core, which contains the catalytic core and a conserved DD35E motif (D64, D116, E152 in HIV-1), and a C-terminal domain, which has DNA binding properties. Point mutations introduced into integrase are sufficient to disrupt normal function. Many integrase mutations have been constructed and characterized (see, Philpott and Thrasher, Human Gene Therapy 18:483, 2007; Apolonia, Thesis submitted to University College London, April 2009, pp, 82-97; Engelman et al. J Virol 69: 2729, 1995; Nightingale et al. Mol Therapy, 13: 1121, 2006). The sequence encoding the integrase protein can be deleted or mutated to render the protein inactive, preferably without significantly impairing reverse transcriptase activity or nuclear targeting, thereby only preventing integration of the provirus into the target cell genome. Acceptable mutations can reduce integrase catalysis, strand transfer, binding to att sites, binding to host chromosomal DNA, and other functions. For example, a single aspartic acid to asparagine substitution at residue 35 of HIV or SIV integrase completely abolishes viral DNA integration. Deletions of integrase will generally be confined to the C-terminal domain. Deletion of coding sequence for residues 235-288 result in a useful non-functional integrase (Engelman et al. J Virol 69:2729, 1995). As further examples, mutations can be generated, for example, Asp64 (residue numbers are given for HIV-1, corresponding residue numbers for integrase from other lentiviruses or retroviruses can be readily determined by one of ordinary skill) (e.g., D64E, D64V), Asp116 (e.g., D116N), Asn120 (e.g., N120K), Glu152, Gln148 (e.g., Q148A), Lys156, Lys159, Trp235 (e.g. W235E), Lys264 (e.g., K264R), Lys266 (e.g., K266R), Lys273 (e.g., K273R). Other mutations can be constructed and tested for integration, transgene expression, and any other desirable parameter. Assays for these functions are well known. Mutations can be generated by any of a variety of techniques, including site-directed mutagenesis and chemical synthesis of nucleic acid sequence. One mutation may be made or more than one of these mutations can be present in integrase. For example, an integrase may have mutations at two amino acids, three amino acids, four amino acids, and so on.

Alternatively or in combination with the use of integrase mutant(s), the attachment sites (att) in U3 and U5 can also be mutated. Integrase binds to these sites and the 3'-terminal dinucleotide is cleaved at both ends of the vector genome. A CA dinucleotide is located at the recessed 3' end; the CA is required for processing, mutation of the nucleotides blocks integration into the host chromosome. The A of the CA dinucleotide is the most critical nucleotide for integration, and mutations at both ends of the genome will give the best results (Brown et al J Virol 73:9011 (1999). In one exemplification, the CA at each end is changed to TG. In other exemplifications, the CA at each end is changed to TG at one end and GT at the other end. In other exemplifications, the CA at each end is deleted; in other exemplifications, the A of the CA is deleted at each end.

Integration can also be inhibited by mutation or deletion of polypurine tract (PPT) (WO 2009/076524), located proximally to the 3' LTR. The PPT is a polypurine sequence of about 15 nucleotides that can serve as a primer binding site for plus-strand DNA synthesis. In this case, mutations or deletions of PPT targets the reverse transcription process. Without wishing to be held to a mechanism, by mutating or deleting PPT, production of linear DNA is radically reduced and essentially only 1-LTR DNA circles are produced. Integration requires a linear double-stranded DNA vector genome, and integration is essentially eliminated without it.

As stated above, a PPT can be made non-functional by mutation or by deletion. Typically, the entire about 15 nt PPT is deleted, although in some embodiments, shorter deletions of 14 nt, 13, nt, 12 nt, 11 nt, 10 nt, 9 nt, 8 nt, 7 nt, 6 nt, 5 nt, 4 nt, 3 nt and 2 nt may be made. When mutations are made, typically multiple mutations are made, especially in the 5' half of the PPT (McWilliams et al., J Virol 77:11150, 2003), although single and double mutations in the first four bases still reduce transcription. Mutations made at the 3' end of PPT generally have a more dramatic effect (Powell and Levin J Virol 70:5288, 1996).

These different approaches to make a vector genome non-integrating can be used individually or in combination. Using more than one approach may be used to build a fail-safe vector through redundant mechanisms. Thus, PPT mutations or deletions can be combined with att site mutations or deletions or with Integrase mutations or PPT mutations or deletions can be combined with both att site mutations or deletions and Integrase mutations. Similarly, att site mutations or deletions and Integrase mutations may be combined with each other or with PPT mutations or deletions.

2. Regulatory Elements

As discussed herein, the viral vector genome comprises a sequence encoding IL-12 and optionally one or more other nucleic acids of interest that is desirable to express in target cells. For simplicity, the term "sequence of interest" (SOI) is used to mean IL-12 and, in certain embodiments, one or more other sequences of interest (such as one or more other immunostimulatory molecules, cytokines or one or more antigens). Typically, the sequences of interest are located between the 5' LTR and 3' LTR sequences. Further, the sequence encoding IL-12 and any other sequence of interest is preferably in a functional relationship with other genetic elements, for example transcription regulatory sequences including promoters or enhancers, to regulate expression of the sequence of interest in a particular manner. In certain instances, the useful transcriptional regulatory sequences are those that are highly regulated with respect to activity, both temporally and spatially. Expression control elements that may be used for regulating the expression of the components are known in the art and include, but are not limited to, inducible promoters, constitutive promoters, secretion signals, enhancers and other regulatory elements.

The sequence of interest and any other expressible sequence is typically in a functional relationship with internal promoter/enhancer regulatory sequences. An "internal" promoter/enhancer is one that is located between the 5' LTR and the 3' LTR sequences in the viral vector construct and is operably linked to the sequence of interest. The internal promoter/enhancer may be any promoter, enhancer or promoter/enhancer combination known to increase expression of a gene with which it is in a functional relationship. A "functional relationship" and "operably linked" mean, without limitation, that the sequence is in the correct location and orientation with respect to the promoter and/or enhancer that the sequence of interest will be expressed when the promoter and/or enhancer is contacted with the appropriate molecules.

The choice of an internal promoter/enhancer is based on the desired expression pattern of the sequence of interest and the specific properties of known promoters/enhancers. Thus, the internal promoter may be constitutively active. Non-limiting examples of constitutive promoters that may be used include the promoter for ubiquitin (U.S. Pat. No. 5,510,474; WO 98/32869), CMV (Thomsen et al., PNAS 81:659, 1984; U.S. Pat. No. 5,168,062), beta-actin (Gunning et al. 1989 Proc. Natl. Acad. Sci. USA 84:4831-4835) and pgk (see, for example, Adra et al. 1987 Gene 60:65-74; Singer-Sam et al. 1984 Gene 32:409-417; and Dobson et al. 1982 Nucleic Acids Res. 10:2635-2637).

Alternatively, the promoter may be a tissue specific promoter. In some preferred embodiments, the promoter is a target cell-specific promoter. For example, the promoter can be from any product expressed by dendritic cells, including CD11c, CD103, TLRs, DC-SIGN, BDCA-3, DEC-205, DCIR2, mannose receptor, Dectin-1, Clec9A, MHC Class II. In addition, promoters may be selected to allow for inducible expression of the sequence of interest. A number of systems for inducible expression are known in the art, including the tetracycline responsive system, the lac operator-repressor system, as well as promoters responsive to a variety of environmental or physiological changes, including heat shock, metal ions, such as metallothionein promoter, interferons, hypoxia, steroids, such as progesterone or glucocorticoid receptor promoter, radiation, such as VEGF promoter. A combination of promoters may also be used to obtain the desired expression of the gene of interest. The artisan of ordinary skill will be able to select a promoter based on the desired expression pattern of the gene in the organism or the target cell of interest.

The viral genome may comprise at least one RNA Polymerase II or III responsive promoter. This promoter can be operably linked to the sequence of interest and can also be linked to a termination sequence. In addition, more than one RNA Polymerase II or III promoters may be incorporated. RNA polymerase II and III promoters are well known to one of skill in the art. A suitable range of RNA polymerase III promoters can be found, for example, in Paule and White, Nucleic Acids Research, Vol. 28, pp 1283-1298 (2000). RNA polymerase II or III promoters also include any synthetic or engineered DNA fragment that can direct RNA polymerase II or III to transcribe downstream RNA coding sequences. Further, the RNA polymerase II or III (Pol II or III) promoter or promoters used as part of the viral vector genome can be inducible. Any suitable inducible Pol II or III promoter can be used with the methods of the invention. Particularly suited Pol II or III promoters include the tetracycline responsive promoters provided in Ohkawa and Taira, Human Gene Therapy, Vol. 11, pp 577-585 (2000) and in Meissner et al. Nucleic Acids Research, Vol. 29, pp 1672-1682 (2001).

An internal enhancer may also be present in the viral construct to increase expression of the gene of interest. For example, the CMV enhancer (Boshart et al. Cell, 41:521, 1985) may be used. Many enhancers in viral genomes, such as HIV, CMV, and in mammalian genomes have been identified and characterized (see GenBank). An enhancer can be used in combination with a heterologous promoter. One of ordinary skill in the art will be able to select the appropriate enhancer based on the desired expression pattern.

A viral vector genome will usually contain a promoter that is recognized by the target cell and that is operably linked to the sequence of interest, viral components, and other sequences discussed herein. A promoter is an expression control element formed by a nucleic acid sequence that permits binding of RNA polymerase and transcription to occur. Promoters may be inducible, constitutive, temporally active or tissue specific. The activity of inducible promoters is induced by the presence or absence of biotic or abiotic factors. Inducible promoters can be a useful tool in genetic engineering because the expression of genes to which they are operably linked can be turned on or off at certain stages of development of an organism, its manufacture, or in a particular tissue. Inducible promoters can be grouped as chemically-regulated promoters, and physically-regulated promoters. Typical chemically-regulated promoters include, not are not limited to, alcohol-regulated promoters (e.g., alcohol dehydrogenase I (alcA) gene promoter), tetracycline-regulated promoters (e.g., tetracycline-responsive promoter), steroid-regulated promoter (e.g., rat glucocorticoid receptor (GR)-based promoter, human estrogen receptor (ER)-based promoter, moth ecdysone receptor-based promoter, and the promoters based on the steroid/retinoid/thyroid receptor superfamily), metal-regulated promoters (e.g., metallothionein gene-based promoters), and pathogenesis-related promoters (e.g., *Arabidopsis* and maize pathogen-related (PR) protein-based promoters). Typical physically-regulated promoters include, but are not limited to, temperature-regulated promoters (e.g., heat shock promoters), and light-regulated promoters (e.g., soybean SSU promoter). Other exemplary promoters are described elsewhere, for example, in "Promoters used to regulate gene expression" on Patent Lens web site, accessed 18 May 2009.

One of skill in the art will be able to select an appropriate promoter based on the specific circumstances. Many different promoters are well known in the art, as are methods for operably linking the promoter to the gene to be expressed. Both native promoter sequences and many heterologous promoters may be used to direct expression in the packaging cell and target cell. Heterologous promoters are preferred, however, as they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system. In some embodiments, the promoter is a dendritic cell-specific promoter. The dendritic cell-specific promoter can be, for example, CD11c promoter.

Transcription may be increased by inserting an enhancer sequence into the vector(s). Enhancers are typically cis-acting elements of DNA, usually about 10 to 300 bp in length, that act on a promoter to increase its transcription. Many enhancer sequences are now known from mammalian genes (globin, elastase, albumin, alpha-fetoprotein, and insulin) and from eukaryotic cell viruses. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors may also contain sequences necessary for the termination of transcription and for stabilizing the mRNA. These sequences are often found in the 5' and, occasionally 3', untranslated regions of eukaryotic or viral DNAs or cDNAs and are well known in the art.

The viral vector genome may also contain additional genetic elements. The types of elements that may be included in the construct are not limited in any way and may be chosen to achieve a particular result. For example, a signal that facilitates nuclear entry of the viral genome in the target cell may be included. An example of such a signal is the HIV-1 cPPT/CTS signal (DNA flap). Further, elements may be included that facilitate the characterization of the provirus integration site in the target cell. For example, a tRNA amber suppressor sequence may be included in the construct. An insulator sequence from e.g., chicken β-globin may also be included in the viral genome construct. This element reduces the chance of silencing an integrated provirus in the target cell due to methylation and heterochromatinization effects. In addition, the insulator may shield the internal enhancer, promoter and exogenous gene from positive or negative positional effects from surrounding DNA at the integration site on the chromosome. In addition, the vector genome may contain one or more genetic elements designed to enhance expression of the gene of interest. For example, a woodchuck hepatitis virus responsive element (WRE) may be placed into the construct (Zufferey et al. 1999. J. Virol. 74:3668-3681; Deglon et al. 2000. Hum. Gene Ther. 11:179-190).

The viral vector genome is typically constructed in a plasmid form that may be transfected into a packaging or producer cell line. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline.

Plasmids containing one or more of the components described herein are readily constructed using standard techniques well known in the art. For analysis to confirm correct sequences in plasmids constructed, the plasmid may be replicated in *E. coli*, purified, and analyzed by restriction endonuclease digestion or its DNA sequence determined by conventional methods.

Vectors constructed for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the antigen-specific polynucleotide in the expression vector. See Sambrook et al., supra, pp. 16.17-16.22. Other vectors and methods suitable for adaptation to the expression of polypeptides are well known in the art and are readily adapted to the specific circumstances.

Using the teachings provided herein, one of skill in the art will recognize that the efficacy of a particular expression system can be tested by transfecting packaging cells with a vector comprising a gene encoding a reporter protein and measuring the expression using a suitable technique, for example, measuring fluorescence from a green fluorescent protein conjugate. Suitable reporter genes are well known in the art.

3. Types of Sequences of Interest

The retroviral vectors described herein encode IL-12 and optionally, other sequences of interest including, but not limited to, immunostimulatory molecules, cytokines, chemokines, antigens of interest, checkpoint inhibitors, etc. Polynucleotide sequences encoding IL-12 are known in the art and available in public databases. As would be readily understood by the person of ordinary skill in the art, IL-12 is a heterodimeric cytokine with multiple biological effects on the immune system. It is composed of two subunits, p35 and p40, both of which are required for the secretion of the active form of IL-12, p70. In one embodiment the IL-12 sequence (expression cassette) comprises a polynucleotide that directs expression of IL-12 polypeptide. Any IL-12 polypeptide including variants and derivatives of known IL-12 molecules can be used, where variants and derivatives retain IL-12 activity. IL-12 activity can be measured using assays known in the art (e.g., such as described in Example 1). In one embodiment, the IL-12 is human IL-12. In another embodiment, the IL-12 is murine IL-12. In one embodiment the polynucleotide comprises the sequence of both IL-12 subunits, p35 and p40, separated by an IRES sequence which permits expression of multiple transgenes from a single transcript. In particular embodiments the vectors described herein encode a single chain IL-12 (scIL-12). In this regard the single chain fusion protein may encode IL-12 subunits in either orientation, and in certain embodiments may include a linker between the 2 subunits, such as p35-L-p40 or p40-L-p35. A "linker" is a peptide that joins or links other peptides or polypeptides, such as a linker of about 2 to about 150 amino acids. Any of a variety of linkers are known in the art and can be used herein (see e.g., Adv Drug Deliv Rev. 2013 October; 65(10):1357-69). In certain embodiments, the linker is an elastin linker.

Other sequences of interest may also be included in the viral vectors described herein. Thus, in this regard the sequence of interest is not limited in any way and includes any nucleic acid that one of ordinary skill desires to have transcribed and expressed in the target cell. The product can be a protein or a nucleic acid. The sequence of interest can encode a protein or a nucleic acid molecule, including siRNA, microRNA, a self-complementary double stranded RNA in which the complementary region is greater than about 20 ribonucleotides in length, or an RNA that is complementary to a message RNA, where binding of said complementary (anti-sense) RNA to the message RNA blocks its ability to be translated into protein. In some instances, the sequence of interest can encode an antigen against which an immune response is desired. In particular, tumor antigens and infectious diseases antigens from agents such as HIV, HSV, HCV, HPV, malaria, or tuberculosis are desirable.

In certain cases, the sequence of interest can be a gene encoding a small inhibiting RNA (siRNA) or a microRNA (miRNA) of interest that down-regulates expression of a molecule. For example, the gene encoding an siRNA or a microRNA can be used to down-regulate expression of negative regulators in a cell, including those that inhibit activation or maturation of dendritic cells. siRNAs and microRNAs are well known in the art (Fire et al., Nature 391:806, 1998; see also "The RNA Interference Resource" of Applied Biosystems, Trang et al., Oncogene Suppl 2:S52, 2008; Taganov, K., et al. 2007. Immunity 26:133-137; Dahlberg, J. E. and E. Lund. 2007. Sci. STKE 387:pe25; Tiemann and Rossi, EMBO Mol Med 1: 142, 2009). Alternatively, the sequence of interest can encode a self-complementary double stranded RNA in which the complementary region is greater than about 20 ribonucleotides in length, or an anti-sense RNA that is greater than about 20 ribonucleotides in length. Those of ordinary skill in the art will appreciate that siRNA, miRNA, dsRNA and anti-sense RNA molecules can be expressed from an RNA polymerase III promoter, or, alternatively, can be a component of a non-coding RNA that is transcribed from an RNA polymerase II promoter.

Additionally, the sequence of interest includes a sequence encoding IL-12 and may additionally include sequences that encode more than one product. In some configurations, the sequence to be delivered can comprise multiple genes encoding at least one protein, at least one siRNA, at least one microRNA, at least one dsRNA or at least one anti-sense RNA molecule or any combinations thereof. For example, the sequence to be delivered can include IL-12 and one or more genes that encode one or more antigens against which an immune response is desired. The one or more antigens can be associated with a single disease or disorder, or they can be associated with multiple diseases and/or disorders. In some instances, a gene encoding an immune regulatory protein can be included along with a gene encoding an antigen against which an immune response is desired, and the combination can elicit and regulate the immune response to the desired direction and magnitude. Thus, in certain embodiments, the vector may include a sequence encoding IL-12, a sequence encoding an antigen and the sequence encoding an immunomodulatory protein. The products may be produced as an initial fusion product in which the encoding sequence is in functional relationship with one promoter. Alternatively, the products may be separately encoded and each encoding sequence in functional relationship with a promoter. The promoters may be the same or different.

As noted elsewhere, in certain embodiments, the viral vectors described herein comprise a sequence encoding IL-12 and a sequence of interest encoding one or more antigens associated with the disease or disorder. Any antigen that is associated with a disease or disorder can be delivered to dendritic cells using the viral particles as described herein. An antigen that is associated with the disease or disorder is identified. Antigens associated with many diseases and disorders are well known in the art. An antigen may be previously known to be associated with the disease or disorder, or may be identified by any method known in the art. For example, an antigen to a type of cancer from which a patient is suffering may be known, such as a tumor-associated antigen or may be identified from the tumor itself by any of a variety of methods known in the art.

Tumor-associated antigens are known for a variety of cancers including, for example, renal cell carcinoma, prostate cancer, melanoma, and breast cancer. In some breast cancers, for example, the Her-2 receptor is overexpressed on the surface of cancerous cells. Exemplary tumor antigens include, but are not limited to, prostatic acid phosphatase, prostate specific antigen, NKX3.1, prostate specific membrane antigen, PRAME; BAGE; RAGE, NY-ESO-1, SAGE, HAGE, GAGE, Plu-1, HASH-1, HasH-2, Cripto, Criptin, MART-1/Melan-A, gp100, gp75, mda-7, tyrosinase, tyrosinase-related protein, p53, Ras, c-Myc, A-Raf, B-Raf, and C-Raf, MAGE-A1, MAGE-A2, MAGE-A3, MAGE-A4, MAGE-A6, MAGE-A10, MAGE-A12, MART-1, BAGE, DAM-6, -10, GAGE-1, GAGE-2, GAGE-8, GAGE-3, GAGE-4, GAGE-5, GAGE-6, GAGE-7B, NA88-A, MART-1, MC1R, Gp100, PSM, TRP-1, TRP-2, ART-4, CAMEL, CEA, Cyp-B, hTERT, hTRT, iCE, MUC1, MUC2, PRAME, P15, RU1, RU2, SART-1, SART-3, Wilms' tumor antigen (WT1), AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, SART-2, TRP-2/ INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, Epidermal Growth Factor receptor (EGFR and EGFRvIII), platelet derived growth factor receptor (PDGFR), vascular endothelial growth factor receptor (VEGFR), integrin-linked kinase (ILK), STAT3, STAT5, STAT6, HIF-1, HIF-2, Nuclear Factor-Kappa B (NF-κB), Notch1-4, c-Met, mammalian targets of rapamycin (mTOR), WNT, PMSA, PR-3, MDM2, Mesothelin, renal cell carcinoma-5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGs5, SART3, STn, PAX5, OY-TES1, sperm protein 17, LCK, HMWMAA, AKAP-4, SSX2, XAGE 1, B7H3, legumain, TIE2, Page4, MAD-CT-1, FAP, MAD-CT-2, and fos related antigen 1 A number of tumor associated antigens have been reviewed (see, for example, "Tumor-Antigens Recognized By T-Lymphocytes," Boon T, Cerottini J C, Vandeneynde B, Vanderbruggen P, Vanpel A, Annual Review Of Immunology 12: 337-365, 1994; "A listing of human tumor antigens recognized by T cells," Renkvist N, Castelli C, Robbins P F, Parmiani G. Cancer Immunology Immunotherapy 50: (1) 3-15 Mar. 2001.) The antigen can also be an antigen associated with an infectious disease, such as, for example, HIV/AIDS. The antigen can be, for example, gp120 (Klimstra, W. B., et al. 2003. J Virol 77:12022-12032; Bernard, K. A., et al. 2000. Virology 276:93-103; Byrnes, A. P., et al. 1998. J Virol 72: 7349-7356). Other exemplary antigens include, but are not limited to: gag, pol, env, tat, nef and rev (Lieberman, J. et al. 1997. AIDS Res Hum Retroviruses 13(5): 383-392; Menendez-Arias, L. et al. 1998. Viral Immunol 11(4): 167-181).

Examples of viral antigens include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, or a hepatitis C virus E1 or E2 glycoproteins, core, or non-structural proteins, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides, e.g., *P. falciparum* circumsporozoite (PfCSP), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite antigens include, but are not limited to, polypeptides (including protective antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

Once an antigen has been identified and selected, a sequence that encodes the desired antigen is identified. Preferably the sequence comprises a cDNA. The sequences then cloned into the viral vector genome using standard methodologies known in the art.

In certain configurations, vectors contain polynucleotide sequences that encode immunomodulatory molecules. Exemplary immunomodulatory molecules include any of a variety of cytokines. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11; IL-15, a tumor necrosis factor such as TNF-alpha or TNF-beta; and other polypeptide factors including LIF and kit ligand (KL). Other immunomodulatory molecules contemplated for use herein include B7.1, B7.2, 4-1BB, CD40 ligand (CD40L), drug-inducible CD40 (iCD40), and the like. In certain embodiments, these polynucleotides are typically under the control of one or more regulatory elements that direct the expression of the coding sequences in dendritic cells.

In certain embodiments, the immunomodulatory molecule encoded by the vectors expressing IL-12 described herein is a checkpoint inhibitor molecule. Immune checkpoints refer to a variety of inhibitory pathways of the immune system that are crucial for maintaining self-tolerance and for modulating the duration and amplitude of an immune responses. Tumors use certain immune-checkpoint pathways as a major mechanism of immune resistance, particularly against T cells that are specific for tumor antigens. (see, e.g., Pardoll, 2012 Nature 12:252; Chen and Mellman 2013 Immunity 39:1). The present disclosure provides vectors encoding immune checkpoint inhibitors. Immune checkpoint inhibitors include any agent that blocks or inhibits in a statistically significant manner, the inhibitory pathways of the immune system. Such inhibitors may include antibodies, or antigen binding fragments thereof, that bind to and block or inhibit immune checkpoint receptors or antibodies that bind to and block or inhibit immune checkpoint receptor ligands. Illustrative immune checkpoint molecules that may be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, $\gamma\delta$, and memory $CD8^+$ ($\alpha\beta$) T cells), CD160 (also referred to as BY55) and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160 and CGEN-15049. Illustrative immune checkpoint inhibitors include any of the following antibodies or antigen binding fragments thereof: Tremelimumab (CTLA-4 blocking antibody), anti-OX40, PD-L1 monoclonal Antibody (Anti-B7-H1; MED14736), MK-3475 (pembrolizumab; PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPDL3280A (atezolizumab; anti-PDL1 antibody), MSB0010718C (anti-PDL1 antibody) and Yervoy/ipilimumab (anti-CTLA-4 checkpoint inhibitor).

A sequence encoding a detectable product, usually a protein, can be included to allow for identification of cells that are expressing the desired product. For example, a fluorescent marker protein, such as green fluorescent protein (GFP), is incorporated into the construct along with a sequence of interest (e.g., encoding an antigen). In other cases, the protein may be detectable by an antibody or the protein may be an enzyme that acts on a substrate to yield a detectable product, or a product that allows selection of a transfected or transduced target cell, for example confers drug resistance, such as hygromycin resistance. Typical selection genes encode proteins that confer resistance to antibiotics or other toxins suitable for use in eukaryotic cells, e.g., neomycin, methotrexate, blasticidine, among others known in the art, or complement auxotrophic deficiencies, or supply critical nutrients withheld from the media. The selectable marker can optionally be present on a separate plasmid and introduced by co-transfection.

One or more multicistronic expression units may be utilized that include two or more of the elements (e.g., sequence(s) of interest, the envelope molecule, DC maturation factors) necessary for expression of multiple sequences of interest in a target cell, or for expression of accessory proteins necessary for production of the desired virus in packaging cells. The use of multicistronic vectors reduces the total number of nucleic acid molecules required and thus avoids the possible difficulties associated with coordinating expression from multiple vector genomes. In a multicistronic vector the various elements to be expressed are operably linked to one or more promoters (and other expression control elements as necessary). In some configurations, a multicistronic vector comprises a sequence of interest, a sequence encoding a reporter product, and viral elements. The sequence of interest includes IL-12 and optionally also encodes an antigen and, in certain embodiments can also include an additional immunostimulatory molecule, checkpoint inhibitor, or other cytokine. At times, the multicistronic vector comprises a gene encoding IL-12, an antigen, a gene encoding another immunostimulatory molecule and viral elements.

Each component to be expressed in a multicistronic expression vector may be separated, for example, by an internal ribosome entry site (IRES) element or a viral 2A element, to allow for separate expression of the various proteins from the same promoter. IRES elements and 2A elements are known in the art (U.S. Pat. No. 4,937,190; de Felipe et al. 2004. Traffic 5: 616-626). In one embodiment, oligonucleotides encoding furin cleavage site sequences (RAKR) (Fang et al. 2005. Nat. Biotech 23: 584-590) linked with 2A-like sequences from foot-and-mouth diseases virus (FMDV), equine rhinitis A virus (ERAV), and thosea asigna virus (TaV) (Szymczak et al. 2004. Nat. Biotechnol. 22: 589-594) are used to separate genetic elements in a multicistronic vector. The efficacy of a particular multicistronic vector can readily be tested by detecting expression of each of the genes using standard protocols.

In certain embodiments, where multiple sequences of interest (e.g. IL-12 and one or more antigens of interest, and or one or more additional immunostimulatory molecules, and or a checkpoint inhibitor, etc.) are contemplated for expression in target cells, multiple vectors can be used where each vector expresses one or more of the sequences of interest. In one particular embodiment, one retroviral vector expresses IL-12 and can be used in essence as an adjuvant vector in combination with any one or more other vectors. In this regard, one retroviral vector expresses IL-12 and a separate retroviral vector may express one or more antigens of interest against which an immune response is desired. In another embodiment, one retroviral vector expressing IL-12 can be generated for use with a separate retroviral vector expressing one or more antigens and/or one or more additional immunostimulatory molecules and/or a checkpoint inhibitor. Thus, where multiple sequences of interest are contemplated, they may be provided on the same or on separate vectors.

In a specific exemplification, the viral vector genome comprises: a cytomegalovirus (CMV) enhancer/promoter sequence; the R and U5 sequences from the HIV 5' LTR; a packaging sequence (ψ); the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR. In some exemplifications, the vector genome comprises an intact lentiviral 5' LTR and a self-inactivating 3' LTR. (Iwakuma et al. Virology 15:120, 1999,)

Construction of the vector genome can be accomplished using any suitable genetic engineering techniques known in the art, including, without limitation, the standard techniques of restriction endonuclease digestion, ligation, transformation, plasmid purification, and DNA sequencing, for example as described in Sambrook et al. (1989. Molecular Cloning: A Laboratory Manual. Cold Spring Harbor Laboratory Press, N.Y.), Coffin et al. (Retroviruses. Cold Spring Harbor Laboratory Press, N.Y. (1997)) and "RNA Viruses: A Practical Approach" (Alan J. Cann, Ed., Oxford University Press, (2000).

C. Production of Viral Particles

Any of a variety of methods already known in the art may be used to produce infectious lentiviral particles whose genome comprises an RNA copy of the viral vector genome. In one method, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences of interest. In order to prevent replication of the genome in the target cell, however, endogenous viral genes required for replication will usually be removed and provided separately in the packaging cell line.

In general, the lentiviral vector particles are produced by a cell line that is transfected with one or more plasmid vectors containing the components necessary to generate the particles. These lentiviral vector particles are typically not replication-competent, i.e., they are only capable of a single round of infection. Most often, multiple plasmid vectors are utilized to separate the various genetic components that generate the lentiviral vector particles, mainly to reduce the chance of recombination events that might otherwise generate replication competent viruses. A single plasmid vector having all of the lentiviral components can be used if desired, however. As one example of a system that employs multiple plasmid vectors, a cell line is transfected with at least one plasmid containing the viral vector genome (i.e., the vector genome plasmid), including the LTRs, the cis-acting packaging sequence, and the sequence(s) of interest, which are often operably linked to a heterologous promoter, at least one plasmid encoding the virus enzymatic and structural components (i.e., the packaging plasmid that encodes components such as, Gag and Pol), and at least one envelope plasmid encoding an Arbovirus envelope glycoprotein. Additional plasmids can be used to enhance retrovirus particle production, e.g., Rev-expression plasmids, as described herein and known in the art. Viral particles bud through the cell membrane and comprise a core that includes a genome containing the sequence of interest and an Arbovirus envelope glycoprotein that targets dendritic cells. When the Arbovirus glycoprotein is Sindbis virus E2 glycoprotein, the glycoprotein is engineered to have reduced binding to heparan sulfate compared to the reference strain HR.

Transfection of packaging cells with plasmid vectors of the present invention can be accomplished by well-known methods, and the method to be used is not limited in any way. A number of non-viral delivery systems are known in the art, including for example, electroporation, lipid-based delivery systems including liposomes, delivery of "naked" DNA, and delivery using polycyclodextrin compounds, such as those described in Schatzlein A G. (2001. Non-Viral Vectors in Cancer Gene Therapy: Principles and Progresses. Anticancer Drugs). Cationic lipid or salt treatment methods are typically employed, see, for example, Graham et al. (1973. Virol. 52:456; Wigler et al. (1979. Proc. Natl. Acad. Sci. USA 76:1373-76). The calcium phosphate precipitation method is most often used. However, other methods for introducing the vector into cells may also be used, including nuclear microinjection and bacterial protoplast fusion.

The packaging cell line provides the components, including viral regulatory and structural proteins, that are required in trans for the packaging of the viral genomic RNA into lentiviral vector particles. The packaging cell line may be any cell line that is capable of expressing lentiviral proteins and producing functional lentiviral vector particles. Some suitable packaging cell lines include 293 (ATCC CCL X), 293T, HeLa (ATCC CCL 2), D17 (ATCC CCL 183), MDCK (ATCC CCL 34), BHK (ATCC CCL-10) and Cf2Th (ATCC CRL 1430) cells. The packaging cell line may stably express the necessary viral proteins. Such a packaging cell line is described, for example, in U.S. Pat. No. 6,218,181. Alternatively a packaging cell line may be transiently transfected with nucleic acid molecules encoding one or more necessary viral proteins along with the viral vector genome. The resulting viral particles are collected and used to infect a target cell. The gene(s) encoding envelope glycoprotein(s) is usually cloned into an expression vector, such as pcDNA3 (Invitrogen, CA USA). Eukaryotic cell expression vectors are well known in the art and are available from a number of commercial sources. Packaging cells, such as 293T cells are then co-transfected with the viral vector genome encoding a sequence of interest (e.g., IL-12, optionally one or more antigens, additional cytokines), at least one plasmid encoding virus packing components, and a vector for expression of the targeting molecule. The envelope is expressed on the membrane of the packaging cell and incorporated into the viral vector.

In one scenario, one or more vectors are used to introduce polynucleotide sequences into a packaging cell line for the preparation of a lentiviral vector particle pseudotyped with a Sindbis virus envelope glycoprotein such as E2, as described herein. The vectors can contain polynucleotide sequences encoding the various components of the virus including the Sindbis virus envelope, a sequence(s) of interest (e.g., IL-12 and optionally one or more antigens or other sequences of interest), and any components necessary for the production of the virus that are not provided by the packaging cell.

In yet other scenarios, packaging cells are co-transfected with a viral vector genome encoding IL-12 and one or more additional vectors. For example, in addition to the viral vector encoding IL-12 (and optionally one or more additional sequences of interest), a second vector preferably carries the genes encoding a modified (also called a variant) Sindbis virus envelope. In some situations, the viral vector genome encoding IL-12 also includes a polynucleotide sequence encoding additional selected immunomodulatory molecules, including non-limiting examples of a chemokine, a cytokine, a DC maturation factor, or a factor that regulates immune checkpoint mechanisms. In other situations, the polynucleotide sequence encoding a selected immune modulating factor is contained in a third vector that is co-transfected with the viral vector encoding IL-12 and the one or more additional vectors into the packaging cells.

In some or any embodiments, the lentiviral vector particles described herein comprise a SAMHD1 inhibitor. In certain embodiments, the SAMHD1 inhibitor is a Vpx protein or a Vpr protein. In certain embodiments, the lentiviral vector particles described herein comprise a Vpx protein or a variant thereof (see e.g., WO2013/149167). In some or any embodiments, the variant retains the ability to inhibit SAMHD1.

The Sindbis virus envelope protein contains four N-linked glycans-two on the E2 protein and two on the E1 protein. Two N-glycans of the virus produced in mammalian cells in the absence of a mannosidase I inhibitor have a high-mannose structure (one E2 N-linked glycan and one E1 N-linked glycan), while the remaining two have a complex structure. The two complex structure N-glycans are exposed on the surface of the envelope protein, while the two high-mannose structure N-glycans are buried within the center of the trimer of the envelope proteins. Sindbis virus particles with complex N-linked glycans do not bind DC-SIGN as efficiently as particles with less complex, highly mannosylated glycoproteins.

In certain embodiments, the viral particles are produced in mammalian cells in the presence of the mannosidase I inhibitor, such as kifunensine (see e.g., WO2013/149167). Thus, in some or any embodiments, a virus packaging cell is cultured in the presence of a mannosidase I inhibitor. In some embodiments, the mannosidase I inhibitor is kifunensine. In some embodiments, kifunensine is present in the media at a concentration of about 0.01 µg/ml to about 1 mg/ml, about 0.1 µg/ml to about 10 µg/ml, about 0.1 µg/ml to about 9 µg/ml, about 0.1 µg/ml to about 8 µg/ml, about 0.1 µg/ml to about 7 µg/ml, about 0.1 µg/ml to about 6 µg/ml, about 0.1 µg/ml to about 5 µg/ml, about 0.1 µg/ml to about 4 µg/ml, about 0.1 µg/ml to about 3 µg/ml, about 0.1 µg/ml to about 2 µg/ml, about 0.1 µg/ml to about 1 µg/ml, about 0.25 µg/ml to about 10 µg/ml, about 0.25 µg/ml to about 9 µg/ml, about 0.25 µg/ml to about 8 µg/ml, about 0.25 µg/ml to about 7 µg/ml, about 0.25 µg/ml to about 6 µg/ml, about 0.25 µg/ml to about 5 µg/ml, about 0.25 µg/ml to about 4 µg/ml, about 0.25 µg/ml to about 3 µg/ml, about 0.25 µg/ml to about 2 µg/ml, or about 0.25 µg/ml to about 1 µg/ml.

In some or any embodiments wherein a pseudotyped lentiviral vector particle comprises a Sindbis virus E2 glycoprotein and a Vpx protein, the lentiviral particles are produced in the presence of a mannosidase I inhibitor. In some embodiments, the mannosidase inhibitor is deoxymannojirimycin (DMNJ). In preferred embodiments, the mannosidase inhibitor is kifunensine. In some embodiments, DMNJ is present in the media at a concentration of about 1.0 µg/ml to about 1.0 mg/ml, about 1.0 µg/ml to about 900 µg/ml, about 1.0 µg/ml to about 800 µg/ml, about 1.0 µg/ml to about 700 µg/ml, about 1.0 µg/ml to about 600 µg/ml, about 1.0 µg/ml to about 500 µg/ml, about 1.0 µg/ml to about 400 µg/ml, about 1.0 µg/ml to about 300 µg/ml, about 1.0 µg/ml to about 200 µg/ml, about 1.0 µg/ml to about 100 µg/ml, about 50 µg/ml to about 500 µg/ml, about 50 µg/ml to about 400 µg/ml, about 50 µg/ml to about 300 µg/ml, about 50 µg/ml to about 200 µg/ml, about 50 µg/ml to about 100 µg/ml, about 100 µg/ml to about 500 µg/ml, about 100 µg/ml to about 400 µg/ml, about 100 µg/ml to about 300 µg/ml, about 100 µg/ml to about 200 µg/ml, about 200 µg/ml to about 500 µg/ml, or about 200 µg/ml to about 400 µg/ml.

In some or any embodiments, a pseudotyped lentiviral vector particle produced in the presence of a mannosidase I inhibitor (e.g., kifunensine) comprises an envelope glycoprotein (e.g., Sindbis virus E2), wherein at least 60% of N-linked glycans comprise a Mannose$_5$ (Man$_5$), Man$_6$, Man$_7$, Man$_8$, and/or Man$_9$ structure. In some embodiments, at least 65%, at least 70%, at least 75%, at least 80%, at least 85%, at least 90%, at least 95%, at least 96%, at least 97%, at least 98%, at least 99%, or 100% of N-linked glycans comprise a Man$_5$, Man$_6$, Man$_7$, Man$_8$, and/or Man$_{9+}$ structure.

In one scenario, one or more vectors are used to introduce polynucleotide sequences into a packaging cell line for the preparation of a lentiviral vector particle pseudotyped with a Sindbis virus envelope glycoprotein such as E2, as described herein. In some embodiments, the lentiviral vector particle is highly mannosylated. In some embodiments, the lentiviral vector particle also comprises a Vpx protein or variant thereof. In yet other embodiments, the lentiviral vector particle is highly mannosylated and comprises a Vpx protein or variant thereof. The vectors can contain polynucleotide sequences encoding the various components of the virus including the Sindbis virus envelope, a sequence(s) of interest (typically encoding an antigen), and any components necessary for the production of the virus that are not provided by the packaging cell.

The glycosylation profile of a viral envelope protein can be determined by any method known in the art. For example, gel shift assays on viral glycoproteins treated with glycosidases (e.g., EndoH or PNGaseF) or left untreated may be compared. Other methods include cleaving glycans from the viral glycoproteins and separating and identifying the components via HPLC and mass spectrometry methods.

Production of virus is measured as described herein and expressed as IU per volume. IU is infectious unit, or alternatively transduction units (TU); IU and TU can be used interchangeably as a quantitative measure of the titer of a viral vector particle preparation. As described herein, virus is produced in which the genome can express a product that is readily measurable. A fluorescent protein, green fluorescent protein, is preferred. The lentiviral vector is typically non-integrating. The virus is then administered to target cells and the number of target cells that express GFP is determined, such as by flow cytometry. The titer is then calculated. The titer is preferably as high as possible, but at least $1 \times 10^5$ IU/mL, at least $3 \times 10^5$ IU/mL, at least $1 \times 10^6$ IU/mL, at least $3 \times 10^6$ IU/mL, or at least $1 \times 10^7$ U/mL of cell supernatant (before any concentration). Alternatively, the titer is at least 80%, at least 90%, at least 95%, at least 100% of the titer of the same lentiviral vector pseudotyped in the same cells with VSV-G envelope.

D. Delivery of the Virus

The virus may be delivered to a target cell in any way that allows the virus to contact the target dendritic cells (DCs) in which delivery of a polynucleotide encoding IL-12 and any other polynucleotide of interest is desired. At times, a suitable amount of virus will be introduced into a human or other animal directly (in vivo), e.g., though injection into the body. Suitable animals include, without limitation, horses, dogs, cats, cattle, pigs, sheep, rabbits, chickens or other birds. Viral particles and other therapeutic agents disclosed herein may be injected by a number of routes, such as intravenous, intra-dermal, subcutaneous, intranodal, intraperitoneal cavity, or mucosal. The virus may be delivered using a subdermal injection device such the devices disclosed in U.S. Pat. Nos. 7,241,275, 7,115,108, 7,108,679, 7,083,599, 7,083,592, 7,047,070, 6,971,999, 6,808,506, 6,780,171, 6,776,776, 6,689,118, 6,670,349, 6,569,143, 6,494,865, 5,997,501, 5,848,991, 5,328,483, 5,279,552, 4,886,499. In one particular embodiment, the virus is delivered intratumorally. Other injection locations also are suitable, such as directly into organs comprising target cells. For example, intra-lymph node injection, intra-spleen injection, or intra-bone marrow injection may be used to deliver virus to the lymph node, the spleen and the bone marrow, respectively. Depending on the particular circumstances and nature of the target cells, introduction can be carried out through other means including for example, inhalation, or direct contact with epithelial tissues, for example those in the eye, mouth or skin.

As noted elsewhere herein, in certain embodiments where multiple sequences of interest are contemplated for expression in target cells, the sequences of interest may be expressed from the same vector or may be provided on separate vectors. In this regard administration of multiple vectors is contemplated. In certain embodiments, each vector is administered by the same route. In other embodiments each vector may be administered by a different route and at a different time. In one embodiment each vector is administered by the same route but at a different dose and at a different time. In a further embodiment each vector is administered by the same route and at the same time, at the same or different sites, and at the same dose or at different doses. In another embodiment each vector is administered by the same route and at the same time but each vector is given at a different dose.

As one example, a vector expressing IL-12 may be administered intratumorally concurrently with a separate vector expressing an antigen of interest. In an additional example, a vector expressing IL-12 may be administered intratumorally concurrently with a separate vector expressing one or more antigens of interest and optionally one or more additional sequences of interest. In a further embodiment, a vector expressing IL-12 and one or more antigens of interest is administered intratumorally. In an additional embodiment, a vector expressing IL-12 is administered intratumorally and a separate vector expressing one or more antigens of interest is administered concurrently at a separate site, either intratumorally at a different tumor, or at a different site and via different route (e.g. subcutaneously, intradermally or intramuscularly). In other embodiments, a vector expressing IL-12 can be administered intratumorally and a separate vector expressing one or more antigens of interest may be administered either before or after the vector expressing IL-12, either at the same site or at a different site. In this regard, the two vectors may be administered at different sites and using different doses. In certain embodiments where a vector expressing IL-12 and a separate vector expressing one or more antigens and/or comprising other sequences of interest are administered concurrently, it may be advantageous to mix the compositions comprising the separate vectors into a single administration dose.

Alternatively, target cells are provided and contacted with the virus in vitro, such as in culture plates. The target cells are typically populations of cells comprising dendritic cells obtained from a healthy subject or a subject in need of treatment or in whom it is desired to stimulate an immune response to an antigen. Methods to obtain cells from a subject are well known in the art and includes phlebotomy, surgical excision, and biopsy. Human DCs may also be generated by obtaining CD34α+ human hematopoietic progenitors and using an in vitro culture method as described elsewhere (e.g., Banchereau et al. Cell 106, 271-274 (2001)).

The virus may be suspended in media and added to the wells of a culture plate, tube or other container. Media containing the virus may be added prior to the plating of the cells or after the cells have been plated. Cells are typically incubated in an appropriate amount of media to provide viability and to allow for suitable concentrations of virus in the media such that transduction of the host cell occurs. The cells are preferably incubated with the virus for a sufficient amount of time to allow the virus to infect the cells. Preferably the cells are incubated with virus for at least 1 hour, at least 5 hours or at least 10 hours.

In both in vivo and in vitro delivery, an aliquot of viral particles containing sufficient number to infect the desired target cells may be used. When the target cell is to be cultured, the concentration of the viral particles is generally at least 1 IU/μL, more preferably at least 10 IU/μl, even more preferably at least 300 IU/μL, even more preferably at least $1 \times 10^4$ IU/μL, even more preferably at least $1 \times 10^5$ IU/μL, even more preferably at least $1 \times 10^6$ IU/μL, or even more preferably at least $1 \times 10^7$ IU/μL Following infection with the virus in vitro, target cells can be introduced (or re-introduced) into a human or other animal. The cells can be introduced into the dermis, under the dermis, or into the peripheral blood stream. The cells introduced into an animal are preferably cells derived from that animal, to avoid an adverse immune response. Cells derived from a donor having a similar immune background may also be used. Other cells that also can be used include those designed to avoid an adverse immunologic response.

Target cells may be analyzed for integration, transcription and/or expression of the sequence or gene(s) of interest, the number of copies of the gene integrated, and the location of the integration, for examples. Such analysis may be carried out at any time and may be carried out by any method known in the art.

Subjects in which a virus or virus-infected dendritic cells are administered can be analyzed for location of infected cells, expression of the virus-delivered polynucleotide or gene of interest, stimulation of an immune response, and monitored for symptoms associated with a disease or disorder by any methods known in the art.

The methods of infecting cells disclosed above do not depend upon individual-specific characteristics of the cells. As a result, they are readily extended to a variety of animal species. In some instances, viral particles are delivered to a human or to human dendritic cells, and in other instances they are delivered to an animal such as a mouse, horse, dog, cat, or mouse or to birds. As discussed herein, the viral vector genome is pseudotyped to confer upon it a broad host range as well as target cell specificity. One of skill in the art would also be aware of appropriate internal promoters and other elements to achieve the desired expression of a sequence of interest in a particular animal species. Thus, one of skill in the art will be able to modify the method of infecting dendritic cells from any species.

E. Therapeutic and Prophylactic Administrations

Target cells may be infected with a lentivirus vector particle as described herein for the prevention of or treatment of a disease or disorder, particularly those for which induction of an immune response influenced by IL-12 in a patient would be beneficial. In particular embodiments, dendritic cells may be infected with a lentivirus vector particle as described herein for the prevention of or treatment of a disease or disorder, particularly those for which activation of an immune response in a patient would be beneficial. Many such diseases are well known. For example, diseases or disorders that are amenable to treatment or prevention by the methods of the present invention include, without limitation, cancers, autoimmune diseases, and infections, including viral, bacterial, fungal and parasitic infections. In one method, a disease is treated by viral particles described herein in order to deliver a sequence of interest to dendritic cells, wherein expression of the sequence of interest produces IL-12 and optionally a disease-specific antigen and leads to stimulation of cellular immune responses and humoral immune responses. In certain embodiments, the IL-12 is expressed in conjunction with a sequence of interest encoding one or more antigen against which an immune response is desired, but which is not normally expressed in a dendritic cell. The antigen(s) is expressed and presented by the dendritic cell. The viral vector genome may further encode an additional immunostimulatory molecule or other immunomodulatory molecules such as a checkpoint inhibitor.

In a typical usage, viral particles deliver to target cells sequences encoding IL-12 and, in certain embodiments, IL-12 in combination with one or more antigens, either expressed by the same vector or by a separate vector. The delivery can be achieved by contacting dendritic cells with the virus in vitro, whereupon the infected dendritic cells are provided to a patient. Other times, delivery can be achieved by delivering the virus to a subject for infecting dendritic cells in vivo. The dendritic cells then produce IL-12 thereby triggering cellular responses to IL-12 including induction of CD8 T cells, an increase in B cells and CD4 T cells and induction of a TH1 response, among other biological activities induced by IL-12. In certain embodiments, a DC targeting lentiviral vector expressing IL-12 is administered intratumorally and thereby triggers induction of a Th1 response, among other biological activities, and provides therapeutic anti-tumor activity. In certain embodiments, intratumoral administration of a DC targeting lentiviral vector expressing IL-12 in conjunction with a vector expressing one or more antigens also stimulates antigen-specific T cells or B cells, in a patient to induce cellular and humoral immune responses to the expressed antigen. In such ways, a patient that is suffering from a disease or disorder is treated by generating immune cells with a desired specificity.

In certain embodiments, a vector expressing IL-12 may be administered intratumorally. The present disclosure shows unexpectedly that intratumoral injection of lentiviral vector expressing low levels of IL-12 was therapeutically effective in multiple models tested. In particular, the experiments showed that even a single intratumoral injection of DC targeting lentiviral vector expressing low levels of IL-12 as described herein was therapeutically effective. Other studies in the art require multiple injections of IL-12 with electroporation and require higher levels of IL-12. For example, in one study, intratumoral injections of IL-12 plasmid with electroporation are carried out with 3 injections at days 1, 5 and 8 and possibly a second course of treatment at week 7 (see, e.g., clinical trial NCT01440816). In another study, subjects may receive up to six cycles of treatment consisting of two treatment days, Days 1 and 8, in a 28-day cycle. In these studies, patients receive intra-tumoral injection of pIL-12 followed immediately by electrical discharge around the tumor site resulting in electroporation of plasmid DNA into tumor cells (see e.g., NCT01579318).

The present invention unexpectedly shows that very low levels of IL-12 expression locally in the tumor resulting from injection of the lentiviral vectors described herein was therapeutically effective. In this regard, the level of IL-12 expression was less than about 0.5 micrograms produced/1E10 vector genomes during the first 48 hours, based on in vitro studies under optimal culture conditions. IL-12 levels can be measured using an in vitro transduction assay as described in Example 1 and Example 6. For example, on day 0, 1E6 of an appropriate target cell (such as 293-DC-SIGN cells where the lentiviral vector particles are pseudotyped with a modified Sindbis E2 glycoprotein), are plated into 6 well plates in 2 mL of appropriate culture media. On day 1, the cells are transduced with 8.5E9 vector genomes. The transduction is generally carried out in 600 µL of media then 0.9 mL of media is added 6 hours later. On day 3 (48 hours post transduction), the supernatants are filtered through a 0.45 µm filter and IL-12 is measured using a standard ELISA (e.g., using a commercially available kit, such as R&D kit M1270).

Thus, in one particular embodiment of the present invention, the viral vectors described herein expressing IL-12 are administered intratumorally, and in certain embodiments administered intratumorally in a single injection, for the treatment of a cancer. In certain embodiments, the intratumoral injection of the lentiviral vectors described herein expressing IL-12 produce a low-level of IL-12. In certain embodiments, a single intratumoral injection of the lentiviral vectors described herein expressing IL-12 is used and produces a low-level of IL-12. The level of IL-12 produced by the intratumoral injection, in certain embodiments a single injection, of the lentiviral vectors described herein generally range from the equivalent of about 0.05 micrograms produced during the first 48 hours to about 5 micrograms produced during the first 48 hours, as measured by the in vitro assay described above. In certain embodiments, the level of IL-12 produced by the single intratumoral injection of the lentiviral vectors described herein ranges from the equivalent of about 0.1 micrograms produced during the first 48 hours to about 1 microgram produced during the first 48 hours. In certain embodiments, the level of IL-12 produced by the single intratumoral injection of the lentiviral vector range from about 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or about 5.0 µg IL-12 produced during the first 48 hours as measured by the in vitro assay described above. The amount of IL-12 produced by a particular dose of lentiviral vector described herein can be measured using in vitro studies under optimal culture conditions.

In a specific embodiment, a DC targeting lentiviral vector expressing IL-12 used for single intratumoral injection is an integrating vector. In another embodiment, the DC targeting lentiviral vector expressing IL-12 used for single intratumoral injection is a non-integrating vector.

In one embodiment, a DC targeting lentiviral vector expressing IL-12 is administered intratumorally in conjunction with a regulatory T cell depleting agent, such as cyclophosphamide, anti-CTLA4 or an antibody that specifically binds to a regulatory T cell marker (e.g., an anti-CD25 antibody; such antibodies include daclizumab). In this regard, such regulatory T cell depletion agents may be administered before, concurrently with, or after intratumoral administration of the LV-IL12 as described herein. In a certain embodiment, the DC targeting lentiviral vector expressing IL-12 is administered intratumorally concurrently with systemic administration of an agent that depletes regulatory T cells, such as cyclophosphamide, anti-CTLA4 or a regulatory T cell depleting antibody or agent. In certain embodiments, low dose cyclophosphamide is administered using a metronomic regimen. In certain embodiments, the cyclophosphamide is administered orally.

Various methods exist or are being evaluated for depleting regulatory T cells in humans and the LV/IL12 vectors and methods described herein can be used with any of these methods. As would be appreciated by a person of skill in the art, one such method is depletion of CD44+CD137+ regulatory T cells (see e.g., Immunotherapy. 2012 May; 4(5): 483-485).

In another embodiment, the viral vectors herein expressing IL-12 are administered concurrently with a second vector expressing an antigen of interest. In an additional example, a vector expressing IL-12 may be administered intratumorally concurrently with a separate vector expressing one or more antigens of interest and optionally one or more additional sequences of interest. In a further embodiment, a vector expressing IL-12 and one or more antigens of interest is administered intratumorally. In an additional embodiment, a vector expressing IL-12 is administered intratumorally and a separate vector expressing one or more antigens of interest is administered concurrently at a separate site, either intratumorally at a different tumor, or at a different site and via different route (e.g. subcutaneously, intradermally or intramuscularly). In other embodiments, a vector expressing IL-12 can be administered intratumorally and a separate vector expressing one or more antigens of interest may be administered either before or after the vector expressing IL-12, either at the same site or at a different site. In this regard, the two vectors may be administered at different sites and using different doses. In certain embodiments where a vector expressing IL-12 and a separate vector expressing one or more antigens and/or comprising other sequences of interest are administered concurrently, it may be advantageous to mix the compositions comprising the separate vectors into a single administration dose.

Following viral infection, the sequence of interest (e.g., encoding IL-12 and optionally encoding one or more antigens) is expressed by the target dendritic cells. If contacted ex vivo, the target dendritic cells are then transferred back to the patient, for example by injection, where they interact with immune cells that are capable of generating an immune response against the desired antigen. In preferred embodiments, the recombinant virus is injected into the patient where it transduces the targeted dendritic cells in situ. The dendritic cells then express IL-12 and optionally the particular antigen associated with a disease or disorder to be treated, and the patient is able to mount an effective immune response against the disease or disorder.

The viral vector genome may contain a polynucleotide sequence encoding more than one antigen, and upon transduction of a target dendritic cell, generates immune responses to the multitude of antigens delivered to the cell. In some embodiments, the antigens are related to a single disease or disorder. In other embodiments, the antigens are related to multiple diseases or disorders.

In some of the viruses, DC maturation factors that activate and/or stimulate maturation of the DCs are delivered in conjunction with the sequence of interest. In alternatives, the DCs are activated by delivery of DC maturation factors prior to, simultaneously with, or after delivery of the virus. DC maturation factors may be provided separately from administration of the virus.

As described herein, one or more immunomodulatory molecules and/or DC maturation factors can be encoded by one or more sequences that are contained in the viral genome and expressed after the virus infects a dendritic cell. The sequences encoding immunomodulatory molecules can also be provided in a separate vector that is co-transfected with the viral vector encoding IL-12 and optionally one or more antigens in a packaging cell line.

The methods described herein can be used for adoptive immunotherapy in a patient. A polynucleotide encoding IL-12 and in certain embodiments a desired antigen is obtained and packaged into a recombinant virus. Target dendritic cells are obtained from the patient and transduced with a recombinant virus containing a polynucleotide that encodes IL-12 and optionally the desired antigen. The dendritic cells are then transferred back into the patient.

The viral particles may be injected in vivo, where they infect DCs and deliver IL-12 and optionally a sequence encoding an antigen or other immunostimulatory molecules. The amount of viral particles is at least $3\times10^6$ IU, and can be at least $1\times10^7$ IU, at least $3\times10^7$ IU, at least $1\times10^8$ IU, at least $3\times10^8$ IU, at least $1\times10^9$ IU, or at least $3\times10^9$ IU. At selected intervals, DCs from the recipient's lymphoid organs may be used to measure expression, for example, by observing marker expression, such as GFP or luciferase. Nucleic acid monitoring techniques and measurements of reverse transcriptase (RT) activity can also be used to analyze the biodistribution of viral particles. T cells from peripheral blood mononuclear cells, lymph nodes, spleens, or malignant or target pathogen-infected tissue of lentiviral vector particle-treated recipients may be measured from the magnitude and durability of response to antigen stimulation. Tissue cells other than DCs, such as epithelial cells and lymphoid cells, may be analyzed for the specificity of in vivo gene delivery.

Vaccines often include an adjuvant. In certain embodiments, the lentiviral vectors expressing IL-12 may be used as an adjuvant in conjunction with other vaccines.

The lentiviral vector particles described herein may also be administered along with an adjuvant. The adjuvant may be administered with the recombinant virus particles, before the recombinant virus particles, or after the recombinant virus particles. If administered with the virus particles, desirable adjuvants do not significantly disrupt the integrity of the virus particle, such as disrupting the viral membrane containing the envelope glycoproteins.

A variety of adjuvants can be used in combination with the virus to further increase the elicited immune response. Certain illustrative adjuvants include alum, 3 De-O-acylated monophosphoryl lipid A (MPL) (see GB 2220211). QS21 is a triterpene glycoside or saponin isolated from the bark of the *Quillaja saponaria molina* tree found in South America (see Kensil et al., in Vaccine Design: The Subunit and Adjuvant Approach (eds. Powell and Newman, Plenum Press, N Y, 1995); U.S. Pat. No. 5,057,540). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Alternatively, Aβ can be coupled to an adjuvant. For example, a lipopeptide version of Aβ can be prepared by coupling palmitic acid or other lipids directly to the N-terminus of Aβ as described for hepatitis B antigen vaccination (Livingston, J. Immunol. 159, 1383-1392 (1997)). However, such coupling should not substantially change the conformation of Aβ so as to affect the nature of the immune response thereto. Adjuvants can be administered as a component of a therapeutic composition with an active agent or can be administered separately, before, concurrently with, or after administration of the therapeutic agent.

One class of adjuvants is aluminum salts (alum), such as aluminum hydroxide, aluminum phosphate, aluminum sulfate. Such adjuvants can be used with or without other specific immunostimulating agents such as MPL or 3-DMP, QS21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80, 5% pluronic-blocked polymer L121, and thr-MDP, either microfluidized into a submicron emulsion or vortexed to generate a larger particle size emulsion, and (c) Ribi adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™). Another class of preferred adjuvants is saponin adjuvants, such as Stimulon™ (QS21, Aquila, Worcester, Mass.) or particles generated there from such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

Another adjuvant that can be used with the compositions herein is identified by chemical formula (I):

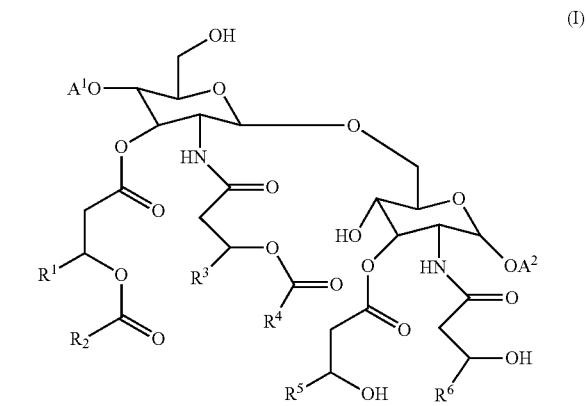

wherein the moieties A1 and A2 are independently selected from the group of hydrogen, phosphate, and phosphate salts. Sodium and potassium are exemplary counterions for the phosphate salts. The moieties $R^1$, $R^2$, $R^3$, $R^4$, $R^5$, and $R^6$ are independently selected from the group of hydrocarbyl having 3 to 23 carbons, represented by $C_3$-$C_{23}$. For added clarity it will be explained that when a moiety is "independently selected from" a specified group having multiple members, it should be understood that the member chosen for the first moiety does not in any way impact or limit the choice of the member selected for the second moiety. The carbon atoms to which $R^1$, $R^3$, $R^5$ and $R^6$ are joined are asymmetric, and thus may exist in either the R or S stereochemistry. In one embodiment all of those carbon atoms are in the R stereochemistry, while in another embodiment all of those carbon atoms are in the S stereochemistry.

"Hydrocarbyl" refers to a chemical moiety formed entirely from hydrogen and carbon, where the arrangement of the carbon atoms may be straight chain or branched, noncyclic or cyclic, and the bonding between adjacent carbon atoms maybe entirely single bonds, i.e., to provide a saturated hydrocarbyl, or there may be double or triple bonds present between any two adjacent carbon atoms, i.e., to provide an unsaturated hydrocarbyl, and the number of carbon atoms in the hydrocarbyl group is between 3 and 24 carbon atoms. The hydrocarbyl may be an alkyl, where representative straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while branched alkyls include isopropyl, sec-butyl, isobutyl, tert-butyl, isopentyl, and the like. Representative saturated cyclic hydrocarbyls include cyclopropyl, cyclobutyl, cyclopentyl, cyclohexyl, and the like; while unsaturated cyclic hydrocarbyls include cyclopentenyl and cyclohexenyl, and the like. Unsaturated hydrocarbyls contain at least one double or triple bond between adjacent carbon atoms (referred to as an "alkenyl" or "alkynyl", respectively, if the hydrocarbyl is non-cyclic, and cycloalkeny and cycloalkynyl, respectively, if the hydrocarbyl is at least partially cyclic). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The adjuvant of formula (I) may be obtained by synthetic methods known in the art, for example, the synthetic methodology disclosed in PCT International Publication No. WO 2009/035528, as well as the publications identified in WO 2009/035528. Certain of the adjuvants may also be obtained commercially. A preferred adjuvant is Product No. 699800 as identified in the catalog of Avanti Polar Lipids, Alabaster Ala., see E1 in combination with E10, below.

In various embodiments of the invention, the adjuvant has the chemical structure of formula (I) but the moieties A1, A2, R1, R2, R3, R4, R5, and R6 are selected from subsets of the options previously provided for these moieties, where these subsets are identified below by E1, E2, etc.

E1: $A_1$ is phosphate or phosphate salt and $A_2$ is hydrogen.
E2: $R^1$, $R^3$, $R^5$ and $R^6$ are $C_3$-$C_{21}$ alkyl; and $R^2$ and $R^4$ are $C_5$-$C_{23}$ hydrocarbyl.
E3: $R^1$, $R^3$, $R^5$ and $R^6$ are $C_5$-$C_{17}$ alkyl; and $R^2$ and $R^4$ are $C_7$-$C_{19}$ hydrocarbyl.
E4: $R^1$, $R^3$, $R^5$ and $R^6$ are $C_7$-$C_{15}$ alkyl; and $R^2$ and $R^4$ are $C_9$-$C_{17}$ hydrocarbyl.
E5: $R^1$, $R^3$, $R^5$ and $R^6$ are $C_9$-$C_{13}$ alkyl; and $R^2$ and $R^4$ are $C_{11}$-$C_{15}$ hydrocarbyl.
E6: $R^1$, $R^3$, $R^5$ and $R^6$ are $C_9$-$C_{15}$ alkyl; and $R^2$ and $R^4$ are $C_{11}$-$C_{17}$ hydrocarbyl.
E7: $R^1$, $R^3$, $R^5$ and $R^6$ are $C_7$-$C_{13}$ alkyl; and $R^2$ and $R^4$ are $C_9$-$C_{15}$ hydrocarbyl.
E8: $R^1$, $R^3$, $R^5$ and $R^6$ are $C_1$-$C_{20}$ alkyl; and $R^2$ and $R^4$ are $C_{12}$-$C_{20}$ hydrocarbyl.
E9: $R^1$, $R^3$, $R^5$ and $R^6$ are $C_{11}$ alkyl; and $R^2$ and $R^4$ are $C_{13}$ hydrocarbyl.
E10: $R^1$, $R^3$, $R^5$ and $R^6$ are undecyl and $R^2$ and $R^4$ are tridecyl.

In certain options, each of E2 through E10 is combined with embodiment E1, and/or the hydrocarbyl groups of E2 through E9 are alkyl groups, preferably straight chain alkyl groups.

The adjuvant of formula (I) may be formulated into a pharmaceutical composition, optionally with a co-adjuvant, each as discussed below. In this regard reference is made to US Patent Publication No. 2008/0131466 which provides formulations, e.g., aqueous formulation (AF) and stable emulsion formulations (SE) for GLA adjuvant, where these formulations may be utilized for any of the adjuvants of formula (I).

An adjuvant can be administered with the virus of the invention as a single composition, or can be administered before, concurrent with or after administration of the recombinant virus of the invention. In certain embodiments, an immunogen is included with the adjuvant. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS21 are preferred. Optionally, two or more different adjuvants can be used simultaneously, such as alum with MPL, alum with QS21, MPL with QS21, and alum, QS21 and MPL together. Also, Incomplete Freund's adjuvant can be used (Chang et al., Advanced Drug Delivery Reviews 32, 173-186 (1998)), optionally in combination with any of alum, QS21, and MPL and all combinations thereof.

The compositions comprising the retroviral vectors as described herein may also be administered simultaneously with, prior to, or after administration of one or more other therapeutic agents.

Such combination therapy may include administration of a single pharmaceutical dosage formulation which contains a viral vector as described herein and one or more additional active agents, as well as administration of compositions comprising a viral vector of the invention and each active agent in its own separate pharmaceutical dosage formulation. For example, a composition comprising a viral vector and the other active agent can be administered to the patient together in a single enteral (e.g., oral) dosage composition such as a tablet or capsule, or each agent administered in separate enteral (e.g., oral) dosage formulations. Similarly, compositions comprising a viral vector and the other active agent can be administered to the patient together in a single parenteral (e.g., any of the parenteral routes known and described herein, such as, subcutaneous, intradermal, intranodal, intratumoral or intramuscular) dosage composition such as in a saline solution or other physiologically acceptable solution, or each agent administered in separate parenteral dosage formulations. The combination therapies as described herein can be administered by the same route or may be administered using different routes. Where separate dosage formulations are used, the compositions comprising viral vector and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of compositions comprising a viral vector of this disclosure in combination with one or more other therapeutic agents (e.g. other anti-cancer agents, or other palliative or adjunctive therapy). In certain embodiments, such therapeutic agents may be accepted in the art as a standard treatment for a particular cancer as described herein. Exemplary therapeutic agents contemplated include cytokines, growth factors, steroids, NSAIDs, DMARDs, anti-inflammatories, immune checkpoint inhibitors, chemotherapeutics, radiotherapeutics, or other active and ancillary agents.

In one embodiment, compositions comprising a viral vector of the present invention are administered in combination with one or more cancer therapeutic agents, including one or more chemotherapeutic agents. Examples of cancer therapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; trastuzumab, docetaxel, platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such asTargretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Further cancer therapeutic agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors.

In another embodiment, the viral vector compositions herein are administered in combination with another immunostimulatory agent. Such immunostimulatory agents include, but are not limited to, N-acetylmuramyl-L-alanine-D-isoglutamine (MDP), glucan, IL-12, GM-CSF, interferon-γ and anti-CD40 antibodies or other antibodies that bind to and activate co-stimulatory pathways (e.g., CD28, ICOS, OX40, CD27 and the like).

In one embodiment, the viral vector compositions herein are administered in combination with one or more immune checkpoint inhibitors. Immune checkpoints refer to a variety of inhibitory pathways of the immune system that are crucial for maintaining self-tolerance and for modulating the duration and amplitude of an immune responses. Tumors use certain immune-checkpoint pathways as a major mechanism of immune resistance, particularly against T cells that are specific for tumor antigens. (see, e.g., Pardoll, 2012 Nature 12:252; Chen and Mellman 2013 Immunity 39:1). The present disclosure provides immune checkpoint inhibitors that can be administered in combination with the GLA compositions without antigen. Such combination therapies work in concert to enhance an anti-cancer immune response. Certain viruses have also developed mechanisms to co-opt immune checkpoint pathways. Therefore, in certain embodiments, such combination therapy may be used to enhance an anti-viral immune response.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative immune checkpoint molecules that may be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory CD8+ (αβ) T cells), CD160 (also referred to as BY55) and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-B7-H1; MED14736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor).

In a further embodiment, the viral vector compositions herein are administered in combination with other TLR4 agonists, or a TLR8 agonist, or a TLR9 agonist. Such an agonist may be selected from peptidoglycan, polyI:C, CpG, 3M003, flagellin, and *Leishmania* homolog of eukaryotic ribosomal elongation and initiation factor 4a (LeIF).

In an additional embodiment, the viral vector compositions herein are administered in combination with a cytokine. By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1 through IL-36, including, but not limited to, IL-1, IL-1alpha, IL-2, IL-3, IL-4, IL-5, IL-6, IL-7, IL-8, IL-9, IL-10, IL-11, IL-12; IL-15, IL-18, IL-21, IL-23, IL-27, TNF; and other polypeptide factors including LIF and kit ligand (KL). As used herein, the term cytokine includes proteins from natural sources or from recombinant cell culture, and biologically active equivalents of the native sequence cytokines.

In certain embodiments, the compositions comprising viral vectors as described herein may be administered in combination with chloroquine, a lysosomotropic agent that prevents endosomal acidification and which inhibits autophagy induced by tumor cells to survive accelerated cell growth and nutrient deprivation. More generally, the compositions comprising viral vectors as described herein may be administered in combination with therapeutic agents that act as autophagy inhibitors, radiosensitizers or chemosensitizers, such as chloroquine, misonidazole, metronidazole, and hypoxic cytotoxins, such as tirapazamine. In this regard, such combinations of a viral vector with chloroquine or other radio or chemo sensitizer, or autophagy inhibitor, can be used in further combination with other cancer therapeutic agents or with radiation therapy.

In another embodiment, the compositions comprising viral vectors as described herein may be administered in combination with small molecule drugs which are known to result in killing of tumor cells with concomitant activation of immune responses, termed "immunogenic cell death", such as cyclophosphamide, doxorubicin, oxaliplatin and mitoxantrone. Furthermore, combinations with drugs known to enhance the immunogenicity of tumor cells such as patupilone (epothilone B), epidermal-growth factor receptor (EGFR)-targeting monoclonal antibody 7A7.27, histone deacetylase inhibitors (e.g., vorinostat, romidepsin, panobinostat, belinostat, and entinostat), the n3-polyunsaturated fatty acid docosahexaenoic acid, furthermore proteasome inhibitors (e.g. bortezomib), shikonin (the major constituent of the root of Lithospermum erythrorhizon) and oncolytic viruses, such as TVec (talimogene laherparepvec). In other embodiments, the compositions comprising viral vectors as described herein may be administered in combination with epigenetic therapies, such as DNA methyltransferase inhibitors (e.g. Decitabine, 5-aza-2'-deoxycytidine) which may be administered locally or systemically.

In another embodiment, the compositions comprising a viral vector as described herein may be administered in combination with one or more antibodies that increase ADCC uptake of tumor by DCs. Thus, the present invention contemplates combining compositions comprising a viral vector with any molecule that induces or enhances the ingestion of a tumor cell or its fragments by an antigen presenting cell and subsequent presentation of tumor antigens to the immune system. These molecules include agents that induce receptor binding (such as Fc or mannose receptors) and transport into the antigen presenting cell such as antibodies, antibody-like molecules, multi-specific multivalent molecules and polymers. Such molecules may either be administered intratumorally with the composition comprising viral vector, or administered by a different route. For example, a composition comprising viral vector as described herein may be administered intratumorally in conjunction with intratumoral injection of rituximab, cetuximab, trastuzumab, Campath, panitumumab, ofatumumab, brentuximab, pertuzumab, Ado-trastuzumab emtansine, Obinutuzumab, anti-HER1, -HER2, or -HER3 antibodies (e.g., MEHD7945A; MM-111; MM-151; MM-121; AMG888), anti-EGFR antibodies (e.g. Nimotuzumab, ABT-806), or other like antibodies. Any multivalent scaffold that is capable of engaging Fc receptors and other receptors that can induce internalization may be used in the combination therapies described herein—e.g. peptides and/or proteins capable of binding targets that are linked to Fc fragments or polymers capable of engaging receptors.

In certain embodiments, the combination of viral vector with such antibodies may be further combined with an antibody that promotes a co-stimulatory signal (e.g., by blocking inhibitory pathways), such as anti-CTLA-4, or that activates co-stimulatory pathways such as an anti-CD40, anti-CD28, anti-ICOS, anti-OX40, anti-CD27 antibodies and the like.

The compositions comprising viral vector may be administered alone or in combination with other known cancer treatments, such as radiation therapy, immune checkpoint inhibitors, chemotherapy or other cancer therapeutic agents, transplantation, immunotherapy, hormone therapy, photodynamic therapy, etc. The compositions may also be administered in combination with antibiotics.

The present disclosure provides for methods of treating cancer by administering the DC targeting lentiviral vectors expressing IL12, optionally in combination with other lentiviral vectors expressing antigen, or in combination with other therapeutic agents. Examples of specific cancers include, but are not limited to, lung cancer, colon cancer, breast cancer, testicular cancer, stomach cancer, pancreatic cancer, ovarian cancer, liver cancer, bladder cancer, colorectal cancer, and prostate cancer. Additional cancers are well known to those of skill in the art and include, but are not limited to: leukemia, lymphoma, cervical cancer, glioma tumors, adenocarcinomas, sarcomas, soft tissue sarcomas and skin cancer. Exemplary cancers include, but are not limited to, a bladder tumor, breast tumor, prostate tumor, basal cell carcinoma, biliary tract cancer, bladder cancer, bone cancer, brain and CNS cancer (e.g., glioma tumor), cervical cancer, choriocarcinoma, colon and rectum cancer, connective tissue cancer, cancer of the digestive system; endometrial cancer, esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma, neuroblastoma, oral cavity cancer (e.g., lip, tongue, mouth, and pharynx); ovarian cancer; pancreatic cancer, retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas. Cancer also includes neoplasias and malignant disorders in mammals that are well known in the art. In one embodiment, the present disclosure provides methods of treating cancer by intratumoral injection of the DC targeting lentiviral vectors expressing IL12, and in some embodiments with a single intratumoral injection. Any cancer with an injectable tumor is contemplated herein for intratumoral injection with the DC targeting IL12 expressing lentiviral vectors.

F. Pharmaceutical Compositions and Kits

Also contemplated herein are pharmaceutical compositions and kits containing a virus provided herein and one or more components. Pharmaceutical compositions can include viral vector particles as provided herein and a pharmaceutical carrier. Kits can include the pharmaceutical compositions and/or combinations provided herein, and one or more components, such as instructions for use, a device for administering a compound to a subject, and a device for administering a compound to a subject.

Provided herein are pharmaceutical compositions containing viral particles as provided herein and a suitable pharmaceutical carrier. Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body.

The viral vector particles provided herein can be packaged as kits. Kits can optionally include one or more components such as instructions for use, devices, and additional reagents, and components, such as tubes, containers and syringes for practice of the methods. Exemplary kits can include the viruses provided herein, and can optionally include instructions for use, a device for detecting a virus in a subject, a device for administering the virus to a subject, and a device for administering a compound to a subject.

Kits comprising polynucleotides encoding a gene of interest (typically an antigen) are also contemplated herein. The kit may include at least one plasmid encoding virus packaging components and vector encoding Sindbis virus E2 glycoprotein variant. Some kits will contain at least one plasmid encoding virus packaging components, a vector encoding Sindbis virus E2 glycoprotein variant, and a vector encoding at least one DC maturation factor.

Kits comprising a viral vector encoding a sequence of interest (typically an antigen) and optionally, a polynucleotide sequence encoding a DC maturation factor are also contemplated herein. In some kits, the kit includes at least one plasmid encoding virus packaging components and a vector encoding Sindbis virus E2 glycoprotein variant.

A kit may also contain instructions. Instructions typically include a tangible expression describing the virus and, optionally, other components included in the kit, and methods for administration, including methods for determining the proper state of the subject, the proper dosage amount, and the proper administration method, for administering the virus. Instructions can also include guidance for monitoring the subject over the duration of the treatment time.

Kits provided herein also can include a device for administering a virus to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a virus of the kit will be compatible with the virus of the kit; for example, a needle-less injection device such as a high pressure injection device can be included in kits with viruses not damaged by high pressure injection, but is typically not included in kits with viruses damaged by high pressure injection.

Kits provided herein also can include a device for administering a compound, such as a DC activator or stimulator, to a subject. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically the device for administering the compound of the kit will be compatible with the desired method of administration of the compound.

The following are some of the embodiments of the lentiviral vectors and methods of use contemplated herein.

Embodiment 1 is a composition comprising a dendritic cell-targeting lentiviral vector particle wherein the particle comprises a lentiviral vector genome comprising a polynucleotide sequence encoding IL-12, for use in the treatment of cancer wherein the composition is administered intratumorally.

Embodiment 2 is the composition for use according to embodiment 1 wherein the IL-12 is a single chain IL-12 (scIL-12).

Embodiment 3 is the composition for use according to embodiment 2 wherein the scIL-12 comprises p35-L-p40.

Embodiment 4 is the composition for use according to embodiment 2 wherein the scIL-12 comprises p40-L-p35.

Embodiment 5 is the composition for use according to any of the prior embodiments wherein the lentiviral vector particle comprises a modified alphavirus E2 glycoprotein which selectively binds to dendritic cells expressing DC-SIGN.

Embodiment 6 is the composition for use according to any of the prior embodiments wherein the lentiviral vector particle comprises an envelope comprising a Sindbis virus E2 glycoprotein of SEQ ID NO: 1 in which 160X is absent or is an amino acid other than glutamic acid, or a variant of SEQ ID NO: 1 thereof having at least 80% identity to SEQ ID NO: 1 and in which 160X is absent or is an amino acid other than glutamic acid, capable of infecting dendritic cells; wherein E2 is not part of a fusion protein with Sindbis virus E3.

Embodiment 7 is the composition for use according to any of the prior embodiments wherein the treatment further comprises administering an adjuvant intratumorally.

Embodiment 8 is the composition for use according to any of the prior embodiments wherein the adjuvant is an aqueous or oil in water emulsion formulation of glucopyranosyl lipid A (GLA).

Embodiment 9 is the composition for use according to any of the prior embodiments wherein the composition comprising the lentiviral vector particle further comprises an aqueous formulation of glucopyranosyl lipid A (GLA).

Embodiment 10 is the composition for use according to any of the prior embodiments wherein the lentiviral vector particle is administered in a single dose.

Embodiment 11 is the composition for use according to any of the prior embodiments wherein the lentiviral vector particle produces a level of IL-12 between about 0.1 µg and 1 µg/1E10 vector genomes produced during the first 48 hours as measured in an in vitro transduction assay.

Embodiment 12 is the composition for use according to any of the prior embodiments wherein the treatment further comprises regulatory T cell depletion.

Embodiment 13 is the composition for use according to any of the prior embodiments wherein the regulatory T cell depletion comprises systemic administration of cyclophosphamide or an anti-CD25 antibody.

Embodiment 14 is the composition for use according to any of the prior embodiments wherein the systemic administration of cyclophosphamide or an anti-CD25 antibody is prior to the intratumoral injection of the composition comprising the lentiviral vector.

Embodiment 15 is the composition for use according to any of the prior embodiments wherein the treatment further comprises administering a second lentiviral vector particle encoding a tumor antigen.

Embodiment 16 is a product comprising: (a) a first composition a dendritic cell-targeting lentiviral vector particle comprising a lentiviral vector genome comprising a sequence encoding IL-12; and (b) a second composition comprising a second lentiviral vector particle encoding a tumor antigen; for use in a method of treating cancer in a subject wherein the first composition is administered intratumorally and the second composition is administered by a different route.

Embodiment 17 is the product of embodiment 16 wherein the second composition is administered intradermally, subcutaneously or intramuscularly.

Embodiment 18 is the product of any of embodiments 16-17 wherein the first composition and the second composition are administered concurrently.

Embodiment 19 is the product of any of embodiments 16-18 wherein the first composition and the second composition are administered sequentially.

Embodiment 20 is a lentiviral vector particle comprising an envelope comprising a Sindbis virus E2 glycoprotein of SEQ ID NO: 1 in which 160X is absent or is an amino acid other than glutamic acid, or a variant of SEQ ID NO: 1 thereof having at least 80% identity to SEQ ID NO: 1 and in which 160X is absent or is an amino acid other than glutamic acid, capable of infecting dendritic cells; wherein E2 is not part of a fusion protein with Sindbis virus E3; and a lentiviral vector genome comprising a sequence encoding IL-23.

Embodiment 21 is a lentiviral vector particle comprising: a.) an envelope comprising a Sindbis virus E2 glycoprotein of SEQ ID NO: 1 in which 160X is absent or is an amino acid other than glutamic acid, or a variant of SEQ ID NO: 1 thereof having at least 80% identity to SEQ ID NO: 1 and in which 160X is absent or is an amino acid other than glutamic acid, capable of infecting dendritic cells; wherein E2 is not part of a fusion protein with Sindbis virus E3; and b.) a lentiviral vector genome comprising a polynucleotide sequence encoding IL-12.

Embodiment 22 is the lentiviral vector particle of embodiment 21 wherein the IL-12 is a single chain IL-12 (scIL-12).

Embodiment 23 is the lentiviral vector particle of any one of embodiments 21-22 wherein the scIL-12 comprises p35-L-p40.

Embodiment 24 is the lentiviral vector particle of any one of embodiments 21-23 wherein the scIL-12 comprises p40-L-p35.

Embodiment 25 is the lentiviral vector particle of any one of embodiments 21-24 wherein the lentiviral vector genome further comprises a sequence encoding an antigen.

Embodiment 26 is the lentiviral vector particle of any one of embodiments 21-25 wherein the antigen is a tumor associated antigen, a viral antigen, a bacterial antigen or a fungal antigen.

Embodiment 27 is the lentiviral vector particle of embodiment 26 wherein the tumor associated antigen is selected from the group consisting of prostatic acid phosphatase, prostate specific antigen, NKX3.1, prostate specific membrane antigen, PRAME; BAGE; RAGE, NY-ESO-1, SAGE, HAGE, GAGE, Plu-1, HASH-1, HasH-2, Cripto, Criptin, MART-1/Melan-A, gp100, gp75, mda-7, tyrosinase, tyrosinase-related protein, p53, Ras, c-Myc, A-Raf, B-Raf, and C-Raf, MAGE-A1, MAGE-A2, MAGE-A3, MAGE-A4, MAGE-A6, MAGE-A10, MAGE-A12, MART-1, BAGE, DAM-6, -10, GAGE-1, GAGE-2, GAGE-8, GAGE-3, GAGE-4, GAGE-5, GAGE-6, GAGE-7B, NA88-A, MART-1, MC1R, Gp100, PSM, TRP-1, TRP-2, ART-4, CAMEL, CEA, Cyp-B, hTERT, hTRT, iCE, MUC1, MUC2, PRAME, P15, RU1, RU2, SART-1, SART-3, Wilms' tumor antigen (WT1), AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, Epidermal Growth Factor receptor (EGFR and EGFRvIII), platelet derived growth factor receptor (PDGFR), vascular endothelial growth factor receptor (VEGFR), integrin-linked kinase (ILK), STAT3, STAT5, STAT6, HIF-1, HIF-2, Nuclear Factor-Kappa B (NF-κB), Notch1-4, c-Met, mammalian targets of rapamycin (mTOR), WNT, PMSA, PR-3, MDM2, Mesothelin, renal cell carcinoma-5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGs5, SART3, STn, PAX5, OY-TES1, sperm protein 17, LCK, HMWMAA, AKAP-4, SSX2, XAGE 1, B7H3, legumain, TIE2, Page4, MAD-CT-1, FAP, MAD-CT-2, and fos related antigen 1.

Embodiment 28 is a method of treating cancer in a subject, comprising administering to the subject an effective amount of a composition comprising any of the lentiviral vector particles described herein.

Embodiment 29 is the method of embodiment 28 further comprising administering to the subject an effective amount of a composition comprising a second lentiviral vector encoding a tumor antigen.

Embodiment 30 is the method of embodiments 28-29 wherein the lentiviral vector particle expressing embodiment 21 and the second lentiviral vector are administered concurrently.

Embodiment 31 is the method of any one of embodiments 28-29 wherein the lentiviral vector particle of embodiment 21 and the second lentiviral vector are administered sequentially at different times.

Embodiment 32 is the method of embodiment 29 wherein the lentiviral vector particle of embodiment 21 and the second lentiviral vector are administered by different routes.

Embodiment 33 is the method of Embodiment 29 wherein the lentiviral vector particle of Embodiment 21 and the second lentiviral vector are administered at different sites.

Embodiment 34 is the method of embodiment 29 wherein the lentiviral vector particle of Embodiment 21 and the second lentiviral vector are administered at different sites, by the same route.

Embodiment 35 is the method of Embodiment 28 wherein the lentiviral vector particle is administered intratumorally.

Embodiment 36 is the method of embodiment 29 wherein the lentiviral vector particle of Embodiment 21 is administered intratumorally and the second lentiviral vector is administered concurrently at a different site and by a different route.

Embodiment 37 is a method of treating cancer in a subject, comprising administering to the subject an effective amount of a composition comprising the lentiviral vector particle of Embodiment 25.

Embodiment 38 is the method of Embodiment 28 wherein the method further comprises administering intratumorally a TLR4 agonist.

Embodiment 39 is the method of Embodiment 38 wherein the TLR4 agonist is an aqueous or oil in water emulsion formulation of glucopyranosyl lipid A (GLA).

Embodiment 40 is the method of Embodiment 35 wherein the composition comprising the lentiviral vector particle further comprises an aqueous formulation of glucopyranosyl lipid A (GLA).

Embodiment 41 is any one of the methods herein wherein the lentiviral vector particle is administered in a single dose.

Embodiment 42 is any one of the methods herein wherein the lentiviral vector particle produces a low-level of IL-12.

Embodiment 43 is any one of the methods herein wherein the low-level of IL-12 is between about 0.1 μg and 1 μg/1E10 vector genomes produced during the first 48 hours as measured in an in vitro transduction assay.

Embodiment 44 is any one of the methods herein wherein the lentiviral vector particle is administered intratumorally.

Embodiment 45 is the lentiviral vector particle according to any one of embodiments 21-27 for use in a method of treatment of a human or animal subject.

Embodiment 46 is a composition comprising the lentiviral vector particle according to embodiment 21 and a second lentiviral vector particle encoding a tumor antigen.

Embodiment 47 is a therapeutic or prophylactic vaccine comprising the lentiviral vector particles of embodiment 25 and a pharmaceutically acceptable excipient.

The following examples are offered by way of illustration, and not by way of limitation.

EXAMPLES

Example 1

Engineering of a Lentiviral Vector Expressing IL-12

A lentiviral vector pseudotyped with a modified Sindbis E2 envelope glycoprotein that targets the lentiviral vector to dendritic cells expressing DC-SIGN (see e.g. U.S. Pat. Nos. 8,187,872 and 8,323,662) was engineered to express murine IL-12 (referred to herein as VP02/IL-12). IL-12 is composed of 2 disulfide linked to subunits, p35 and p40. Two different constructs were prepared with both subunits connected via an elastin linker but in different orientations: p35-elastin-p40 and p40-elastin-p35 (p35-L-p40; p40-L-p35). Initial experiments showed that the p40-L-p35 vector produced much higher quantities of IL-12. In a functional bioassay, 293-DC-SIGN cells were transduced with VP02/IL-12 candidates and culture supernatants were collected. Murine splenocytes were incubated with the supernatants. In a time course experiment from 1 to 48 hours, spleen culture supernatants were collected and analyzed for secreted IFNγ. The results showed that both VP02/IL-12 candidates produced functional IL-12. However the p40-L-p35 candidate was selected for continued studies.

Further experiments were carried out to quantify the amount of IL-12 produced by the vectors. The experiment was as follows:

Day 0: Seeded 293T-DCSIGN cells at 1e6/well in 6 well with 2.5 ml media

Day 1: Next day, transfect VP02-mIL12(p35-p40) and VP02-mIL12(p40-p35): (using Lipofectamine2000 from Invitrogen) Include VP02-GFP plasmid for positive transfection control.
  1.5 ug plasmid added to 250 ul OptiMEM media
  4.5 ul Lipofectamine2000 reagent added, mix, incubate 30 min at RT
  Add directly to seeded cells Day 1: Transduce vector, 10 ul concentrated/well
  VP02-mIL12 (p35-elastin-p40)—non-integrating, 3.1e11 genomes/ml
  VP02-mIL12 (p40-elastin-p35)—non-integrating, 5.9e11 genomes/ml
  VP02-GFP—non-integrating, 1.9e11 genomes/ml Day 2: replace media with fresh 10% FBS DMEM, include a 1×PBS wash Day 4: collect supernatants and filter through 0.45 uM, store in −80 deg C. until ELISA IL-12 was detected in all supernatants. Plasmid transfection had much higher levels than vector transduction, as expected. The p40-L-p35 vector produced more IL-12 than the reverse orientation. These results are shown in the table below.

|  | pg/ml | ng/ml | ug/ml |
| --- | --- | --- | --- |
| Negative | BLQ | BLQ | BLQ |
| GFP vector | BLQ | BLQ | BLQ |
| 35-40 vector | 4337.6 | 4.3 | 0.0 |
| 40-35 vector | 161973.3 | 162.0 | 0.2 |
| GFP plasmid | BLQ | BLQ | BLQ |
| 35-40 plasmid | 890050.0 | 890.1 | 0.9 |
| 40-35 plasmid | 10698666.7 | 10698.7 | 10.7 |

BLQ: below the limit of quantitation

Example 2

VP02/IL-12 Co-Delivered with Lentiviral Vector Expressing Tumor Antigen Enhanced Tumor-Antigen-Specific CD8 T Cells This experiment shows that co-delivery of VP02/IL-12 with VP02 expressing a tumor antigen enhances the antitumor antigen CD8 T cell response.

Two experiments were carried out to evaluate if the presence of IL-12 generated from the VP02/IL-12 lentiviral vector in combination with the expression of a tumor associated antigen expressed from a VP02 lentiviral vector, can enhance antigen-specific CD8 T cell responses in mice.

Female C57/BL/6 or B6D2/F1 mice were immunized subcutaneously at the base of the tail with VP02/IL-12 and VP02/Tumor antigen (either NY-ESO-1 or CAIX) according to Table 1. Splenic T cell responses were measured 13 days post immunization by intracellular cytokine staining after ex vivo re-stimulation with CD8 reactive peptides.

TABLE 1

| Component | [Stock] | Final Dose/mouse | Dose Volume |
|---|---|---|---|
| VP02/IL-12 | 5.9E11 | 1.5E9, 1.5E10 | 50 µL (s.c.) |
| VP02/hCAIX | 1.4E12 | 1.5E10 | 50 µL (s.c.) |
| VP02/NYESO1 | 1.2E12 | 1.5E10 | 50 µL (s.c.) |

Figure 1:
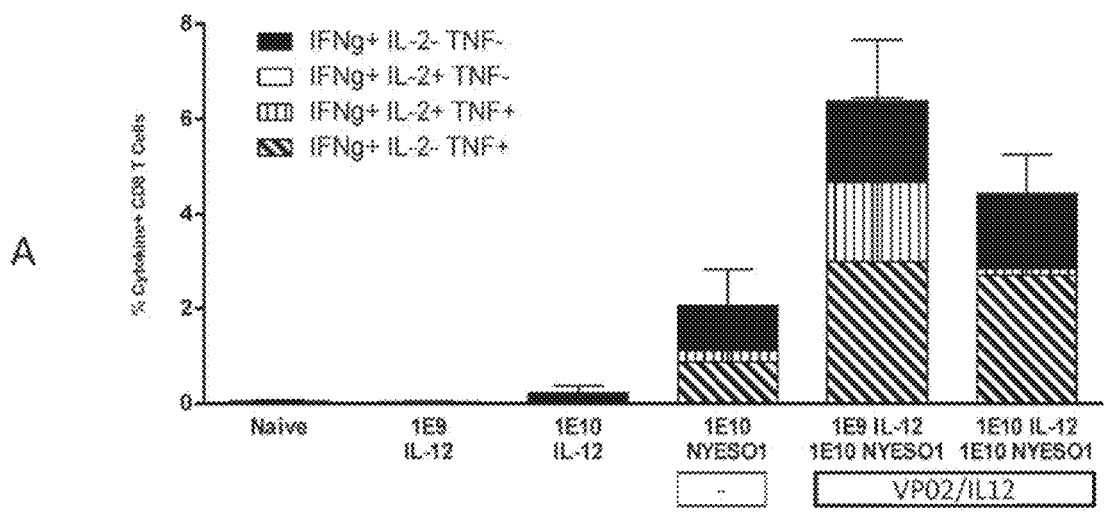
FIG. 1A and FIG. 1B show that co-delivery of VP02/IL-12 with VP02/NY-ESO-1 enhances the anti-NY-ESO-1 CD8 T cell response.
Figure 1:
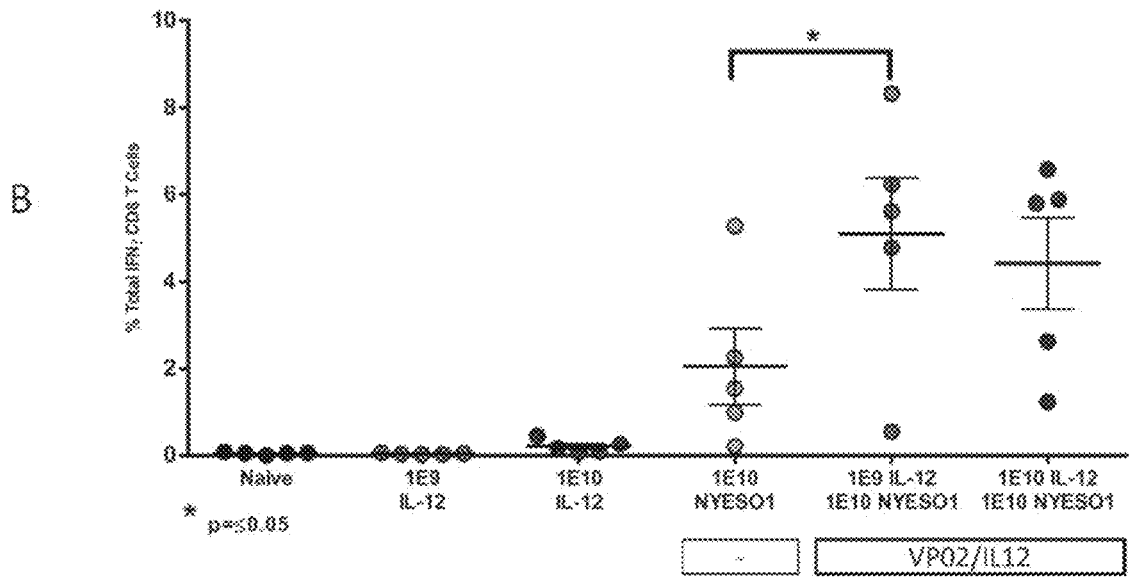
Figure 2:
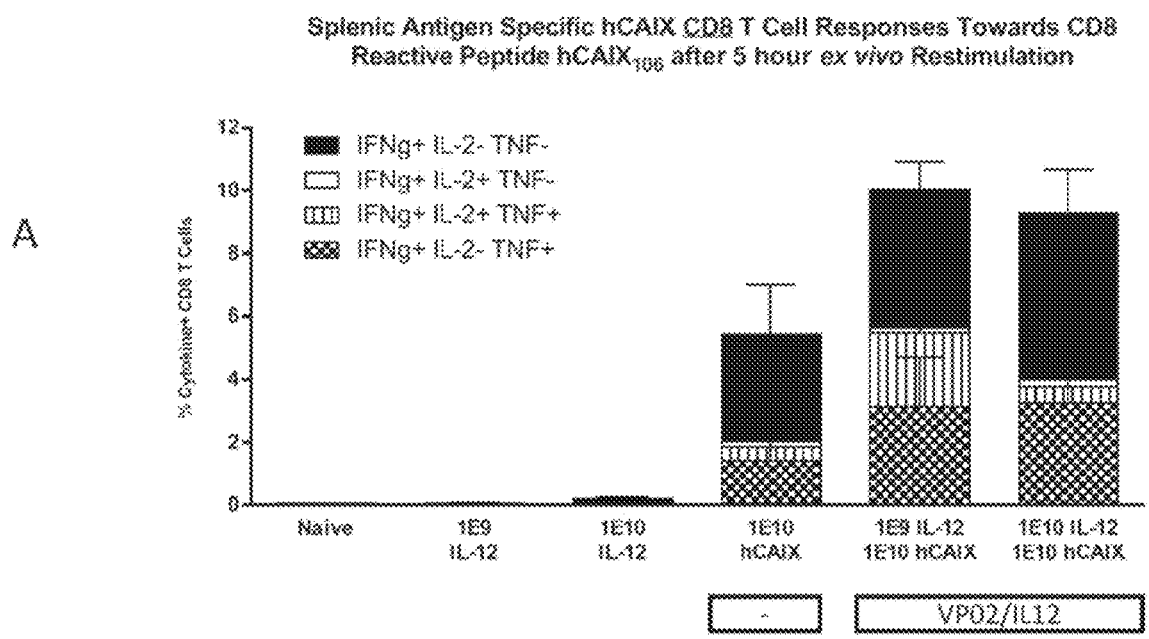
FIG. 2A and FIG. 2B show that co-delivery of VP02/IL-12 with VP02/hCAIX enhances the anti-hCAIX CD8 T cell response.
Figure 2:
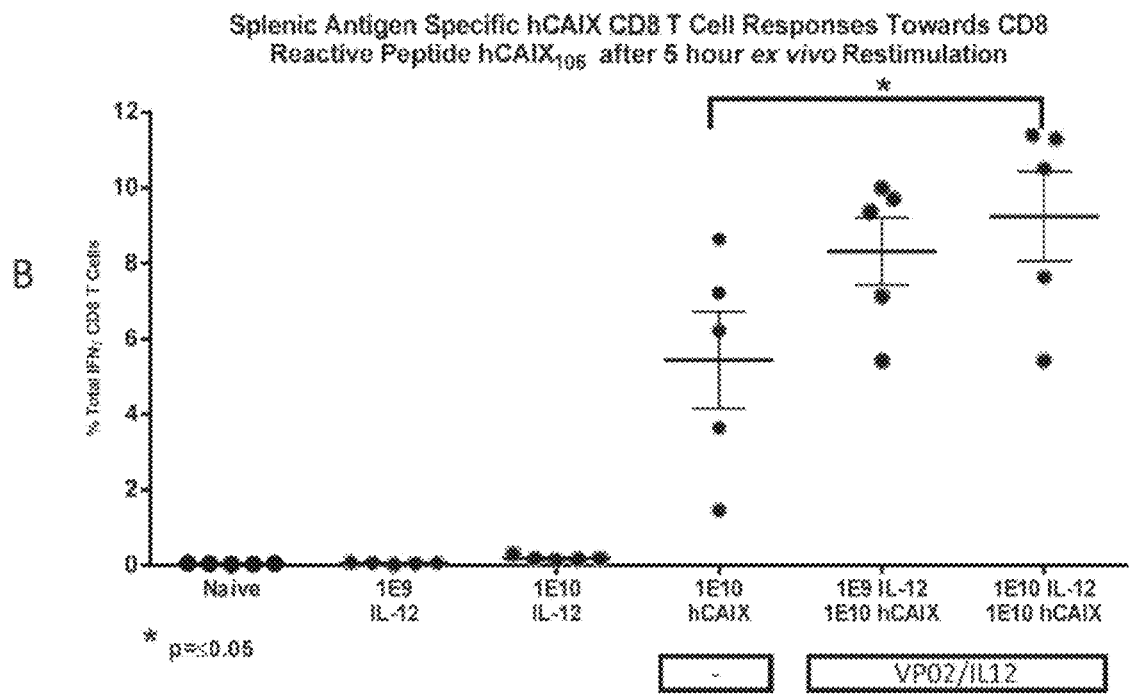

As shown in FIG. 1 and FIG. 2, VP02/IL-12 co-delivered with VP02 expressing NY-ESO-1 (FIG. 1) or hCAIX (FIG. 2) enhanced antigen-specific CD8 responses.

Figure 3:
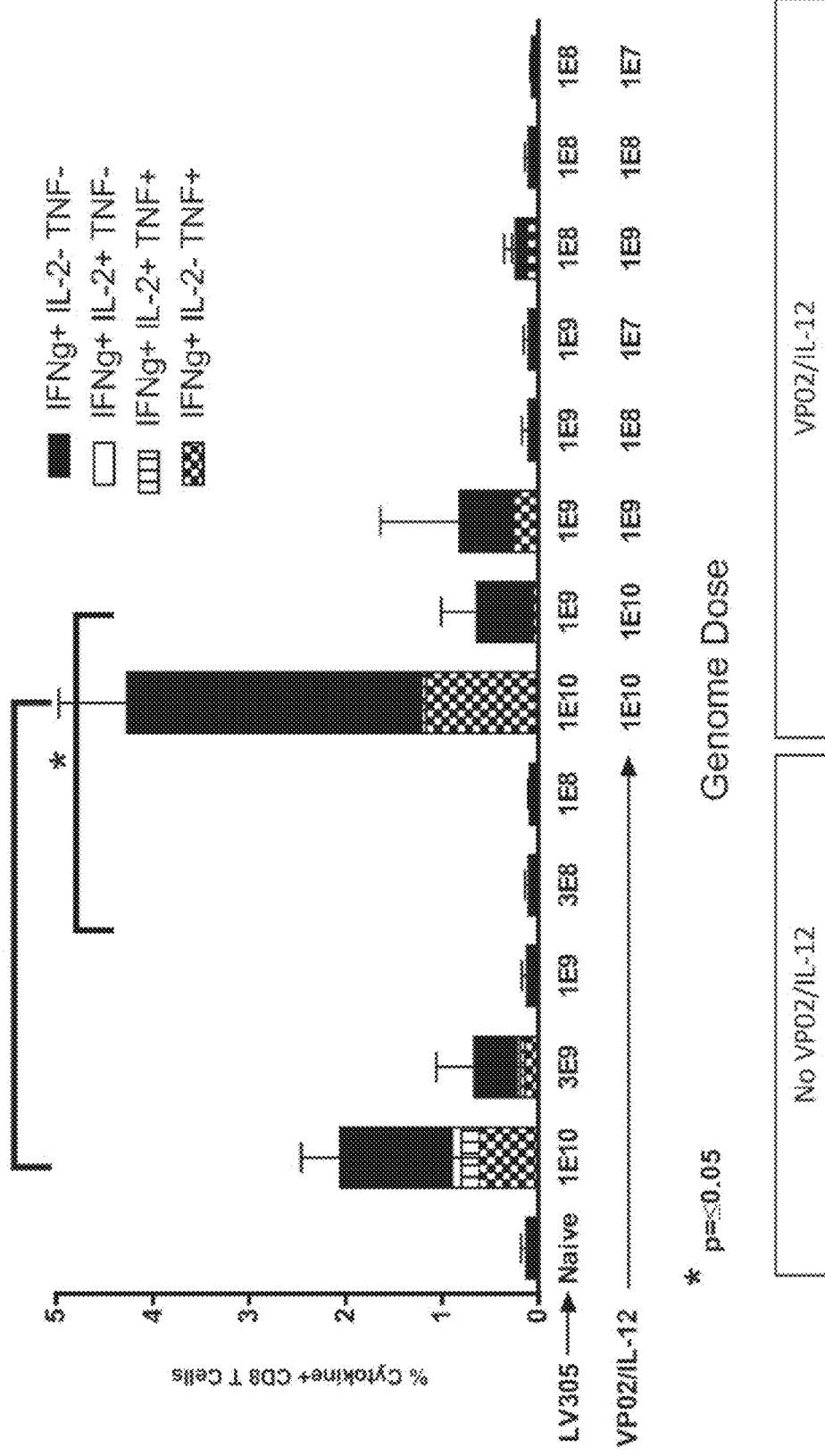
FIG. 3A and FIG. 3B show that co-delivery of VP02/IL-12 significantly enhances antigen-specific CD8 T cell responses against NY-ESO-1 induced by the lentiviral vector VP02/NY-ESO-1.
Figure 3:
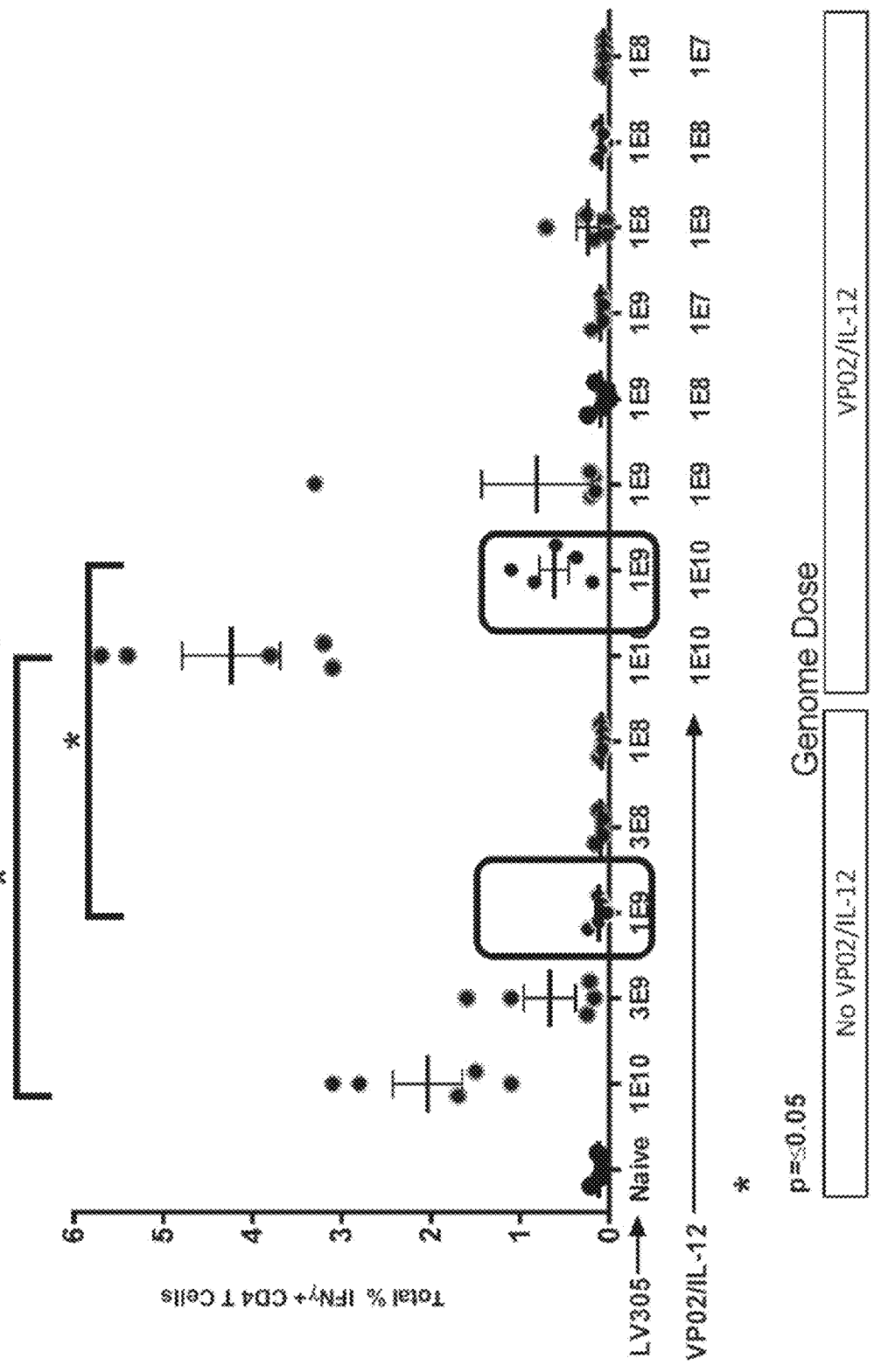
Figure 4:
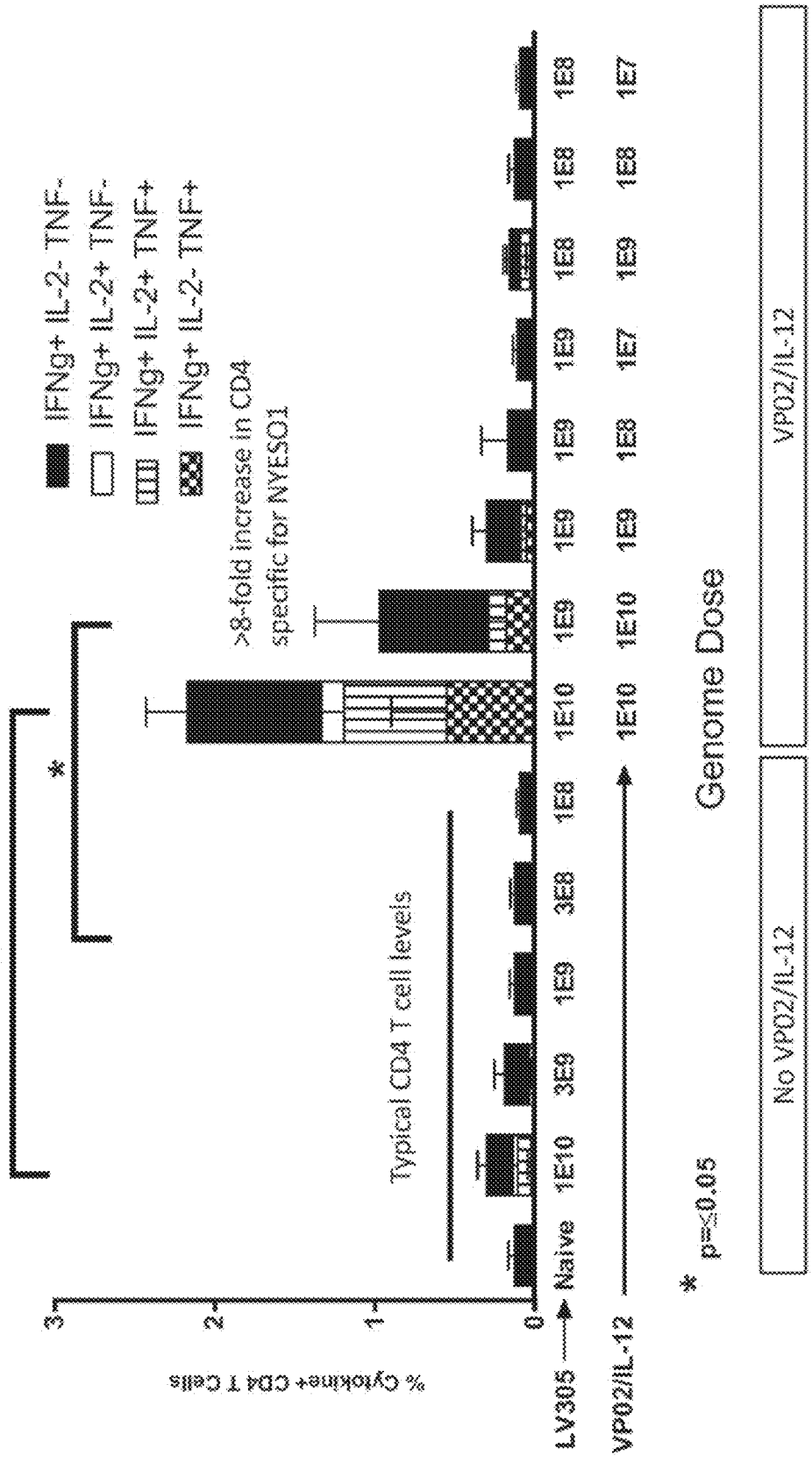
FIG. 4A and FIG. 4B show that co-delivery of VP02/IL-12 significantly enhances antigen-specific CD4 T cell responses against NY-ESO-1 induced by the lentiviral vector VP02/NY-ESO-1.
Figure 5:
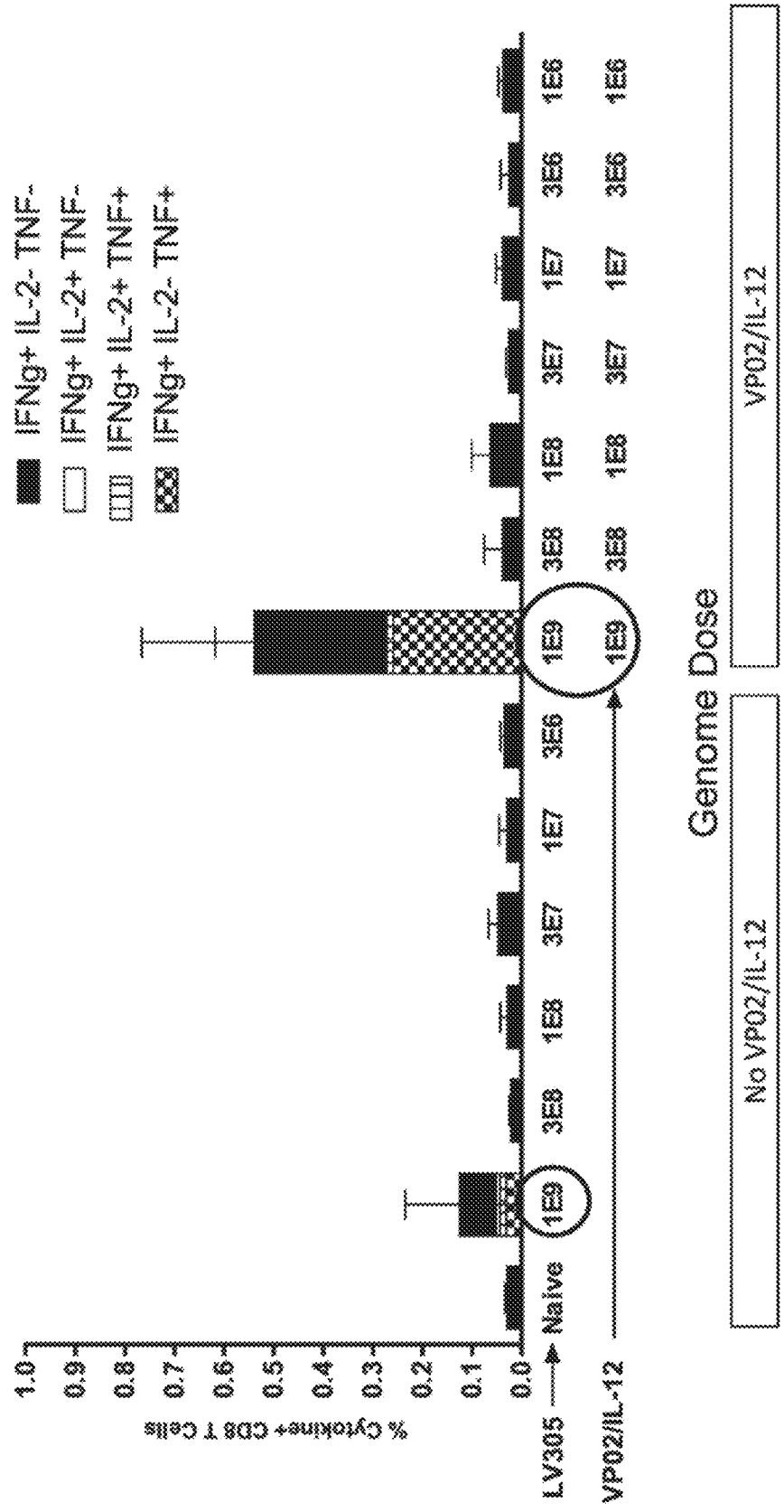
FIG. 5A, FIG. 5B, FIG. 5C and FIG. 5D show that co-administration of even low doses of VP02/IL-12 (1E9 vg dose) with LV305 at borderline immunogenic dose (1E9 vg) enhanced CD8 and CD4 responses.
Figure 5:
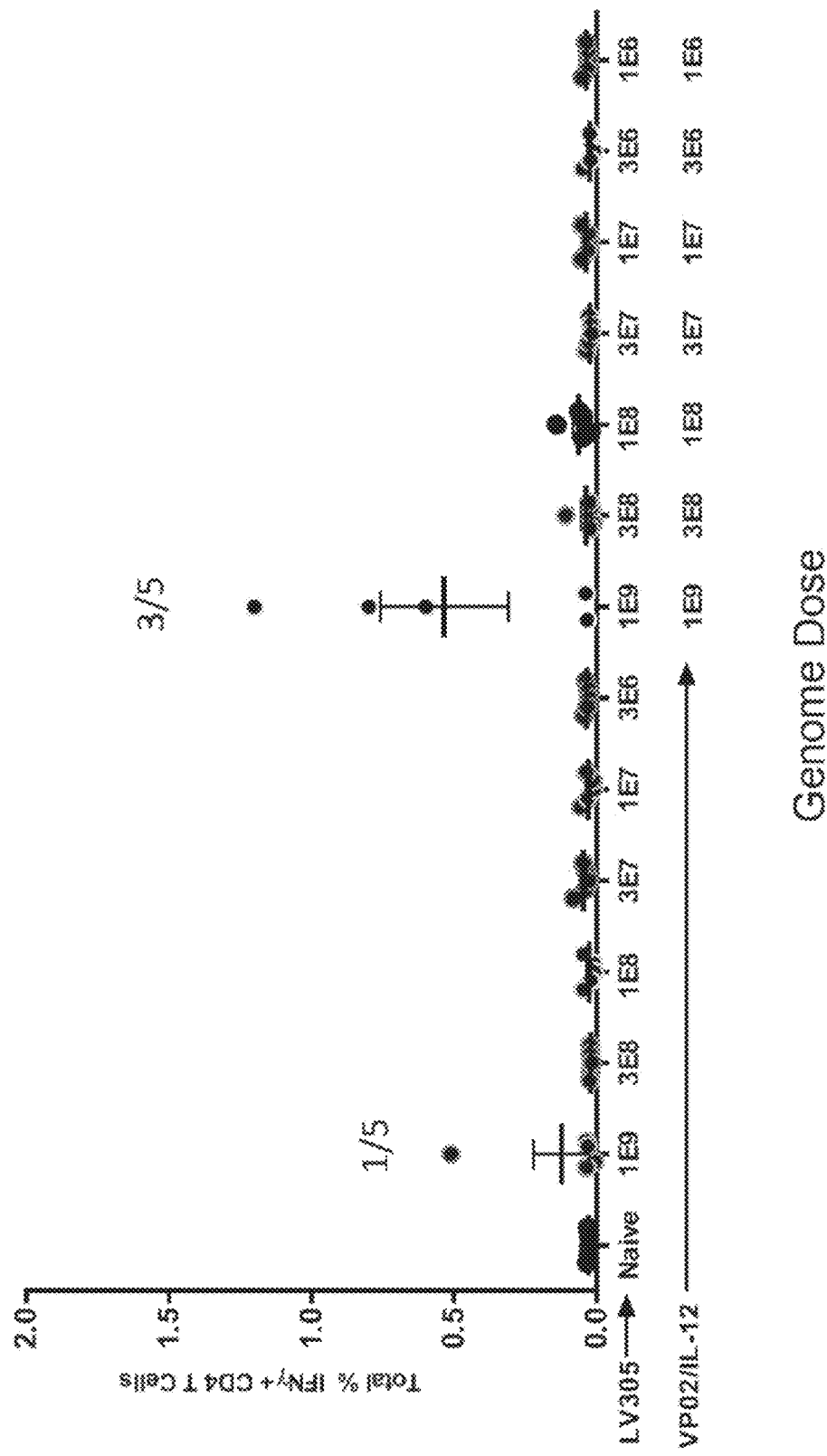
Figure 5:
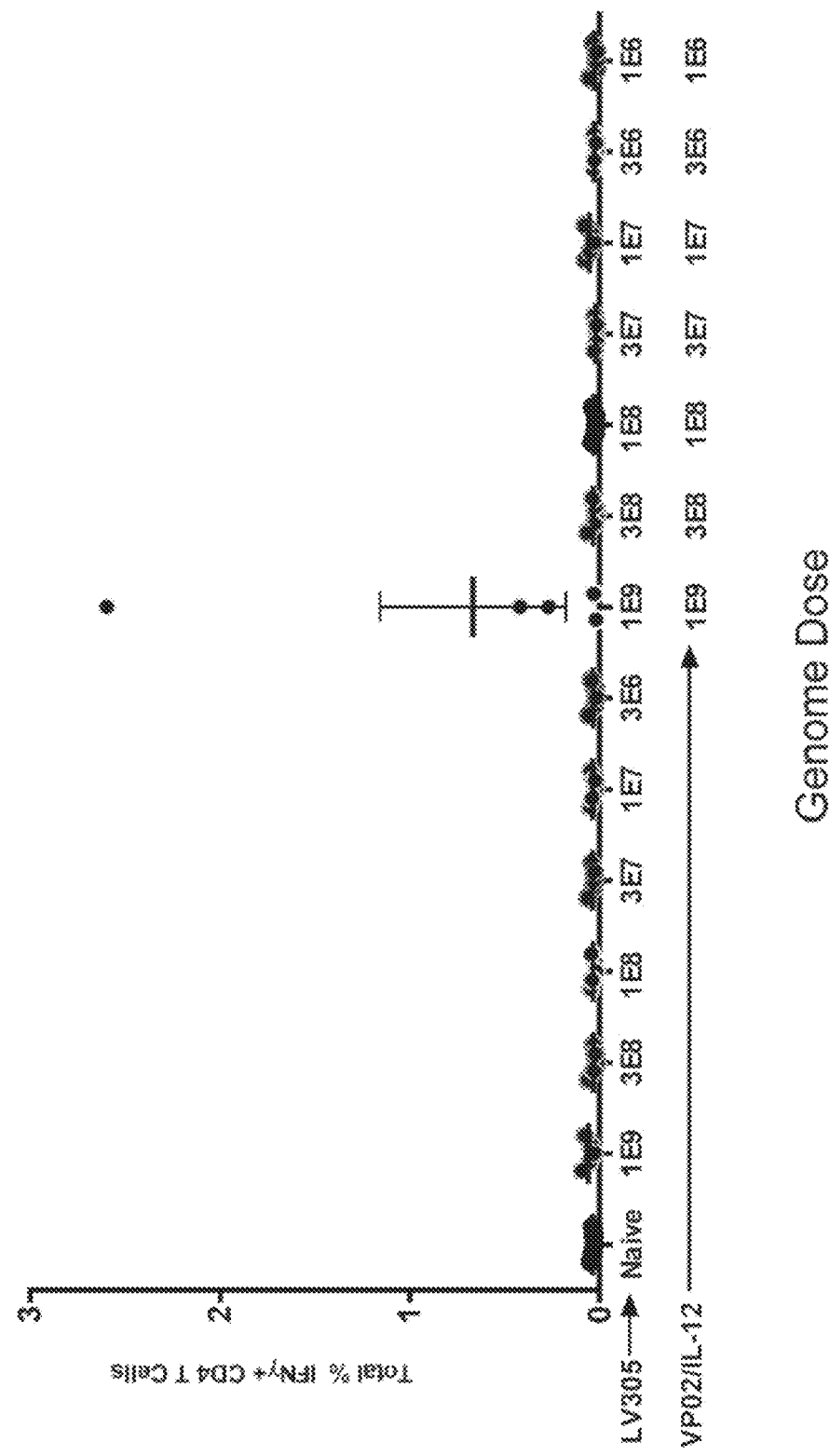

Additional experiments were carried out to further assess the enhancement provided by VP02/IL-12. As shown in FIG. 3, co-administration of VP02/IL-12 with LV305 (VP02 expressing NY-ESO-1) enhances Ag-Specific CD8 T cell responses when administered at relatively high vector genome doses (1E10 vector genomes). Note however that overall expression of IL-12 even at this high v.g. dose is still quite low (e.g., less than 0.5 micrograms produced during the first 48 hours, based on in vitro studies under optimal culture conditions). Note in particular that the anti-NY-ESO-1 antigen-specific immune response generated at 1E9vg in this experiment was in essence non-detectable and this basically undetectable immune response was unexpectedly significantly enhanced by co-delivery of VP02/IL-12 (FIG. 3B). VP02/IL-12 co-delivery also enhances CD4 responses (see FIGS. 4A and 4B).

Co-administration of even lower doses of VP02/IL-12 (1E9 vg dose) with LV305 at borderline immunogenic dose (1E9 vg) enhanced CD8 and CD4 responses (see FIG. 5A-5D).

Example 3

Co-Administration of VP02/IL12 Enhanced the Therapeutic Activity of High Dose of VP02/hCAIX This Example describes experiments conducted to test the therapeutic benefits of VP02/hCAIX with VP02/IL-12 on mice that have been challenged with the BC.12 hCAIX expressing tumor clone.

Mice were injected subcutaneously in their right flank with BC.12 tumor cells expressing hCAIX. Therapy was administered at Day 8. Tumor sizes were recorded every 2-3 days. The basic experimental protocol is shown in Tables 2 and 3 below.

TABLE 2

| Component | [Stock] | Final Dose/mouse | Total Test Article Dose Volume |
|---|---|---|---|
| Full Length hCAIX | 0.3 mg/mL | 5, 0.5 µg | 50 µL |
| VP02/hCAIX | 7.1E11 | 2.5E10 | 50 µL |
| VP02/IL-12 | 5.9E11 | 1E10, 1E6 | 50 µL |

TABLE 3

| Group | n-B6 mice | Vector Dose hCAIX | Vector Dose IL-12 |
|---|---|---|---|
| 1 | 10 | — | — |
| 2 | 5 | — | 1.0E10 (s.c.) |
| 3 | 5 | — | 1.0E6 (s.c.) |
| 4 | 10 | 2.5E10 (s.c.) | — |
| 5 | 10 | 5.0E9 (s.c.) | — |
| 6 | 10 | 2.5E10 (s.c.) | 1.0E10 (s.c.) |
| 7 | 10 | 5.0E9 (s.c.) | 1.0E10 (s.c.) |

Figure 6:
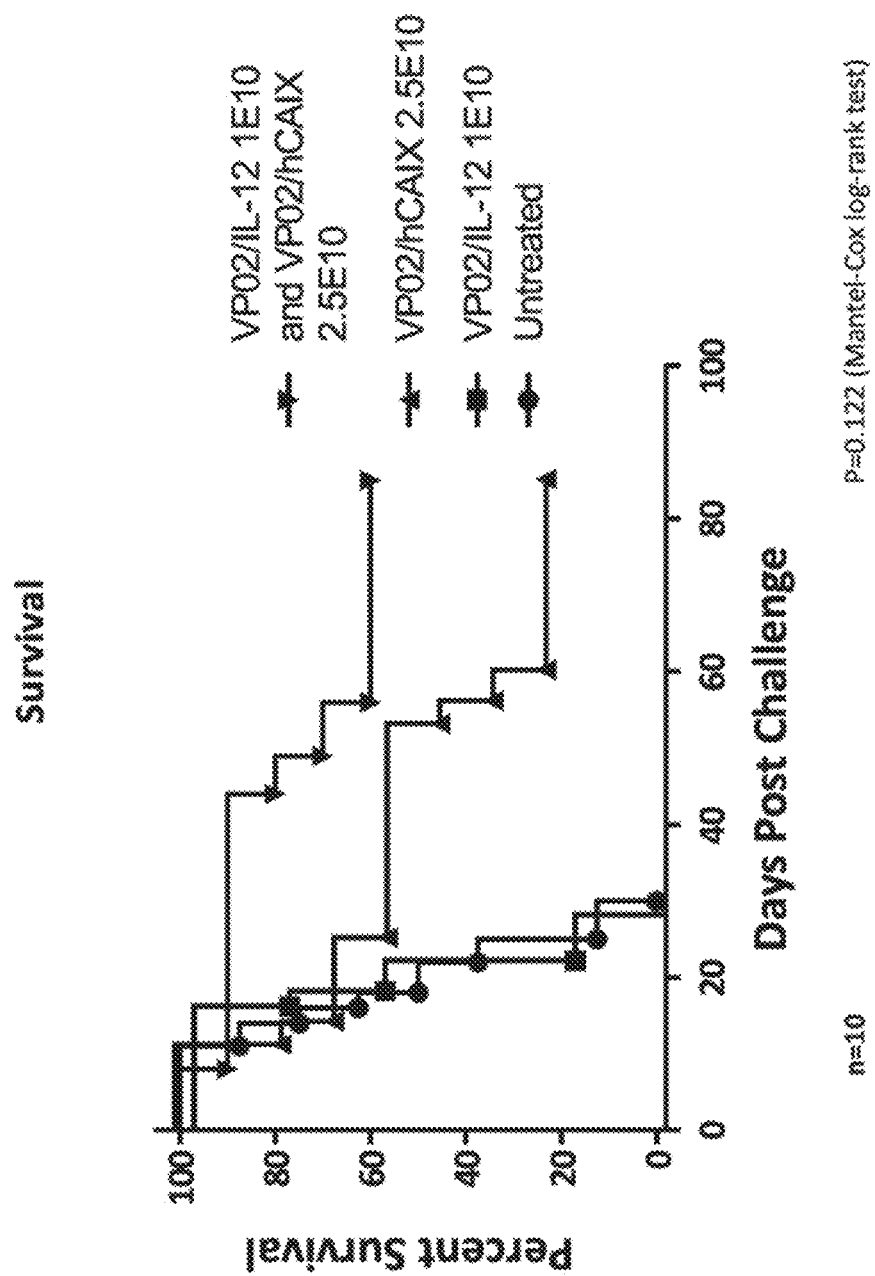
FIG. 6 shows that co-administration of VP02/IL12 enhanced the therapeutic activity of high dose of VP02/hCAIX but the difference was not significant.

As shown in FIG. 6, co-administration of VP02/IL12 enhanced the therapeutic activity of high dose of VP02/hCAIX but the difference was not significant. Similarly, coadministration of VP02/IL-12 enhanced the therapeutic activity of mid-dose of VP02/hCAIX however the difference was not significant.

Example 4

Co-Administration of VP02/IL12 Enhanced the Therapeutic Activity of Low Dose of VP02/NY-ESO-1 (LV305)

This experiment shows that coadministration of VP02/IL-12 enhanced the therapeutic activity of a sub immunogenic dose of VP02 expressing NY-ESO-1 (LV305).

For this experiment, the methods were: Day 0: Challenge BALB/c mice with $1.5 \times 10^5$ CIN.23 cells, tail vein i.v. Day 3: Immunize with VP02/NYESO1±VP02/mIL12, tailbase. Day 18: Lymphocytes were isolated from tumors and spleens were analyzed via flow cytometry.

Figure 7:
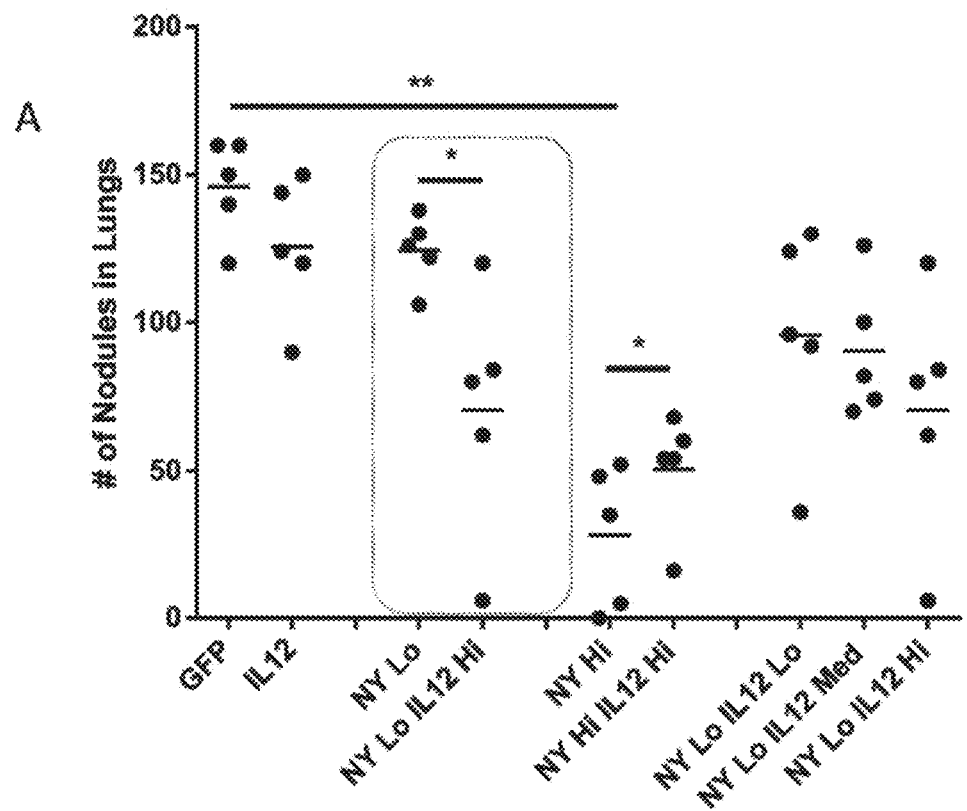
FIG. 7A and FIG. 7B show that antitumor efficacy mediated by low dose LV305 was significantly enhanced by ad-mixing with VP02/IL-12 and the antitumor efficacy correlated with the magnitude of NY-ESO-1-specific CD8 T cell (FIG. 7B).
Figure 7:
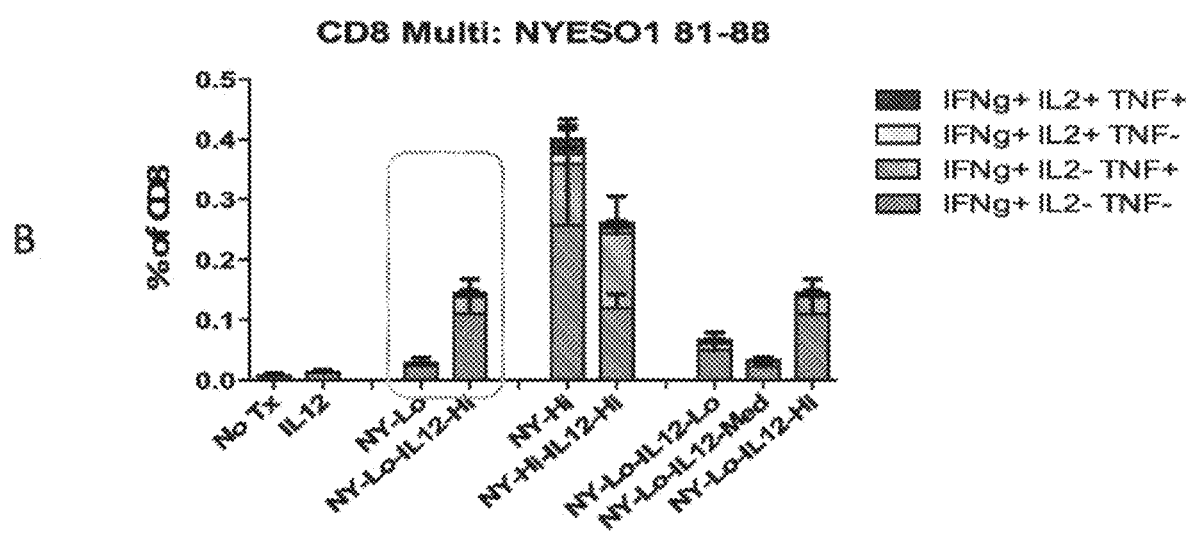

As shown in FIG. 7A, antitumor efficacy mediated by low dose LV305 was significantly enhanced by ad-mixing with VP02/IL12 and the antitumor efficacy correlated with the magnitude of NYESO1-specific CD8 T cell (FIG. 7B).

Summary and conclusions for Examples 1-4: VP02/IL12 can be used to enhance CD8 and CD4 responses to VP02-based immunotherapy including enhanced anti-tumor efficacy. The effect on CD8 responses is typically equivalent to a 3-5 fold LV305 dose increase, up to 10+ fold dose equivalent for enhancement of CD4 responses. VP02/IL12 is typically most effective when VP02 immunotherapy (e.g. LV305) induces weaker response levels. For LV305, in the mouse models described herein, such responses are typically induced at the 1E9-1E10 vg dose range. VP02/IL12 has less effect when used at low doses. In particular, only occasionally did doses lower than 1E10 vg of IL-12 result in any immune-enhancing effect for CD8 response. The VP02/IL12 is typically effective when used at equal (or higher) doses as VP02/Ag, suggesting that it can be effectively expressed from the same vector as the tumor antigen against which an immune response is desired.

Example 5

Administration of VP02 Expressing Other Cytokines

A battery of 7 different cytokines expressed from VP02 were tested for their ability to enhance tumor-specific antigen specific immune responses.

The cytokines tested were VP02/IL-15, VP02/IL-18, VP02/IL-21, VP02/IL-23, VP02/IL-1p, VP02/IL-TNF, VP02/IL-IFNγ. BALB/c Mice were immunized twice, 3 weeks apart at 3 dosage levels of LV305 (hi, med, lo) with a constant dose of VP02/IL-X (hi). At day 14, T-cell responses were measured in peripheral blood post-prime (medium dose only). At day 33 post boost, lymphocytes were isolated from spleens for analysis by ICS and flow cytometry.

Figure 8:
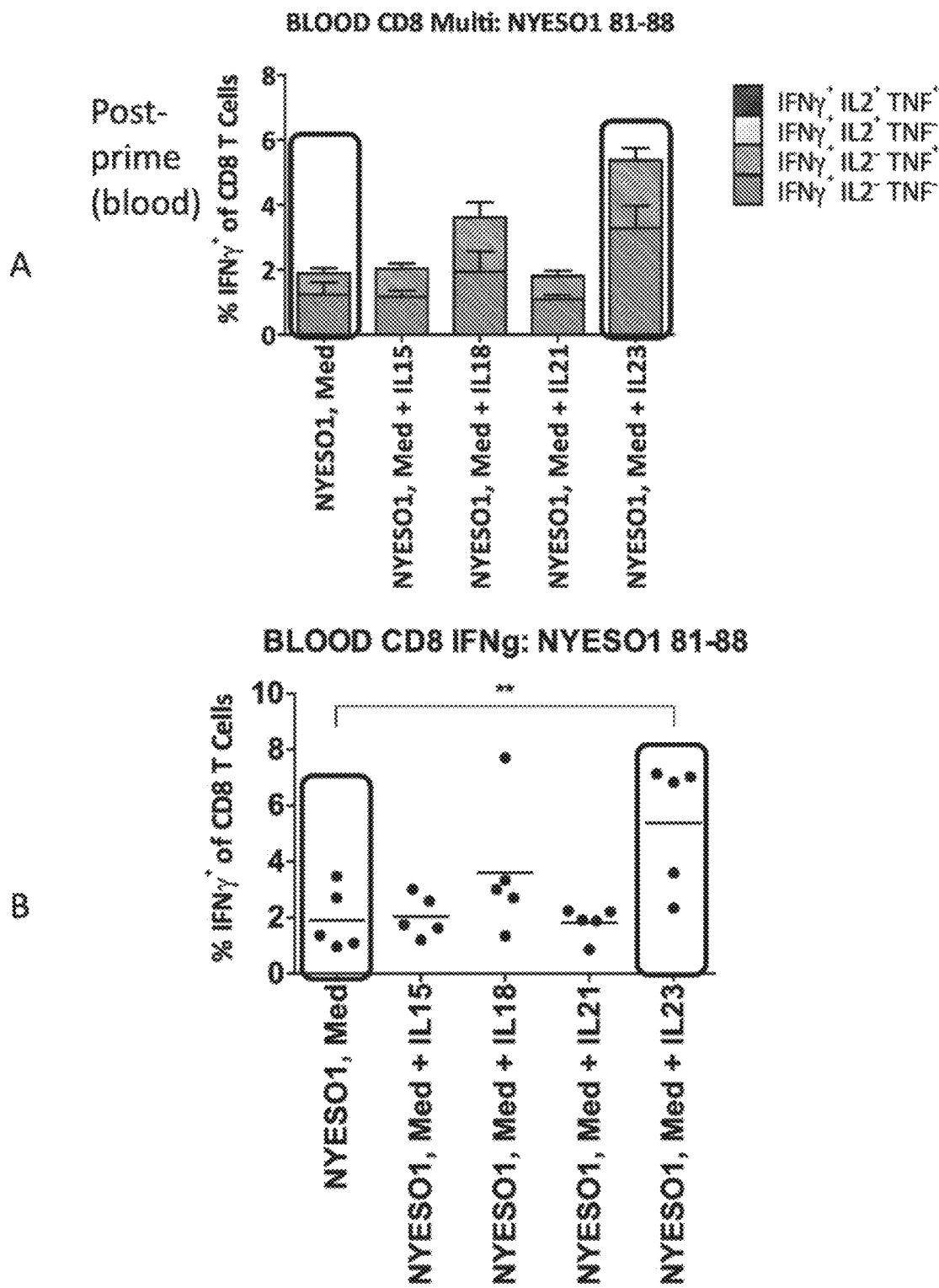
FIG. 8A and FIG. 8B show that VP02/IL-23 was able to significantly enhance LV305-induced CD8 T cell responses in PBMC after a priming immunization (FIG. 8B).
Figure 9:
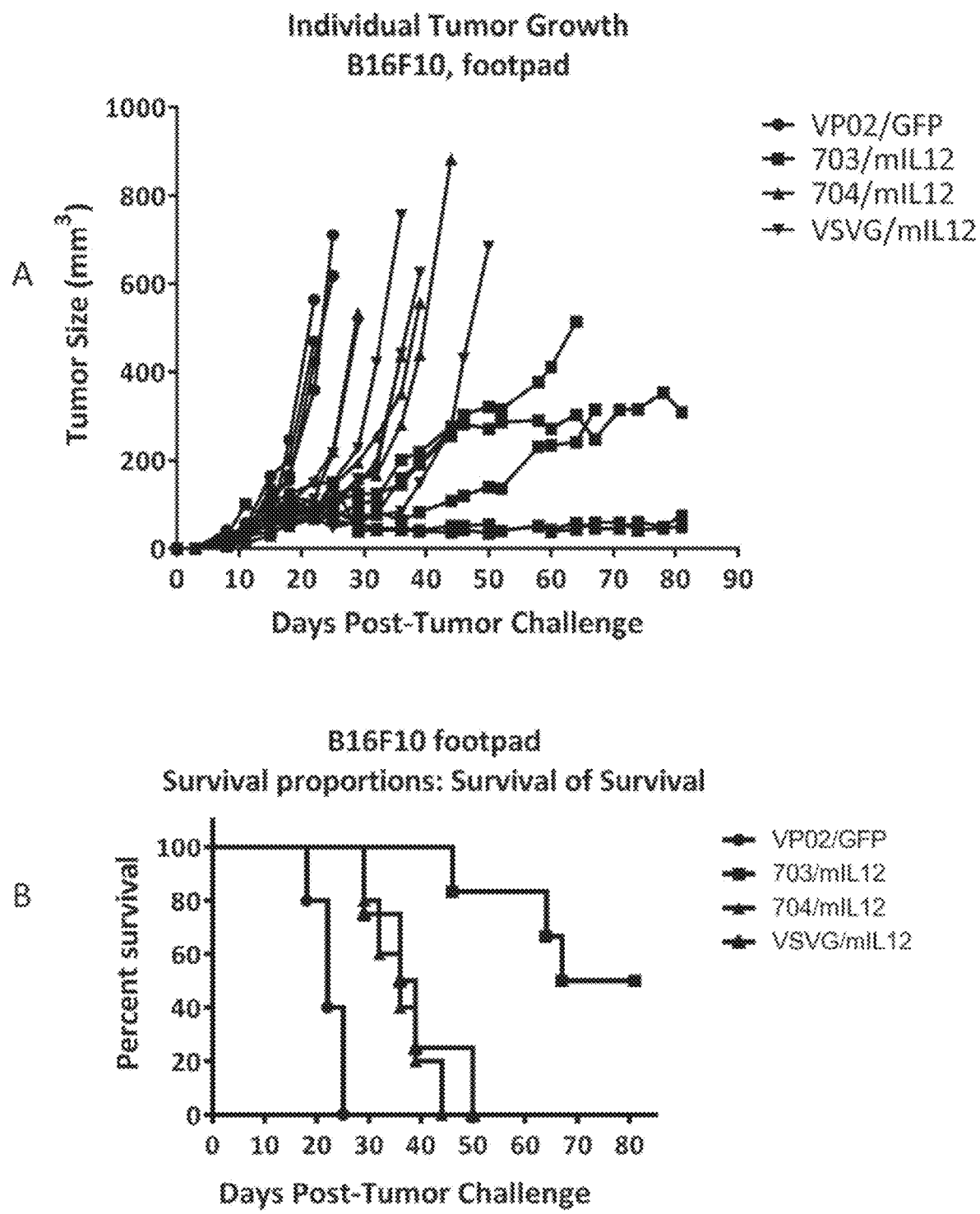
FIG. 9A and FIG. 9B show the antitumor efficacy of intratumoral injection of LV/IL-12 in a B16F10 footpad murine tumor model.
Figure 10:
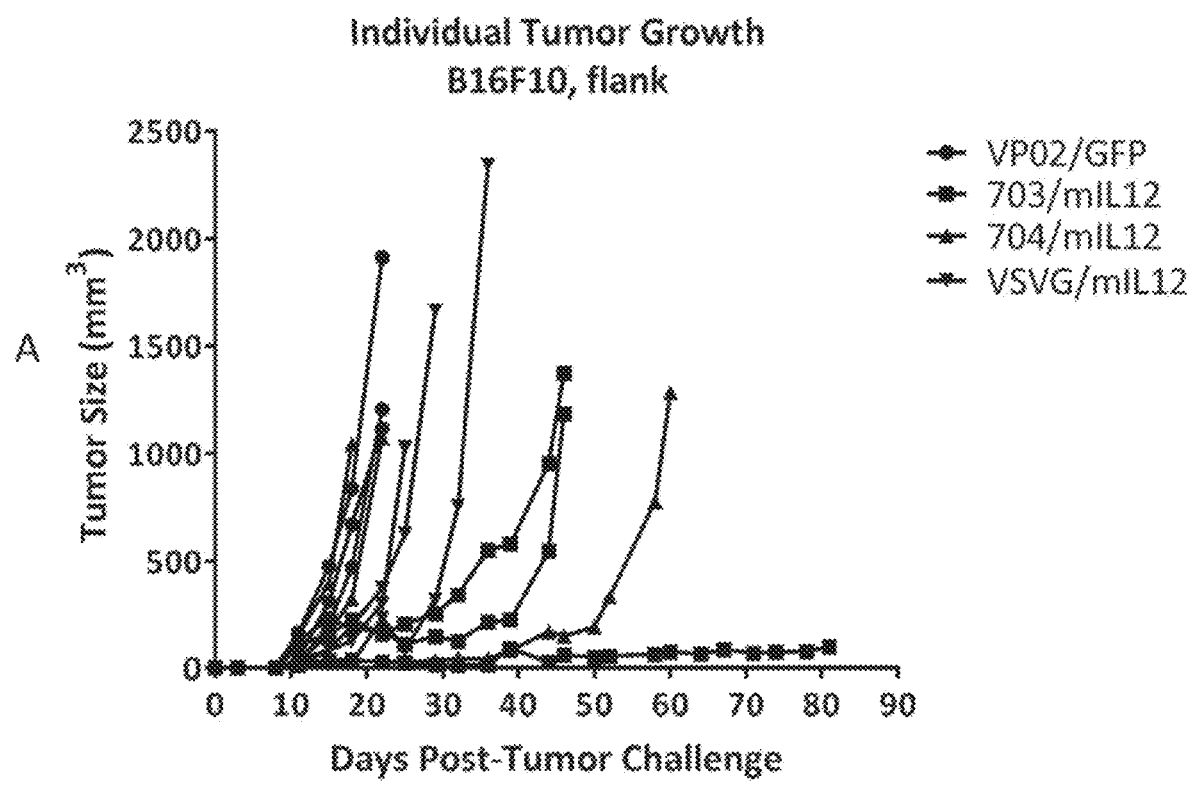
FIG. 10A and FIG. 10B show the antitumor efficacy of intratumoral injection of LV/IL-12 in a B16F10 flank murine tumor model.
Figure 10:
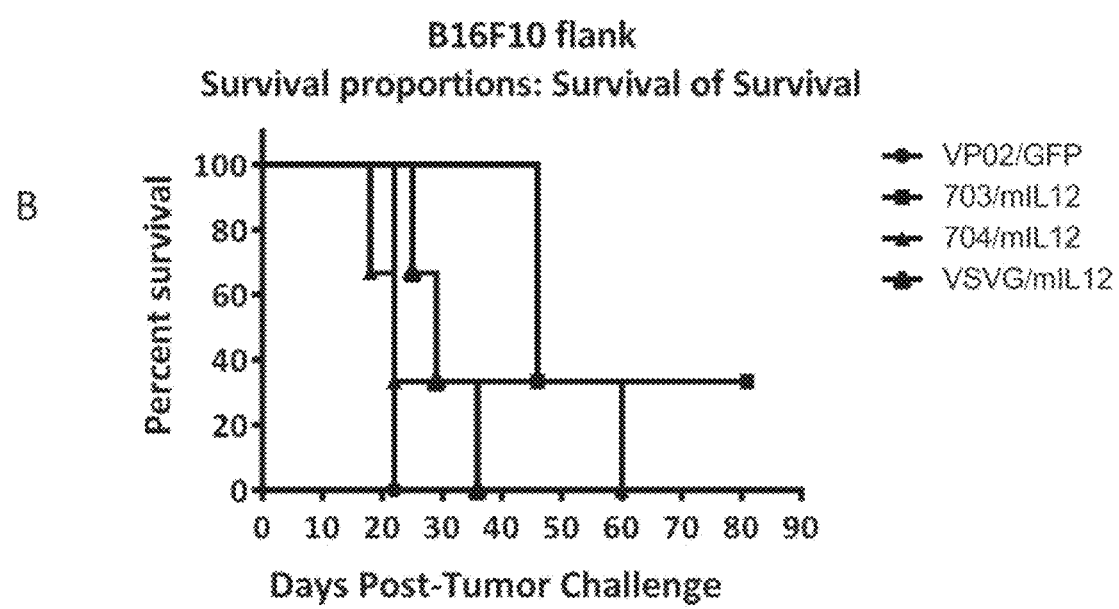
Figure 11:
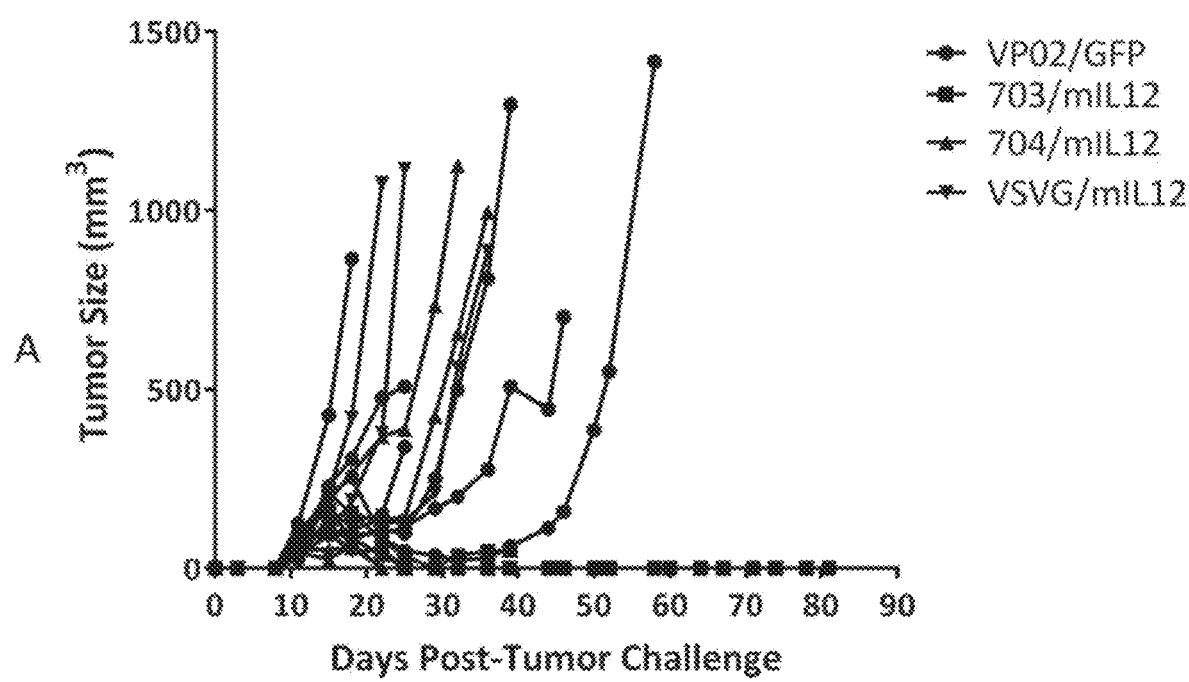
FIG. 11A and FIG. 11B show the antitumor efficacy of intratumoral injection of LV/IL-12 in a P815 murine tumor model.
Figure 11:
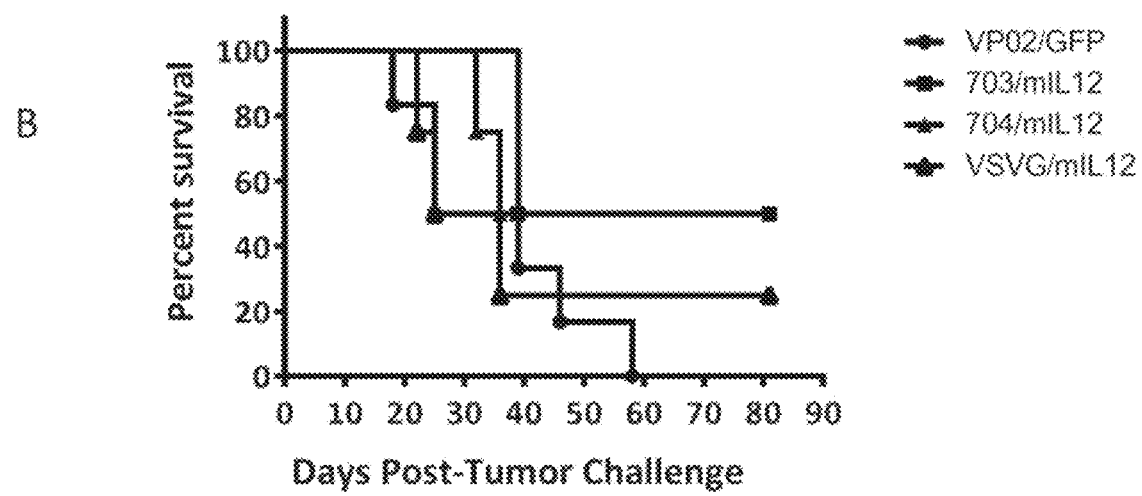
Figure 12:
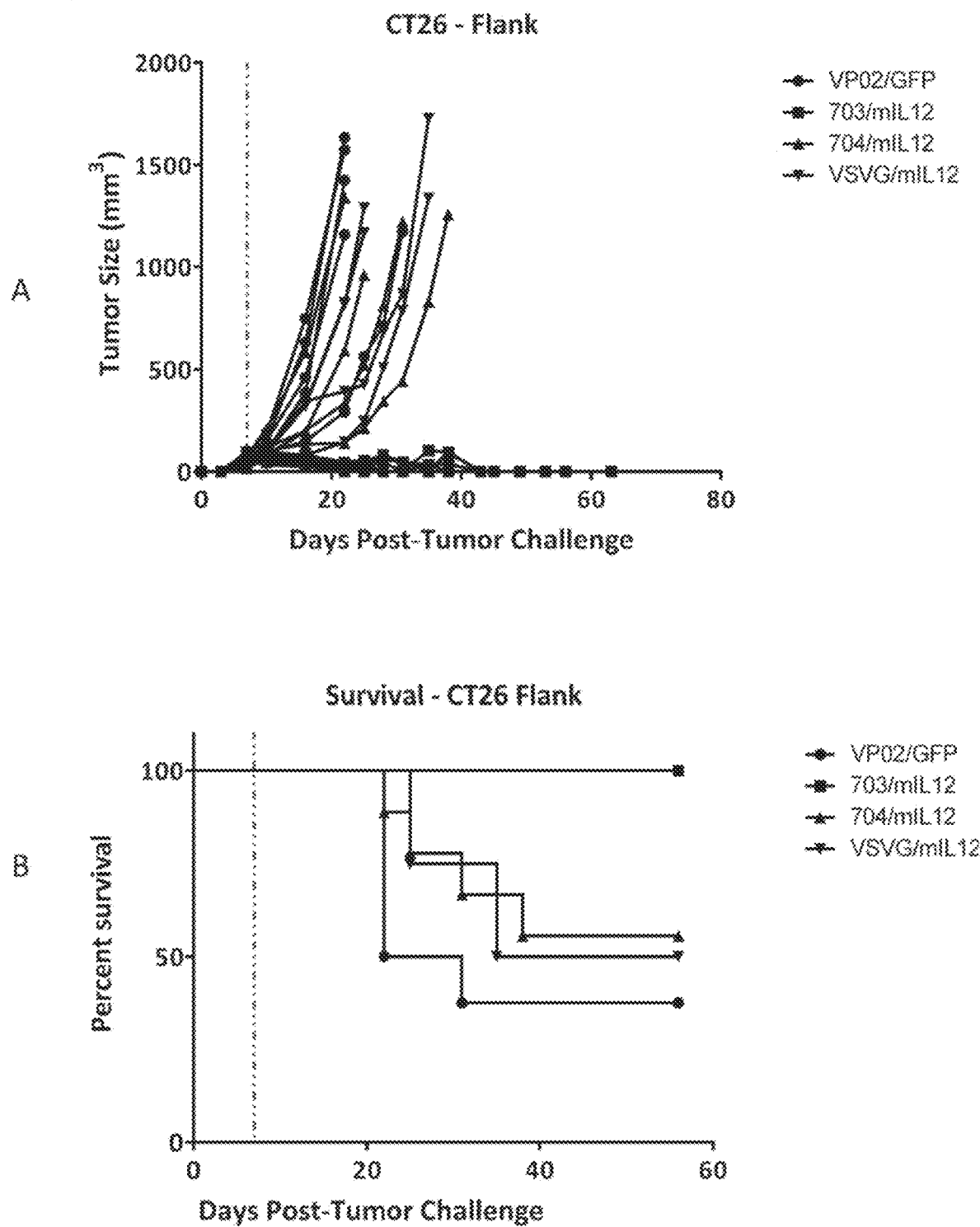
FIG. 12A and FIG. 12B show the antitumor efficacy of intratumoral injection of LV/IL-12 in a CT26 flank murine tumor model.
Figure 13:
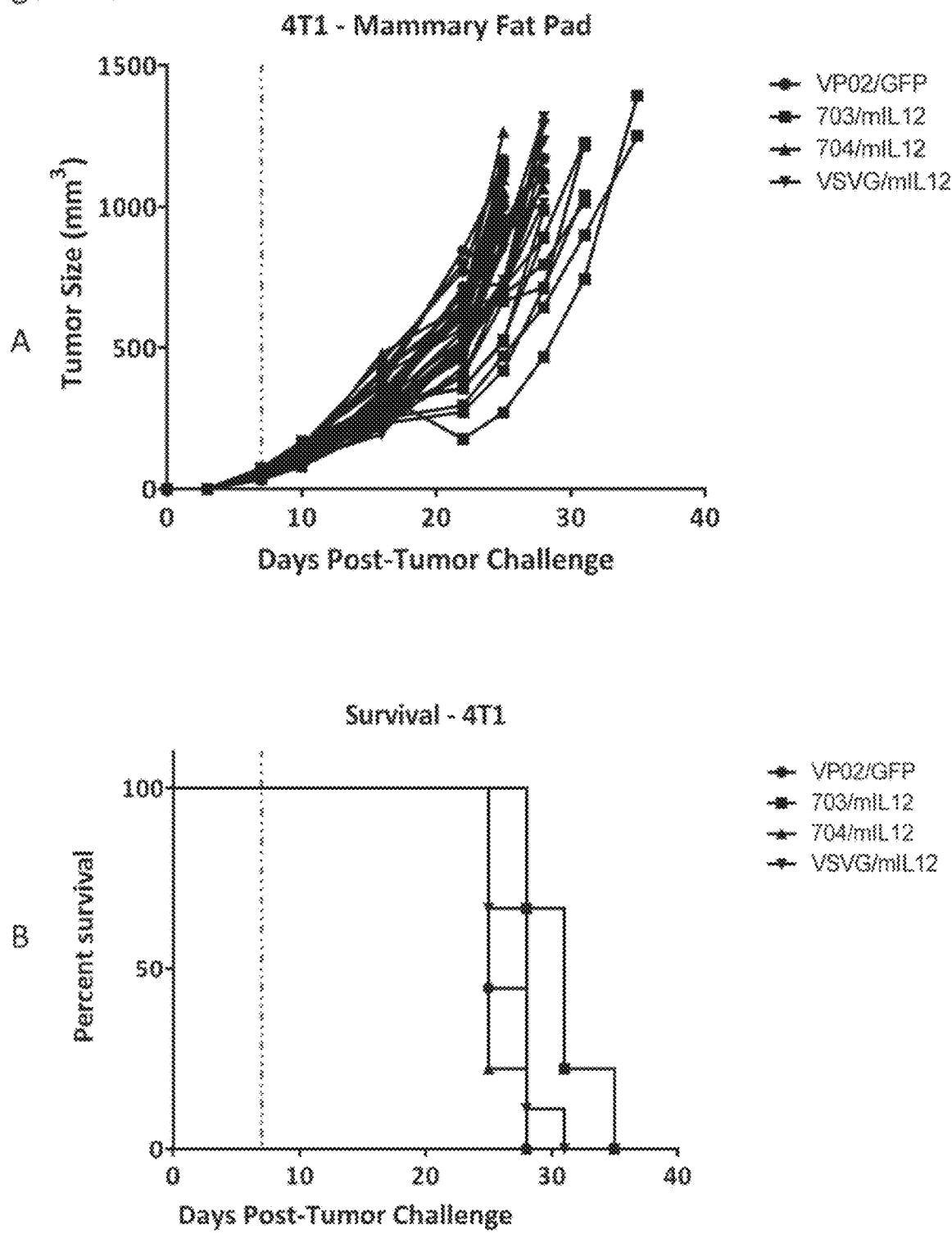
FIG. 13A and FIG. 13B show the antitumor efficacy of intratumoral injection of LV/IL-12 in a 4T1 murine tumor model.
Figure 14:
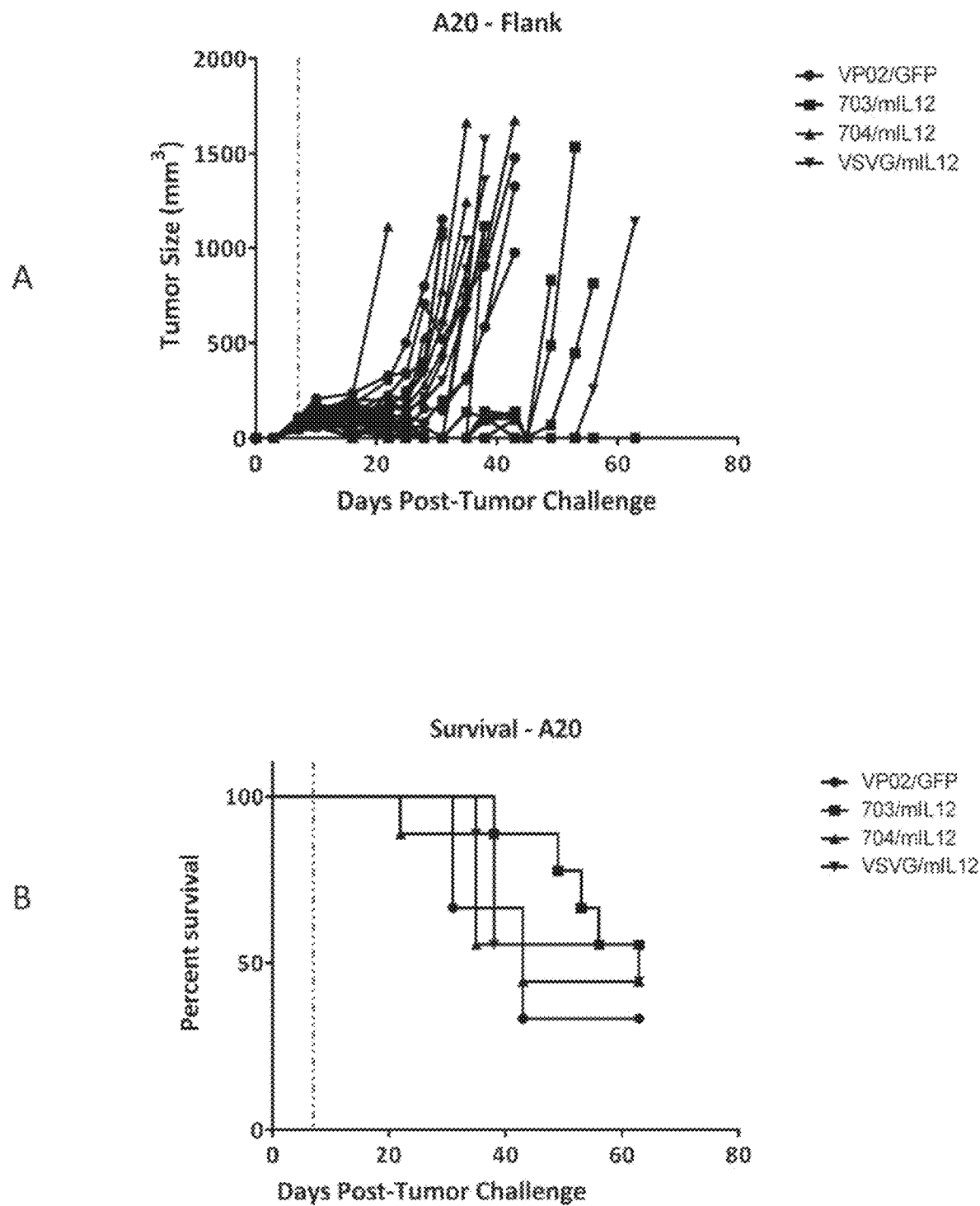
FIG. 14A and FIG. 14B show the antitumor efficacy of intratumoral injection of LV/IL-12 in an A20 murine tumor model.

Of the cytokines tested, VP02/IL-23 was able to significantly enhance LV305-induced CD8 T cell responses in PBMC after a prime (See FIG. 8).

Example 6

Single Intra-Tumoral Administration of Lentiviral Vector Expressing IL-12 Resulted in Significant Anti-Tumor Efficacy in 6 Out of 6 Murine Tumor Models Tested This Example shows that intra-tumoral injection of lentiviral vector expressing IL-12 was significantly effective in six out of six murine tumor models tested.

Intra-tumor LV/IL-12 administration was tested in 6 different murine tumor models using the methods outlined below.

Methods

Day 0: Inoculate mice with tumor cells. Day 7: Immunize mice with LV, pseudotyped with a modified Sindbis envelope, expressing IL-12 (LV703—integrating version; 704—integration deficient version, also referred to as VP02) or LV/IL-12 (integration deficient) pseudotyped with VSVG instead of a modified Sindbis envelope. Mice were sacrificed as tumors reach >100 mm2 (footpad) or 200 mm2 (flank).

Mice were monitored for 6+ weeks for tumor growth and survival.

As shown in FIGS. 9-14, LV/IL-12 was highly effective in reducing tumor growth and increasing survival in treated animals in all 6 of the tumor models that were tested. The 703/mIL-12 lentiviral vector, an integrating lentiviral vector pseudotyped with a modified Sindbis E2 glycoprotein, achieved the best antitumor efficacy across all tumor models. While not as efficacious as the 703 vector, the integration deficient vectors (704/mIL-12 (also referred to as VP02/IL-12) and VSVG/mIL-12) were also effective at delaying tumor growth and increasing survival.

Additional experiments were carried out to determine IL-12 levels in supernatants obtained from 293-DC-SIGN cells transduced with the vectors used in the intratumoral injection experiments described above. Both integrating and non-integrating versions of the vector were tested for production of IL-12 48 hours post transduction in the presence or absence of nevirapine. In particular, on day 0, 1E6 293-DC-SIGN cells were plated into 6 well plates in 2 mL of complete DMEM. On day 1, the cells were transduced with 8.5E9 vector genomes in the absence and presence of nevirapine. The transduction was carried out in 600 µL of complete DMEM±nevirapine and then 0.9 mL of complete DMEM±nevirapine was added 6 hours later. On day 3 (48 hours post transduction), the supernatants were filtered through a 0.45 µm filter. A standard ELISA was carried out using a commercially available kit R&D kit M1270). The results are shown in the table below. The number in parentheses shows IL-12 measured in presence of nevirapine.

| Vector Preparation | IL-12 ng produced by 1E10 genomes (+nev) |
|---|---|
| (704-SinVar1(VP02)-IL-12)- D64V Integrase | 383.7 (20.9) |
| (703-SinVar1-IL-13)- WT Integrase | 892.1 (16.5) |
| (704-VSVG-IL-12)- D64V Integrase | 764.9 (34.3) |

Although no comparative studies have been carried out, relatively low expression spread over a longer period of time as compared to vectors based on acute virus families, which express higher levels of IL-12 over a shorter period of time, may contribute to the surprising efficacy observed in the above experiments, and may also be advantageous for the safety profile. Further, specifically targeting expression of IL12 in dendritic cells, the cells best known to produce IL-12 physiologically, as opposed to randomly injecting into any tumor cell by electroporation or via other amphotropic viruses, could contribute to the unexpectedly effective anti-tumor responses.

Example 7

Single Intra-Tumoral Administration of Lentiviral Vector Expressing IL-12 in Combination with Anti-CTLA-4 Antibody and/or GLA-AF Resulted in Significant Anti-Tumor Efficacy in 3 Out of 3 Murine Tumor Models Tested This Example shows that intra-tumoral injection of lentiviral vector expressing IL-12 in combination with anti-CTLA-4 antibody and/or GLA-AF/SE was significantly effective in three out of three murine tumor models tested.

Intra-tumor LV/IL-12 administration in combination with anti-CTLA-4 antibody and/or GLA-AF/SE was tested in 3 different murine tumor models using the methods outlined below.

Methods

Day 0: Inoculate mice with tumor cells (right side). Day 7: Inoculate mice with tumor cells (left side). Immunize mice with LV703/IL-12 (703—integrating version; 1.3E10 genomes; 5.4 ng rIL12 in prep per mouse) or LV703/IL-12/RTmut (703—integrating version; reverse transcriptase mutated to eliminate its activity; 9.8E9 genomes; 5.4 ng rIL12 in prep per mouse) with or without anti-CTLA-4 or GLA. Anti-CTLA-4 was administered once a week until the end of study. In mice that received GLA, the first GLA dose (given on Day 7) was GLA-AF, mixed with vector, and then administered intra-tumorally. Subsequent doses of GLA were GLA-SE, administered once a week until the end of study. Mice were sacrificed as tumors reach >100 mm$^2$ (footpad) or 200 mm$^2$ (flank).

Mice were monitored for 6+ weeks for tumor growth and survival.

As shown in FIGS. 17-19, 703/IL-12 alone was highly effective in reducing tumor growth and increasing survival in treated animals in all 3 of the tumor models that were tested, confirming the results shown in EXAMPLE 6. This therapeutic benefit was driven by the presence of vector particles with intact reverse transcriptase, as tumor growth in mice treated with LV703/IL-12/RTmut was similar to non-treated tumor-bearing mice. Additional observations in each of the tested tumor models are detailed as follows.

In the B16 footpad model (FIG. 17), intra-tumoral LV703/IL-12 administration in the primary tumor (right side) significantly delayed tumor growth in the non-treated distal site (left side), a phenomena known as the abscopal effect. The addition of anti-CTLA-4 antibody further delayed the growth of the primary tumor but not the distal tumor.

In the B16 flank model (FIG. 18), intra-tumoral LV703/IL-12 administration in the primary tumor significantly delayed tumor growth in the non-treated distal site. The addition of anti-CTLA-4 antibody did not further delay the growth of the primary tumor (presumably because LV703/IL-12 alone was successful in suppressing nearly all tumor growth) but did further delay growth of the distal tumor (see FIG. 18B). In this model, a single intratumoral injection of LV703/IL-12 led to regression of primary tumors and delayed growth of untreated secondary tumors. Mice with regressed tumors failed to reject a second tumor challenge, suggesting suboptimal generation of immunological memory.

Figure 19:
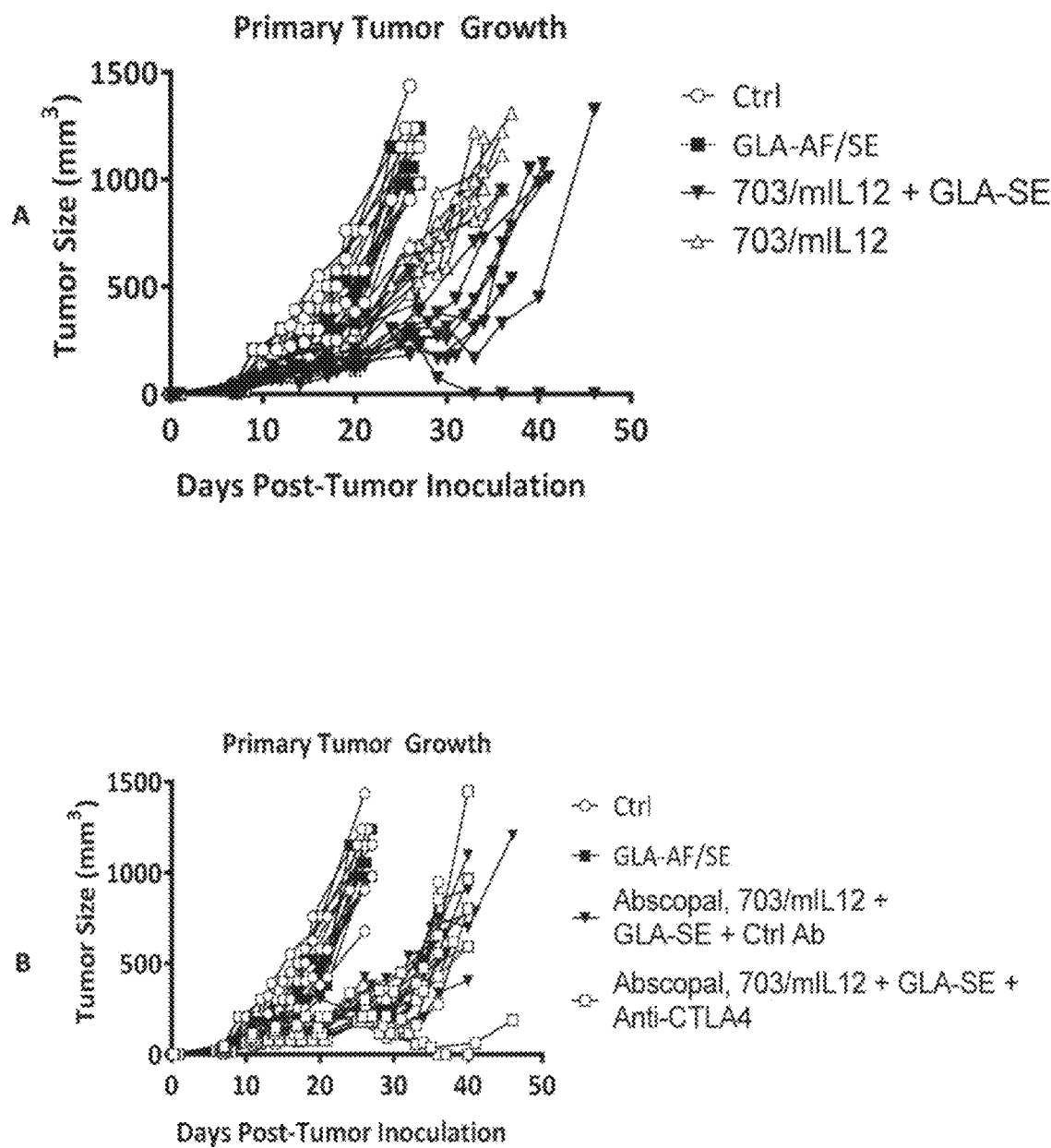
Figure 19:
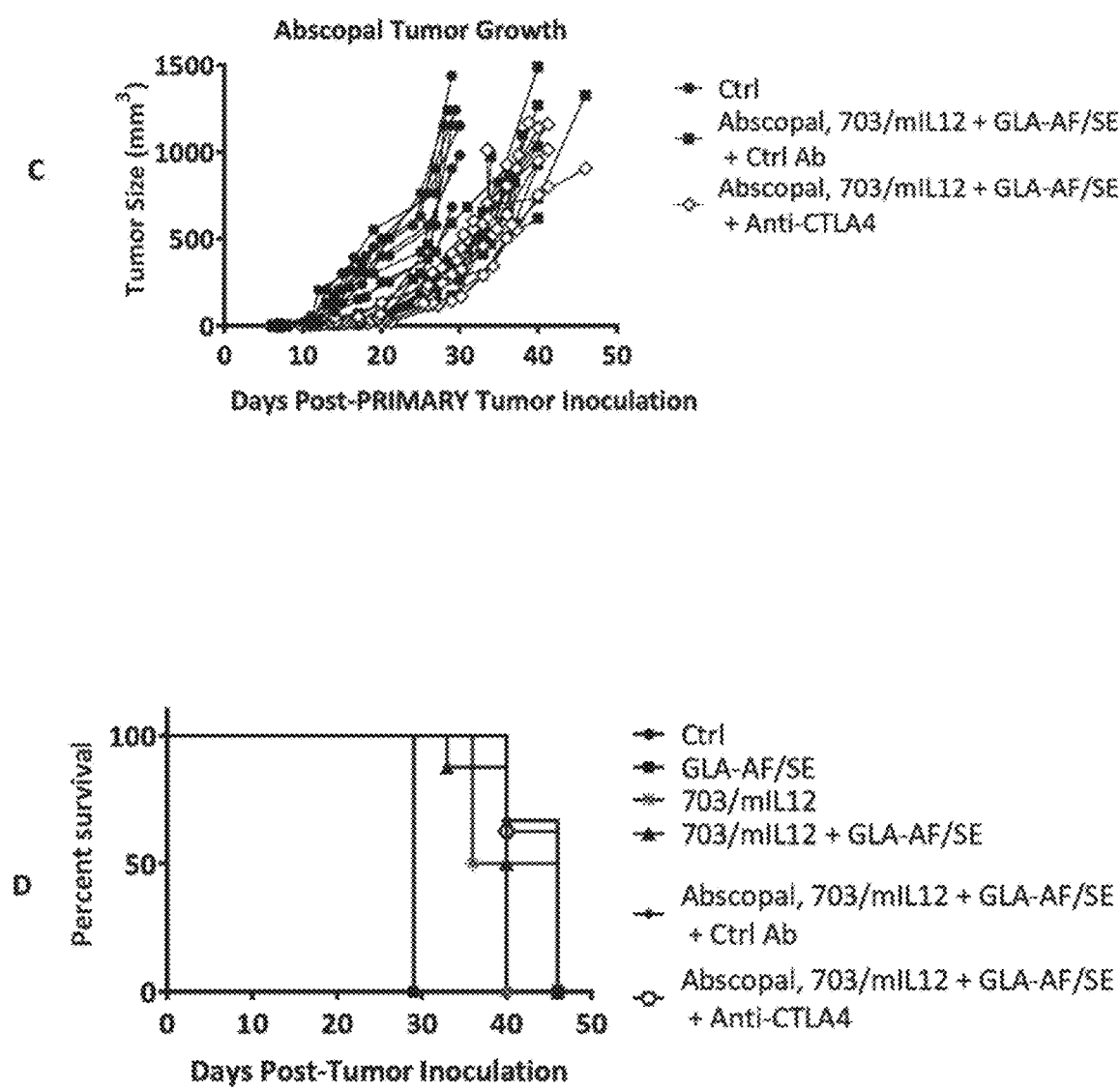

In the 4T1 breast tumor model (FIG. 19), as noted above, intra-tumoral LV703/IL-12 administration in the primary tumor significantly delayed primary tumor growth. Additional intra-tumoral administration of GLA-SE further delayed growth of the primary tumor (FIG. 19A). Intra-tumoral LV703/IL-12+GLA-SE administration in the primary tumor also resulted in delayed tumor growth in the non-treated distal site (FIG. 19C). The addition of anti-CTLA-4 antibody to LV703/IL-12+GLA-SE did not further delay the growth of the primary or distal tumor (presumably because 4T1 is an aggressively invasive tumor model, with animals dying from asphyxiation due to tumor spread to the lungs; see FIGS. 19B and 19C). Survival of animals are tabulated in Table 4.

TABLE 4

| Interim Survival Data | Day 29 | Day 33 | Day 36 |
| --- | --- | --- | --- |
| Untreated | 0/10 | 0/10 | 0/10 |
| GLA-AF/SE only | 0/10 | 0/10 | 0/10 |
| LV703/IL12 | 10/10 | 10/10 | 5/10 |
| LV703/IL12 + GLA-AF/SE | 20/20 | 19/20 | 19/20 |
| LV703/IL12 + GLA-AF/SE + aCTLA4 Ab | 10/10 | 10/10 | 10/10 |

Thus, the above Examples support the use of LV/IL-12 alone or in combination with checkpoint inhibitors and/or TLR4 agonists for the treatment of cancer and other diseases that benefit from immunotherapy.

Example 8

VP02/IL-12 Significantly Increased Antigen Specific CD4 T Cell Responses when Coadministered with Recombinant Protein and GLA/SE The experiments in this Example were conducted to evaluate the immunogenicity of co-administration VP02/IL-12 with recombinant protein+GLA/SE, a synthetic lipid A TLR4 agonist adjuvant.

Female B6D2/F1 mice were immunized with VP02/IL-12 and recombinant NY-ESO-1 (rNY-ESO-1), with or without GLA/SE, s.c. injected at the base of the tail (see Table 5). Splenic T cell responses were measured 7 days post-immunization by ICS after ex vivo re-stimulation with CD4 and CD8 reactive peptides.

TABLE 5

| Group | n = | VP02/IL-12 Genomes | rNY-ESO-1 Treatment | GLA/SE |
| --- | --- | --- | --- | --- |
| 1 | 5 | — | — | − |
| 2 | 5 | — | 5 µg | − |
| 3 | 5 | 1.5E10 | — | − |
| 4 | 5 | 1.5E9 | 5 µg | − |
| 5 | 5 | 1.5E8 | 5 µg | − |
| 6 | 5 | 1.5E7 | 5 µg | − |
| 7 | 5 | 1.5E6 | 5 µg | − |
| 8 | 5 | — | 5 µg | + |
| 9 | 5 | 1.5E9 | 5 µg | + |
| 10 | 5 | 1.5E8 | 5 µg | + |
| 11 | 5 | 1.5E7 | 5 µg | + |
| 12 | 5 | 1.5E6 | 5 µg | + |

Figure 15:
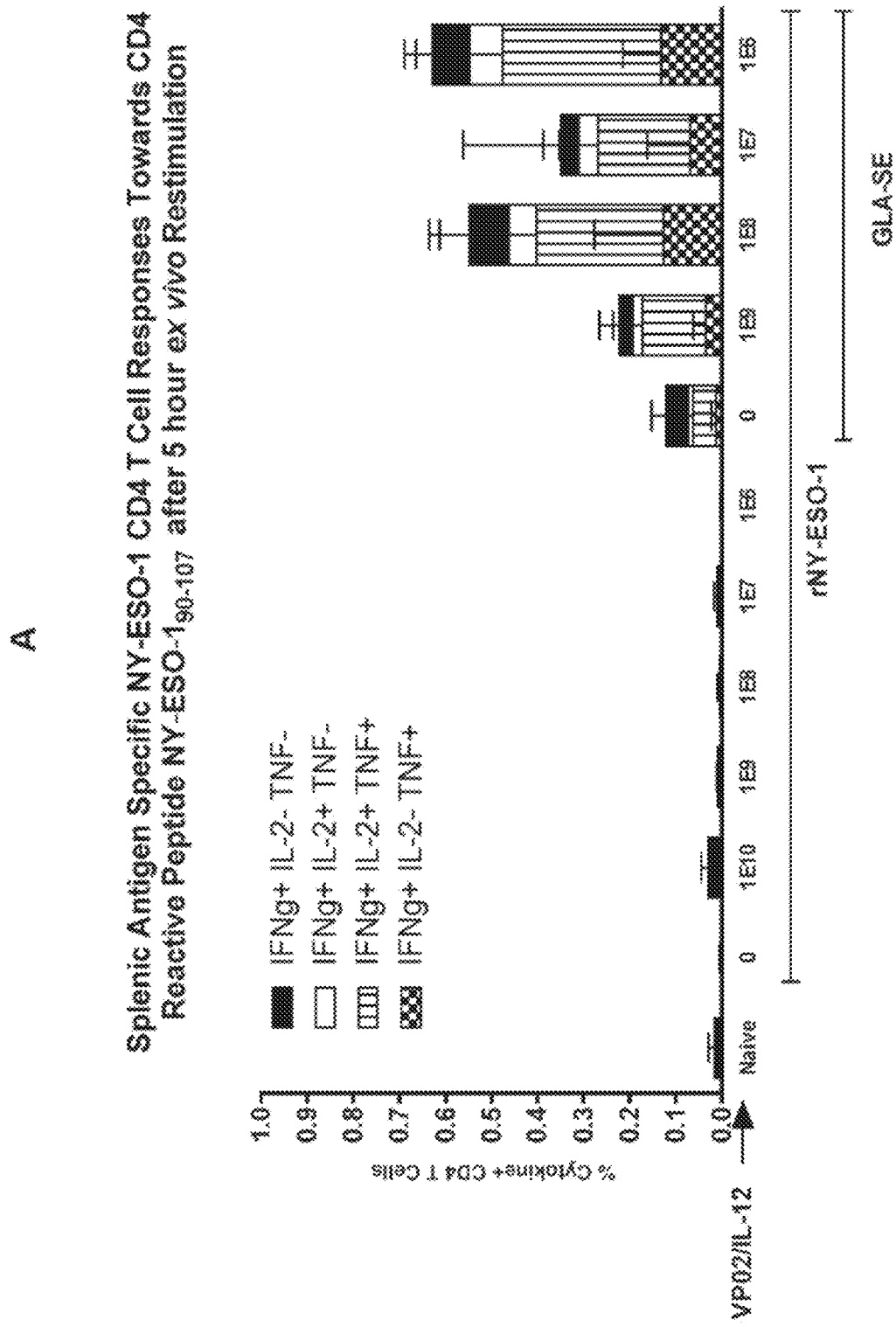
FIG. 15A and FIG. 15B show that the addition of VP02/IL-12 significantly increased NY-ESO-1 Ag-specific CD4 T cell responses when co-administered with rNY-ESO-1+ GLA-SE mixed together and administered s.c. at the base of the tail.
Figure 15:
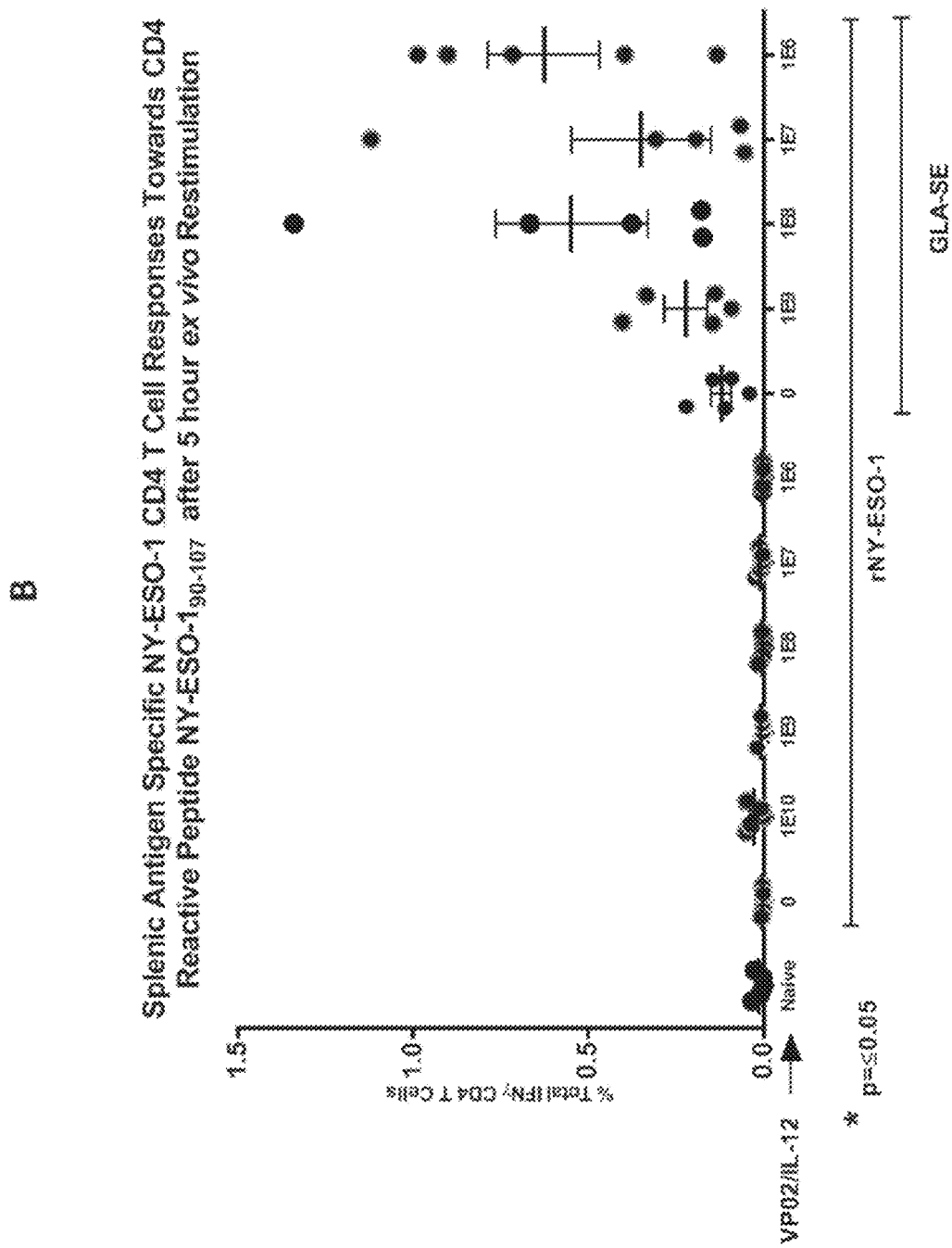

The results are shown in FIG. 15. As expected, recombinant protein with GLA-SE induced a TH 1 CD4 T cell response. FIG. 15A shows the percent cytokine positive CD4 T cells and FIG. 15B shows the percent total IFNγ CD4 positive T cells. The results show that the addition of VP02/IL-12 significantly increased NY-ESO-1 Ag-specific CD4 T cell responses when co-administered with rNY-ESO-1+GLA-SE mixed together and administered s.c. at the base of the tail.

Figure 16:
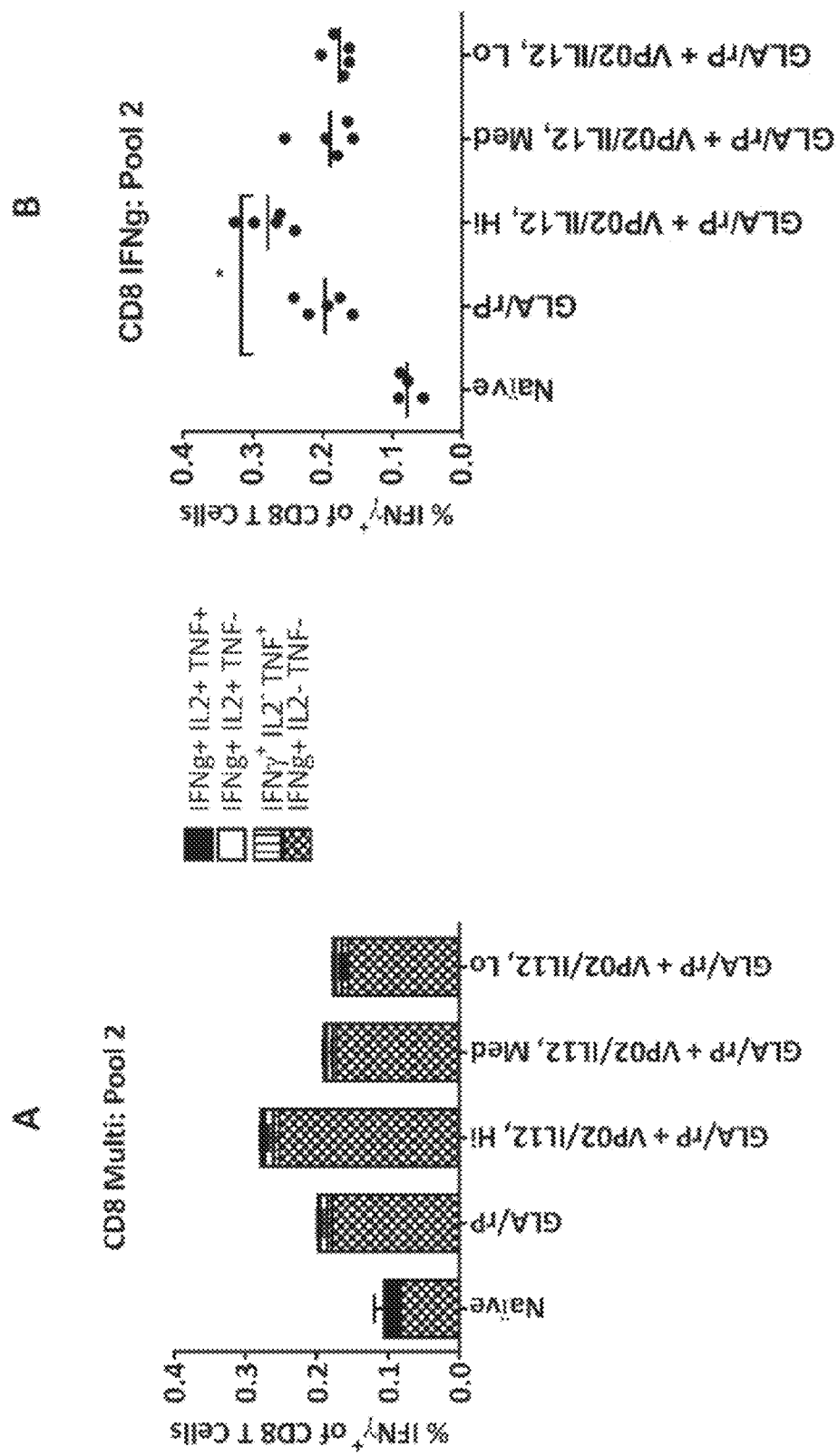
FIG. 16A, FIG. 16B, FIG. 16C, and FIG. 16D show that the addition of VP02/IL-12 significantly boosted CD8 T cell responses (FIG. 16A and FIG. 16B) but decreased CD4 T cell responses (FIG. 16C and FIG. 16D) in experiments using recombinant hepatitis B surface antigen (rHBsAg) in combination with GLA-SE.
Figure 16:
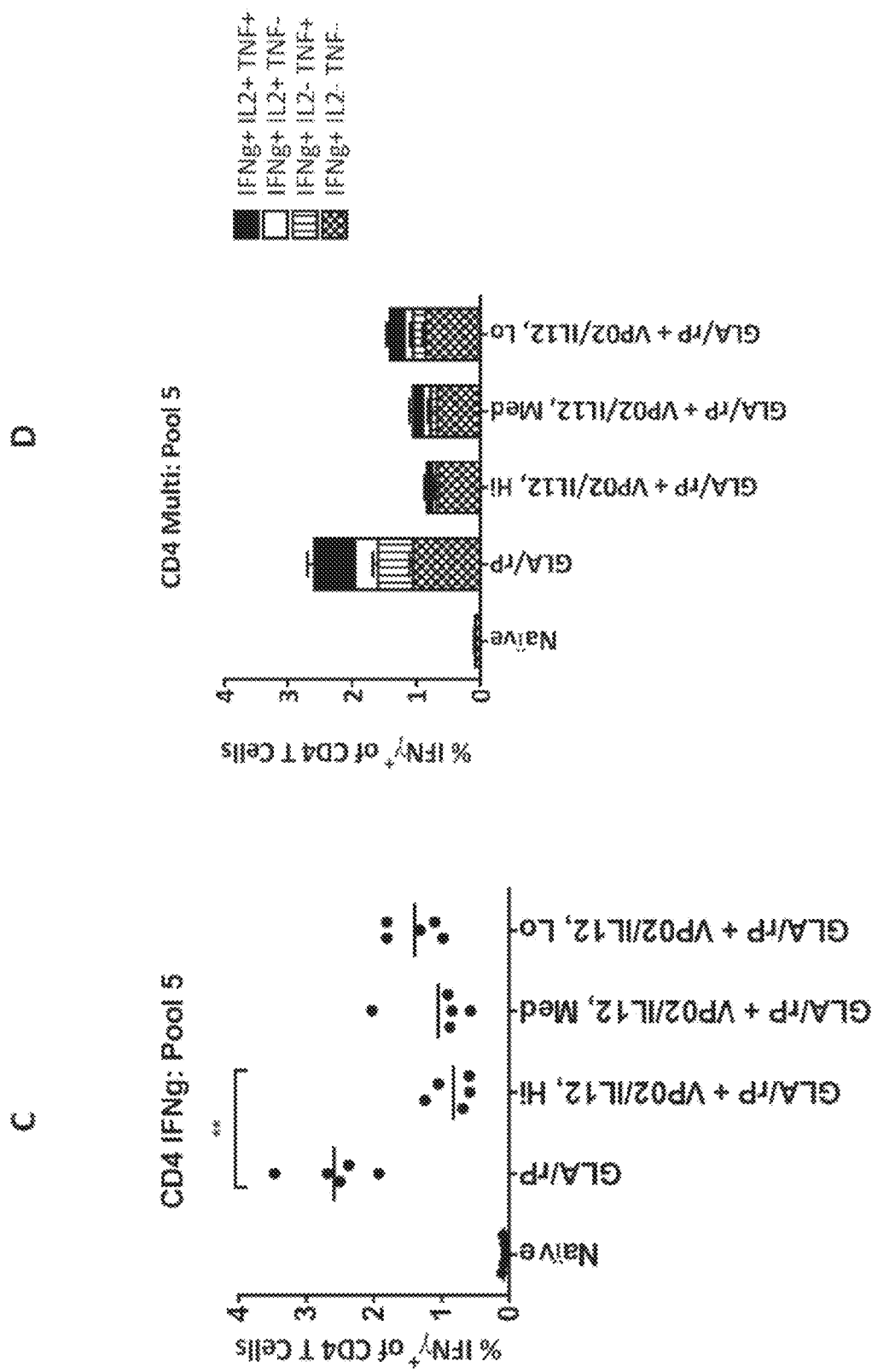
Figure 17:
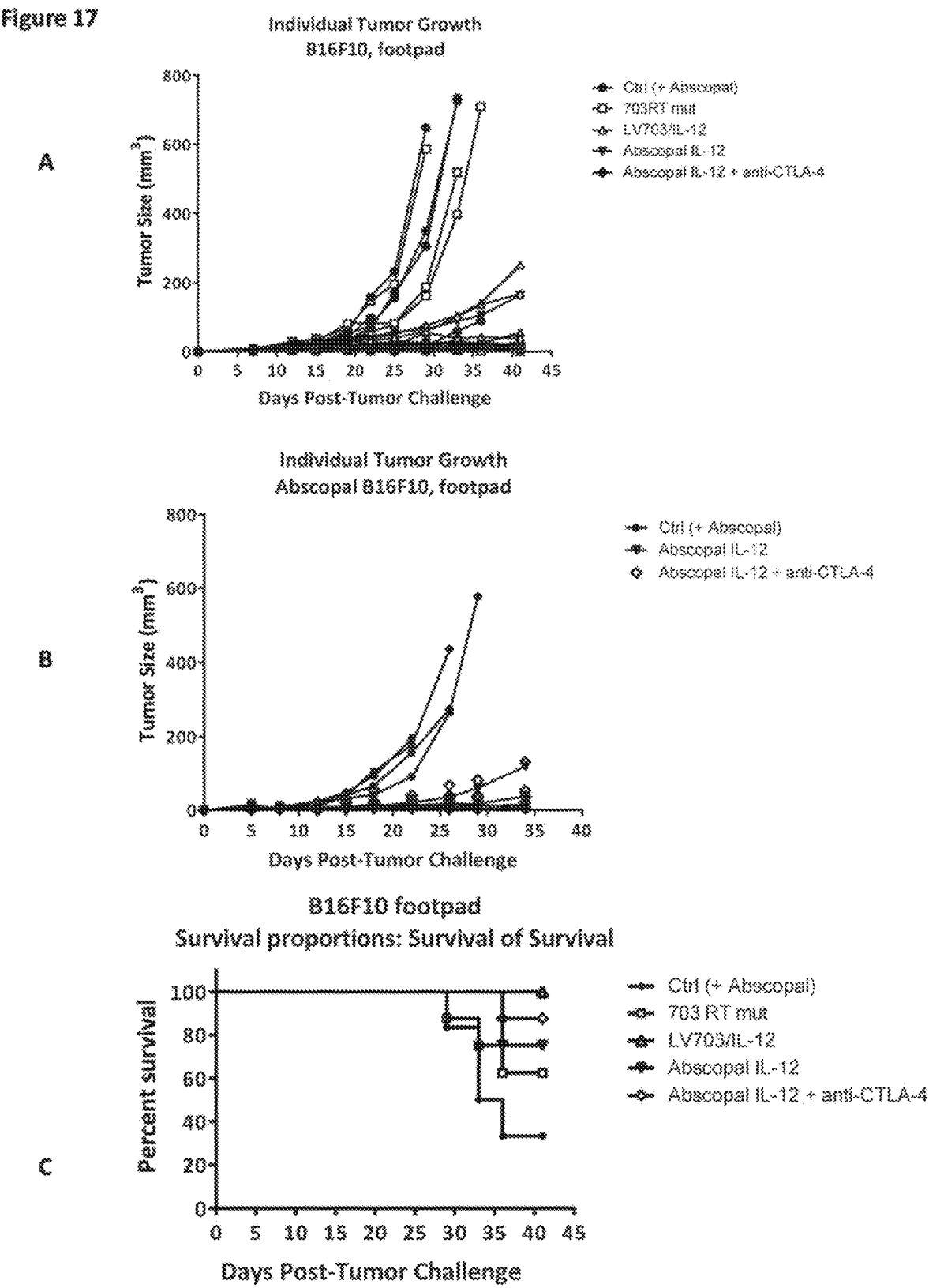
FIG. 17A, 17B, 17C: C57BL/6 female mice (n=8/group) were inoculated with $1\times10^6$ B16F10 melanoma cells in the right footpad. On Day 7, tumor-bearing mice were inoculated with $1\times10^6$ melanoma cells in the left footpad. The mice were then immunized with an integrating LV/IL-12 (LV703) or LV703/IL-12/RTmut or control vector, IT±200 µg anti-CTLA-4 antibody or isotype control, IP. Antibody was administered once per week, until the end of study. 17A, individual tumor growth; 17B individual abscopal tumor growth; 17C, Survival proportions.
Figure 18:
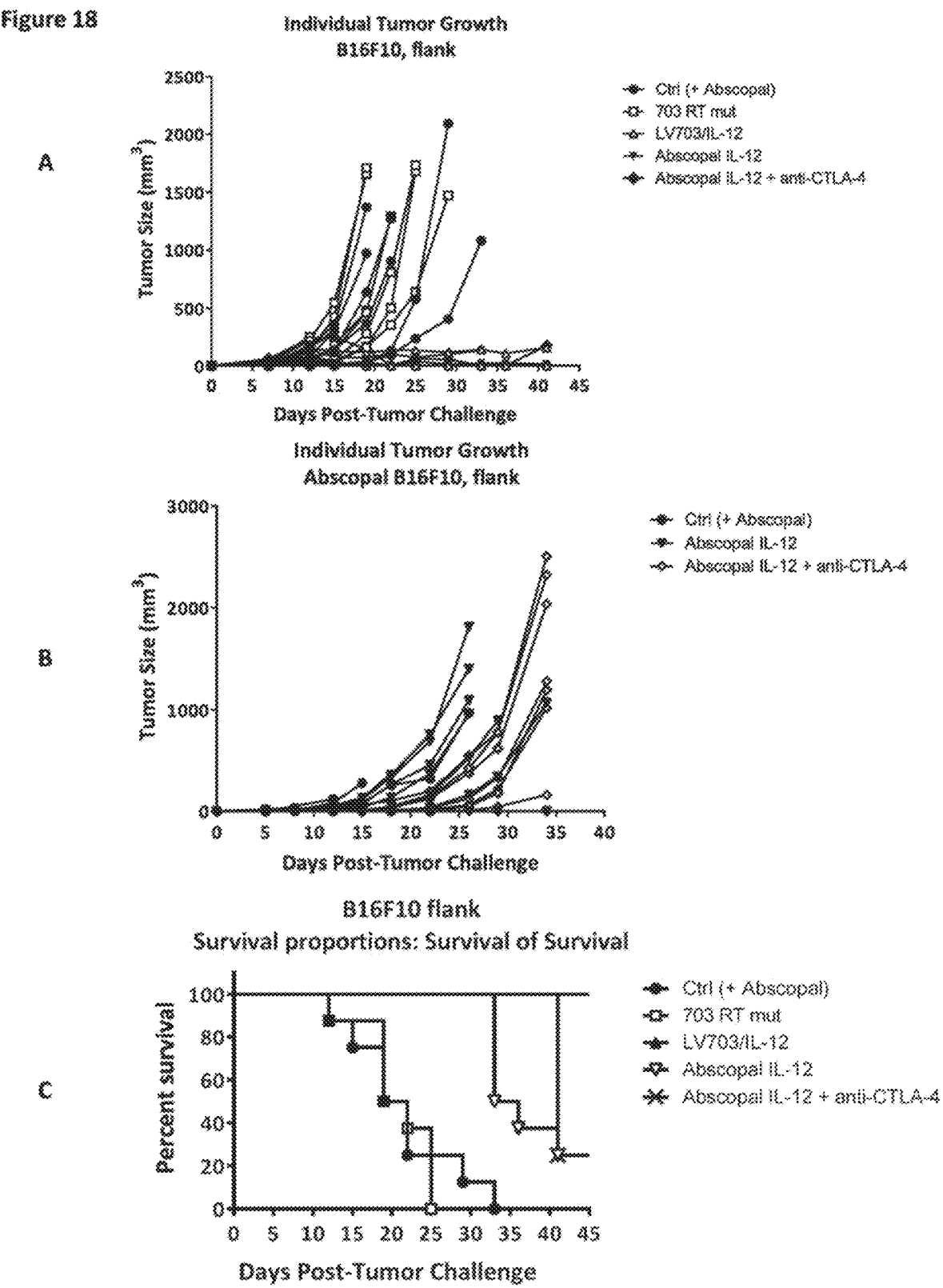

In a separate experiment using recombinant hepatitis B surface antigen (rHBsAg) in combination with GLA-SE, the addition of VP02/IL-12 significantly boosted CD8 T cell responses (FIGS. 16A and 16B) but decreased CD4 T cell responses (FIGS. 16C and 16D).

The decrease, or at least lack of increase, in CD4 response levels stand out in comparison to the effect seen for VP02/IL12 enhancement of responses against VP02 expressing antigens. A possible explanation is that antigen-expressing VP02 does not induce high CD4 responses alone, whereas GLA with recombinant protein antigen induce significant CD4 levels. Therefore, the addition of IL12 may not provide additional stimulation for CD4 induction.

Example 9

IL-12 and IFNγ Detected in the Blood of Mice Treated with Intratumoral LV/IL-12

The experiments in this Example were conducted to evaluate the plasma levels and kinetics of IL-12 and IFNγ following intratumoral injection of LV/IL-12.

Figure 20:
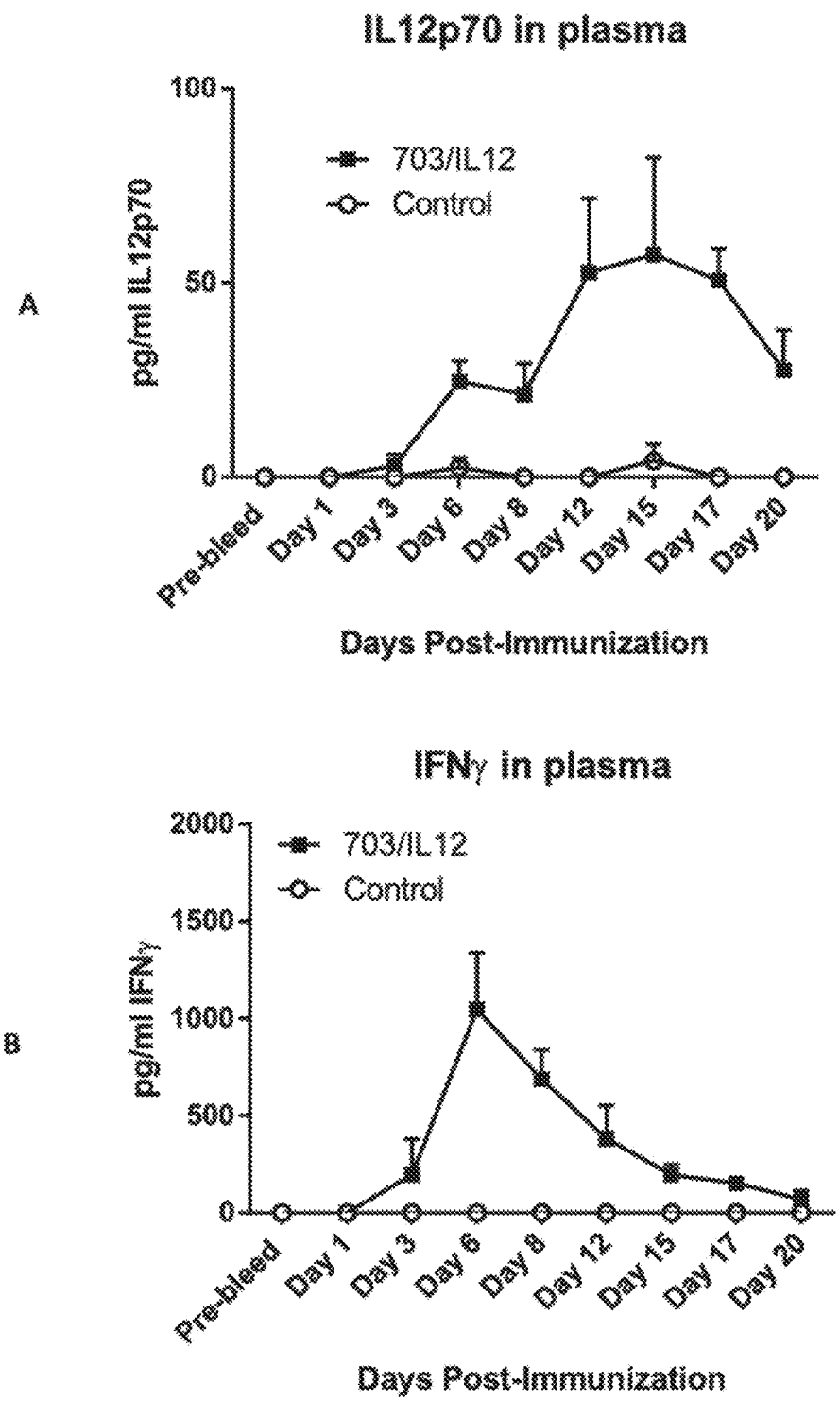

Mice (6 females/group) were inoculated with $1 \times 10^5$ B16 tumor cells. When tumors became palpable (Day 7), mice were immunized with LV703/mIL12, IT. On days 0 (pre-bleed), 1, 3, 6, 8, 12, 15, 17 and 20, blood was drawn to measure the amount of IL-12 and IFNγ present in the plasma. Tumor growth was monitored 2-3 times per week. Mice were sacrificed as tumor area exceeded 200 mm² (flank). As shown in FIG. 20, increased IL12 and IFNγ were detected in the blood of mice injected with intratumoral LV703/mIL12.

Example 10

Cell Depletion Studies in Mice Treated with Intratumoral LV/IL-12

The experiments in this Example were conducted to investigate which cells were responsible for the anti-tumor effect in mice treated with intratumoral LV/IL-12.

Methods

Mice (10-20 females/group) were inoculated with $1 \times 10^5$ B16 tumor cells. Depletion of specific immune cell subsets with antibodies (200 ug) started on Day 4 and continued twice weekly. When tumors became palpable (Day 7), mice were immunized with LV703/mIL12, IT. Tumor growth was monitored 2-3 times per week. Mice were sacrificed as tumor area exceeded 200 mm² (flank).

As shown in FIG. 21 and confirming prior experiments, a single intratumoral injection of LV703/IL12 led to regression of tumors. Depletion of single immune cell subsets did not abrogate anti-tumor efficacy induced by i.t. LV/IL12. See in particular FIGS. 21A and 21B. Additionally, depletion of CD4 and NK cells together also did not abrogate anti-tumor efficacy induced by i.t. LV/IL-12. Depletion of CD8 T cells did show that these cells are required, but not sufficient, for mediating anti-tumor control in mice injected with i.t. LV703/IL-12. (See e.g., FIG. 21 where depletion of only CD8 cells did not abrogate anti-tumor effect but when combined with depletion of CD4 cells, NK cells or both, tumor control was abrogated.)

At day 98 of this experiment out of 41 total mice remaining, eight mice had a tumor; 33 mice had no tumor, further confirming the unexpected efficacy of the intratumoral treatment with LV/IL12.

Interestingly, severe vitiligo was observed in mice injected with intratumoral LV/IL12 and depleted of CD4 T cells (see FIGS. 21B and 21E). This effect was only observed when CD8 T cells were present, suggesting i.t. LV703/IL-12 generated at least a subset of effector CD8 T cells that targeted melanocytes, leading to depigmentation of fur color (vitiligo). Vitiligo is a commonly observed onset of autoimmune disease as the result of strong induction of melanoma-specific anti-tumor efficacy. Furthermore, since vitiligo was observed only in i.t. LV703/IL-12-treated mice depleted of CD4 T cells, deletion of regulatory T cells may further improve i.t. LV703/IL-12 therapy.

In summary, local (intratumoral) administration of LV/mIL12 promotes systemic CD8 T cell-mediated anti-tumor response (turns a cold tumor hot). Without being bound by theory, it is possible that for optimal development of immunological memory, regulatory T cells may need to be depleted.

Example 11

Regulatory T Cell Depletion Studies in Mice Treated with Intratumoral LV/IL-12

Experiments are conducted to investigate the therapeutic efficacy of the combination of regulatory T cell depletion and intratumoral IL-12 administration.

Methods

Mice (10-20 females/group) are inoculated with $1 \times 10^5$ B16 tumor cells. Depletion of regulatory T cells with low dose cyclophosphamide, anti-CD25 or anti-CTLA4 antibodies (200 ug), or diphtheria toxin (see below) is started on Day 4 and continued twice weekly. When tumors became palpable (Day 7), mice are immunized with LV703/mIL12, intratumorally. Tumor growth is monitored 2-3 times per week. Mice are sacrificed as tumor area exceeded 200 mm² (flank).

Regulatory T cells are also depleted using transgenic mice (e.g., DEREG or Foxp3.LuciDTR mice). These mice can carry a diphtheria toxin receptor (DTR) transgene under the control of a Foxp3 promoter, thereby allowing specific depletion of regulatory T cells via administration of diphtheria toxin at any time point (see e.g., Li et al., Eur J Immunol 2010, 40:3325-3335).

Without being bound by theory, depletion of regulatory T cells further improves i.t. LV703/IL-12 therapy. Memory cell may be measured to determine increase in memory phenotype cells as compared to groups not receiving regulatory T cell depletion therapy. Further experiments are conducted to re-challenge mice whose tumors regress to determine if therapy is sufficient to abrogate tumor growth following re-challenge.

The sequences disclosed in the sequence listing are also provided in WO2011011584:

| SEQ ID NO | DESCRIPTION |
| --- | --- |
| 1 | Sindbis virus E2 glycoprotein |
| 2 | SVGmu |
| 3 | E2 variant |
| 4 | E2 variant |
| 5 | E2 variant |
| 6 | E2 variant |
| 7 | E2 variant |
| 8 | E2 variant |
| 9 | E2 variant |
| 10 | E2 variant |
| 11 | E2 variant |
| 12 | E2 variant |
| 13 | E2 variant |
| 14 | E2 variant |
| 15 | E2 variant |
| 16 | E2 variant |
| 17 | Exemplary sequence of envelope glycoproteins of Sindbis virus, strain |
| 18 | E2 protein of the HR strain |
| 19 | Sindbis protein |
| 20 | E3/E2 polyprotein sequence |
| 21 | Vector U3 region |
| 22 | Vector U3 region |
| 23 | Vector U3 region |
| 24 | OVA257 peptide |
| 25 | AH1A5 peptide |
| 26 | RSKRS of E2/E3 fusion |
| 27 | RSKR of E2/E3 fusion |
| 28 | FLAG epitope tag |

As used herein and in the appended claims, the singular forms "a," "and," and "the" include plural referents unless the context clearly dictates otherwise. Thus, for example, reference to "an antigen" includes a plurality of such antigens, and reference to "a cell" or "the cell" includes reference to one or more cells and equivalents thereof (e.g., plurality of cells) known to those skilled in the art, and so forth. Similarly, reference to "a compound" or "a composition" includes a plurality of such compounds or compositions, and refers to one or more compounds or compositions, respectively, unless the context clearly dictates otherwise. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The various embodiments described above can be combined to provide further embodiments. All U.S. patents, U.S. patent application publications, U.S. patent application, foreign patents, foreign patent application, non-patent publications, and sequences referred to by accession number, referred to in this specification and/or listed in the Application Data Sheet are incorporated herein by reference, in their entirety. Aspects of the embodiments can be modified if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A lentiviral vector particle comprising:
   a. an envelope comprising an E2 glycoprotein variant, wherein (i) residue 160 of the E2 glycoprotein variant (corresponding to amino acid 225 of SEQ ID NO: 3) is absent or is an amino acid other than glutamic acid, (ii) at least one of residues 63, 70, 76, 84, 97, 104, 129, 131, 133, 139, 148, 149, 159, 65, 92 128, 137, 157, 170, and 172 of the E2 glycoprotein variant is a non-basic residue, and (iii) the E2 glycoprotein variant is not part of a fusion protein with Sindbis virus E3 glycoprotein; and
   b. a lentiviral vector genome comprising a polynucleotide sequence encoding IL-12.

2. The lentiviral vector particle of claim 1 wherein the IL-12 is a single chain IL-12 (scIL-12).

3. The lentiviral vector particle of claim 2 wherein the scIL-12 comprises p35-L-p40 or p40-L-p35.

4. The lentiviral vector particle of claim 1 wherein the lentiviral vector genome further comprises a sequence encoding an antigen.

5. The lentiviral vector particle of claim 4 wherein the antigen is a tumor associated antigen, a viral antigen, a bacterial antigen or a fungal antigen.

6. The lentiviral vector particle of claim 5 wherein the tumor associated antigen is selected from the group consisting of prostatic acid phosphatase, prostate specific antigen, NKX3.1, prostate specific membrane antigen, PRAME; BAGE; RAGE, NY-ESO-1, SAGE, HAGE, GAGE, Plu-1, HASH-1, HasH-2, Cripto, Criptin, MART-1/Melan-A, gp100, gp75, mda-7, tyrosinase, tyrosinase-related protein, p53, Ras, c-Myc, A-Raf, B-Raf, and C-Raf, MAGE-A1, MAGE-A2, MAGE-A3, MAGE-A4, MAGE-A6, MAGE-A10, MAGE-A12, MART-1, BAGE, DAM-6, -10, GAGE-1, GAGE-2, GAGE-8, GAGE-3, GAGE-4, GAGE-5, GAGE-6, GAGE-7B, NA88-A, MART-1, MC1R, Gp100, PSM, TRP-1, TRP-2, ART-4, CAMEL, CEA, Cyp-B, hTERT, hTRT, iCE, MUC1, MUC2, PRAME, P15, RU1, RU2, SART-1, SART-3, Wilms' tumor antigen (WT1), AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, Epidermal Growth Factor receptor (EGFR and EGFRvIII), platelet derived growth factor receptor (PDGFR), vascular endothelial growth factor receptor (VEGFR), integrin-linked kinase (ILK), STAT3, STAT5, STAT6, HIF-1, HIF-2, Nuclear Factor-Kappa B (NF-κB), Notch1-4, c-Met, mammalian targets of rapamycin (mTOR), WNT, PMSA, PR-3, MDM2, Mesothelin, renal cell carcinoma—5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGs5, SART3, STn, PAX5, OY-TES1, sperm protein 17, LCK, HMWMAA, AKAP-4, SSX2, XAGE 1, B7H3, legumain, TIE2, Page4, MAD-CT-1, FAP, MAD-CT-2, and fos related antigen 1.

7. A composition comprising the lentiviral vector particle according to claim 1 and a second lentiviral vector particle encoding a tumor antigen.

8. A therapeutic or prophylactic vaccine comprising the lentiviral vector particles of claim 4 and a pharmaceutically acceptable excipient.

9. The lentiviral vector particle of claim 1, wherein the E2 glycoprotein variant comprises amino acids 66 to 488 of SEQ ID NO: 3.

10. A lentiviral vector particle comprising:

a. an envelope comprising an E2 glycoprotein variant having amino acids 66 to 488 of SEQ ID NO: 3, wherein (i) residue 160 of the E2 glycoprotein variant (corresponding to amino acid 225 of SEQ ID NO: 3) is absent or is an amino acid other than glutamic acid, (ii)

residue 70 of the E2 glycoprotein variant is a non-basic residue, and (iii) the E2 glycoprotein variant is not part of a fusion protein with Sindbis virus E3 glycoprotein; and b. a lentiviral vector genome comprising a nucleotide sequence encoding IL-12, wherein the IL-12 is a single chain IL-12 (scIL-12) comprising p35-L-p40 or p40-L-p35.

11. The lentiviral vector particle of claim 1, wherein residue 70 of the E2 glycoprotein variant is a non-basic residue.

\* \* \* \* \*

UNITED STATES PATENT AND TRADEMARK OFFICE
CERTIFICATE OF CORRECTION

| | | |
|---|---|---|
| PATENT NO. | : 11,365,230 B2 | Page 1 of 1 |
| APPLICATION NO. | : 15/774444 | |
| DATED | : June 21, 2022 | |
| INVENTOR(S) | : Ter Meulen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 184 days.

Signed and Sealed this
Eleventh Day of February, 2025

Coke Morgan Stewart
*Acting Director of the United States Patent and Trademark Office*